US012729206B2

(12) United States Patent
Kawaguchi et al.

(10) Patent No.: US 12,729,206 B2
(45) Date of Patent: Sep. 8, 2026

(54) 4-AMINOQUINAZOLINE COMPOUND

(71) Applicant: Astellas Pharma Inc., Tokyo (JP)

(72) Inventors: Kenichi Kawaguchi, Tokyo (JP); Kazuyuki Kuramoto, Tokyo (JP); Tomoyoshi Imaizumi, Tokyo (JP); Takahiro Morikawa, Tokyo (JP); Mitsuaki Okumura, Tokyo (JP); Sunao Imada, Tokyo (JP); Eiji Kawaminami, Tokyo (JP); Ryo Sato, Tokyo (JP); Yohei Seki, Tokyo (JP); Hisao Hamaguchi, Tokyo (JP); Hiroki Ishioka, Tokyo (JP); Hiroki Fukudome, Tokyo (JP); Ikumi Kuriwaki, Tokyo (JP); Takeyuki Nagashima, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 465 days.

(21) Appl. No.: 18/546,330

(22) PCT Filed: Feb. 14, 2022

(86) PCT No.: PCT/JP2022/005583
§ 371 (c)(1),
(2) Date: Aug. 14, 2023

(87) PCT Pub. No.: WO2022/173033
PCT Pub. Date: Aug. 18, 2022

(65) Prior Publication Data

US 2024/0150366 A1 May 9, 2024

(30) Foreign Application Priority Data

Feb. 15, 2021 (JP) ................................ 2021-021684

(51) Int. Cl.
*C07D 487/08* (2006.01)
*A61P 35/00* (2006.01)
*C07D 519/00* (2006.01)

(52) U.S. Cl.
CPC ............ *C07D 487/08* (2013.01); *A61P 35/00* (2018.01); *C07D 519/00* (2013.01)

(58) Field of Classification Search
CPC .................................................... C07D 487/08
USPC ......................................................... 514/249
See application file for complete search history.

(56) References Cited

U.S. PATENT DOCUMENTS

2014/0356322 A1 12/2014 Crews et al.
2018/0015087 A1 1/2018 Liu et al.
2019/0127336 A1 5/2019 Li et al.
2019/0292182 A1 9/2019 Kuramoto et al.
2019/0315732 A1 10/2019 Crew et al.
2020/0140437 A1 5/2020 Kuramoto et al.
2022/0363681 A1* 11/2022 Zhou .................... C07D 401/12

FOREIGN PATENT DOCUMENTS

EP 4223761 A1 8/2023
WO WO 2016/049565 A1 3/2016
WO WO 2016/049568 A1 3/2016
WO WO 2017/0172979 A1 10/2017
WO WO 2018/143315 A1 2/2018
WO WO 2021/041671 A1 3/2021
WO WO 2021/106231 A1 6/2021
WO WO 2021/107160 A1 6/2021
WO WO 2022/002102 A1 1/2022
WO WO 2022/015375 A1 1/2022
WO WO 2022/031678 A1 2/2022
WO WO 2022/042630 A1 3/2022
WO WO 2022/061251 A1 3/2022
WO WO 2022/068921 A1 4/2022
WO WO 2022/098625 A1 5/2022
WO WO 2022/105855 A1 5/2022
WO WO 2022/105857 A1 5/2022
WO WO 2022/105859 A1 5/2022
WO WO 2022/148422 A1 7/2022
WO WO 2022/171147 A1 8/2022

OTHER PUBLICATIONS

International Patent Application No. PCT/JP2022/005583, by Astellas Pharma Inc., filed Feb. 14, 2022, International Search Report and Written Opinion, mailed Apr. 19, 2022, (Japanese 7 pages).

* cited by examiner

*Primary Examiner* — Jeffrey H Murray
*Assistant Examiner* — Rilla Marie Samsell
(74) *Attorney, Agent, or Firm* — Finnegan, Henderson, Farabow, Garrett & Dunner LLP

(57) ABSTRACT

[Problem] A compound useful as an active ingredient of a pharmaceutical composition for treating pancreatic cancer is provided.
[Solution] The present inventors have studied about a compound that is useful as an active ingredient of a pharmaceutical composition for treating pancreatic cancer and have found that a 4-aminoquinazoline compound has an excellent G12D mutant KRAS inhibition activity and can be used as a therapeutic agent for pancreatic cancer, thus completing the present invention. The 4-aminoquinazoline compound of the present invention or a salt thereof can be used as a therapeutic agent for pancreatic cancer.

6 Claims, No Drawings

4-AMINOQUINAZOLINE COMPOUND

RELATED APPLICATIONS

This application is a U.S. National Stage Application under 37 C.F.R. § 371 of International Application No. PCT/JP2022/005583 filed Feb. 14, 2022, which claims priority to Japanese Patent Application No. 2021-021684, filed on Feb. 15, 2021, all of which are incorporated herein by reference in their entirety.

TECHNICAL FIELD

The present invention relates to pharmaceutical compositions and to a 4-aminoquinazoline compound that is expected to be useful as a G12D mutant KRAS inhibitor and to be useful as an active ingredient of, for example, a pharmaceutical composition for treating pancreatic cancer.

BACKGROUND ART

Pancreatic cancer mainly including pancreatic ductal adenocarcinoma is a cancer with a very poor prognosis having a five years survival rate of 10% or less (CA Cancer J. Clin., 2016, 66, p. 7-30), and about 460,000 new cases are reported per year in the world (CA Cancer J. Clin., 2018, 68, p. 394-424). The most effective therapy for treating pancreatic cancer is a surgery. However, the cancer has often metastasized since early detection is difficult, and therapeutic effects of a surgery cannot be expected in many cases. When the cancer is not treated by a surgery, chemotherapy or radiotherapy is adopted but the survival rate is not so good. Currently, the FOLFRINOX therapy (multidrug treatment of three chemotherapy agents of 5-FU, irinotecan and oxaliplatin, plus levofolinate) is used as a standard therapy of pancreatic cancer. However, due to the strong toxicity, the subject patient has to be cautiously selected, for example, the therapy is to be applied only to patients of an ECOG performance status of 1 or less (J. Clin. Oncol., 2018, 36, p. 2545-2556). As a molecular target drug, an epidermal growth factor receptor (EGFR) inhibitor, Erlotinib, has been approved in a combination therapy with Gemcitabine. However, the extension of the overall survival is only about two weeks as compared with Gemcitabine alone, and no satisfying therapeutic effect has been achieved. A highly effective therapeutic agent remains needed (J. Clin. Oncol., 2007, 25, p. 1960-1966).

RAS proteins are low molecular weight guanosine triphosphate (GTP)-binding proteins of about 21 kDa constituted of 188-189 amino acids and include four main types of proteins (KRAS (KRAS 4A and KRAS 4B), NRAS and HRAS) produced by three genes of a KRAS gene, an NRAS gene and an HRAS gene. RAS proteins are divided into an active GTP-binding type and an inactive GDP-binding type. A RAS protein is activated by replacement of guanosine diphosphate (GDP) with GTP due to, for example, ligand stimulation to a membrane receptor, such as EGFR. The active RAS binds to effector proteins as much as twenty, such as RAF, PI3K and RALGDS, to activate the downstream signal cascade. On the other hand, the active RAS is converted to the inactive type by replacement of GTP with GDP due to the intrinsic GTP hydrolysis (GTPase) activity. The GTPase activity is enhanced by a GTPase-activating protein (GAP). As can be seen from the above statement, RAS bears an important function of “molecular switch” in an intracellular signal transduction pathway for EGFR or the like and plays a critical role in the processes of cell growth, proliferation, angiogenesis and the like (Nature Rev. Cancer, 2011, 11, p. 761-774, Nature Rev. Drug Discov., 2014, 13, p. 828-851, Nature Rev. Drug Discov., 2016, 15, p. 771-785).

Substitution of an amino acid by spontaneous mutation of the RAS gene results in a constant activated state due to hypofunction of RAS as GTPase or hyporeactivity to GAP, and then, signals are continuously transmitted to downstream. The excessive signaling causes carcinogenesis or cancer growth acceleration. It is said that pancreatic ductal adenocarcinoma occurs through a weakly heteromorphic stage and a subsequent highly heteromorphic stage in the pancreatic intraepithelial neoplasia (PanIN), and mutation of the KRAS gene has already been recognized in an initial stage of PanIN. Subsequently, abnormality occurs in INK4A, p53 and SMAD4, which are tumor suppression genes, leading to malignancy (Nature Rev. Cancer, 2010, 10, p. 683-695). Furthermore, in 90% or more of the cases of pancreatic ductal adenocarcinoma, mutation is seen in the KRAS gene, and a majority of them are a spontaneous point mutation in the codon 12 located in the KRAS exon 2 (Cancer Cell 2017, 32, p. 185-203). As can be seen from the above statement, KRAS plays a critical role in the processes of carcinogenesis and development of pancreatic cancer.

In recent years, the existence of an allosteric pocket in the vicinity of a region called switch II is shown (Nature, 2013, 503, p. 548-551) against G12C mutant KRAS. Several compounds which irreversibly bind to the G12C mutant KRAS by forming a covalent bond to a cysteine of the G12C mutant KRAS have been reported (Cancer Discov., 2016, 6, p. 316-329, Cell, 2018, 172, p. 578-589, Nature, 2019, 575, p. 217-223). A G12C mutant KRAS selective inhibitor inhibits conversion from the inactive type to the active type by covalently binding to the G12C mutant KRAS and induces cancer cell death by blocking a downstream signal.

The G12C mutant KRAS frequently occurs in non-small-cell lung cancer but occurs few percent in pancreatic cancer (Cancer Cell 2014, 25, p. 272-281), and a therapeutic agent against another KRAS mutation is desired. G12D mutant KRAS is seen in about 34% of the cases of pancreatic cancer, and this rate is reported to be the highest in KRAS mutations (Nat. Rev. Cancer, 2018, 18, p. 767-777).

PTL 1, 2 and 3 disclose RAS inhibitors, and PTL 2 and 3 disclose compounds represented by the following formulae (A) and (B), respectively. PTL 1, 2 and 3 state that the inhibitors are useful for a cancer with a mutation in the codon 12 of KRAS. The G12D mutation is one of such mutations, but any effect on the KRAS G12D mutant cancer is not disclosed.

[Chemical Formula 1]

(A)

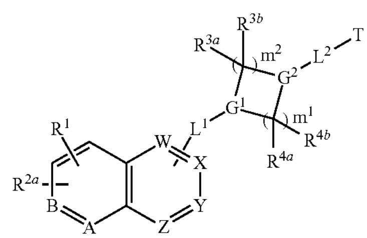

-continued (B)

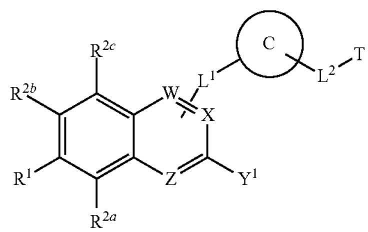

(See the publications for the meanings of the symbols in the formulae)

PTL 4, 5 and 6 disclose KRAS G12D inhibitors.

CITATION LIST

Patent Literature

PTL 1: WO2016/049565
PTL 2: WO2016/049568
PTL 3: WO2017/172979
PTL 4: WO2021/041671
PTL 5: WO2021/106231
PTL 6: WO2021/107160

SUMMARY OF INVENTION

Technical Problem

A pharmaceutical composition, for example, a compound that is expected to be useful as a G12D mutant KRAS inhibitor and to be useful as an active ingredient of a pharmaceutical composition for treating pancreatic cancer, in particular, KRAS G12D mutant-positive pancreatic cancer, is provided.

Solution to Problem

The present inventors have intensively and extensively studied about a compound that is useful as an active ingredient of a pharmaceutical composition for treating pancreatic cancer. As a result, the present inventors have found that a 4-aminoquinazoline compound of the formula (I) has an excellent G12D mutant KRAS inhibition activity, thus completing the present invention.

Specifically, the present invention relates to a compound of the formula (I) or a salt thereof and a pharmaceutical composition that contains a compound of the formula (I) or a salt thereof and an excipient.

[Chemical Formula 2]

(I)

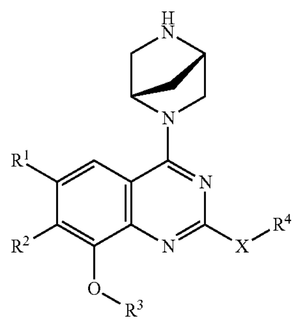

(In the formula, $R^1$ is $C_{1-3}$ alkyl optionally substituted with a group selected from the group consisting of F and $OCH_3$, halogen, cyclopropyl or $C_{2-3}$ alkenyl, $R^2$ is naphthyl optionally substituted with OH or a group selected from the group consisting of the formula (IIa) and the formula (IIb) below,

[Chemical Formula 3]

(IIa)

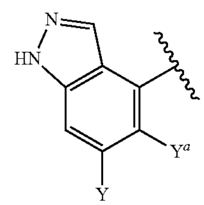

(IIb)

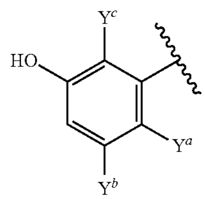

$R^3$ is the formula (III) below,

[Chemical Formula 4]

(III)

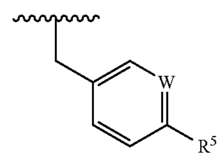

$R^4$ is optionally substituted $C_{1-6}$ alkyl, optionally substituted $C_{3-6}$ cycloalkyl, an optionally substituted 4-membered to 7-membered saturated heterocyclic group, optionally substituted 6-membered heteroaryl or tetrahydroisoquinolinyl, $R^5$ is H, $CONR^6R^7$ or a group selected from the group consisting of the formulae (IV), (V), (VI), (VII), (VIII), (IX), (X), (XI), (XII), (XIII), (XIV) and (XV) below,

[Chemical Formula 5]

(IV)

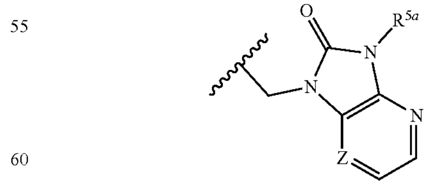

(V)

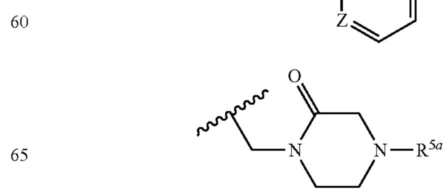

-continued (VI)

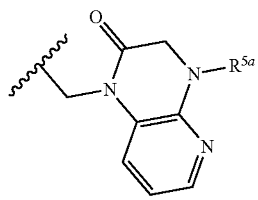

(VII)

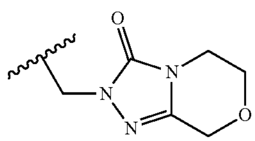

(VIII)

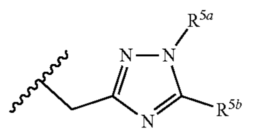

(IX)

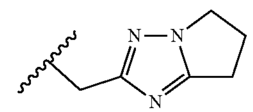

(X)

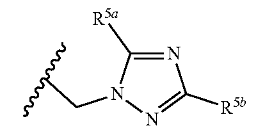

(XI)

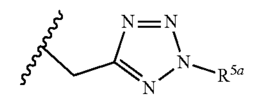

(XII)

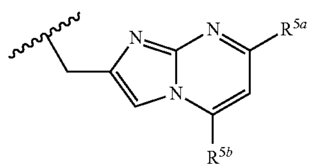

(XIII)

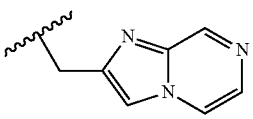

(XIV)

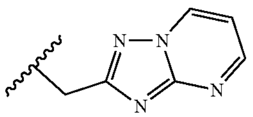

(XV)

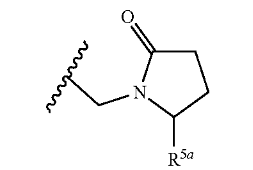

wherein $R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$, together with the nitrogen to which they are attached, may form a 4-membered to 7-membered saturated heterocyclic ring, wherein the 4-membered to 7-membered saturated heterocyclic ring is optionally substituted with optionally substituted $C_{1-6}$ alkyl, W is CH or N, X is O or $NR^x$, wherein $R^x$ is H or $C_{1-3}$ alkyl, or X—$R^4$ is a 4-membered to 7-membered saturated heterocyclic group or imidazolyl, Y and $Y^b$ are H, F or Cl, $Y^a$ is $C_{1-3}$ alkyl optionally substituted with F, cyano or cyclopropyl, or $Y^a$ and $Y^b$, together with the carbon to which they are attached, form cyclopentenyl, $Y^c$ is H, F or methyl, and Z is N or CH.)

Furthermore, an aspect of the present invention relates to the compound of the formula (I) or a salt thereof and a pharmaceutical composition that contains the compound of the formula (I) or a salt thereof and one or more pharmaceutically acceptable excipients.

[Chemical Formula 6]

(I)

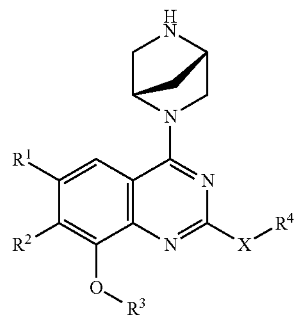

(In the formula, $R^1$ is cyclopropyl, $R^2$ is the formula (IIc) below,

[Chemical Formula 7]

(IIc)

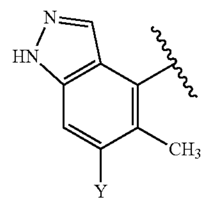

$R^3$ is the formula (IIIa) below,

[Chemical Formula 8]

(IIIa)

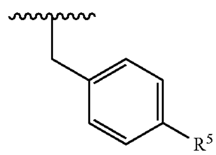

$R^4$ is tetrahydropyranyl, optionally substituted pyridylmethyl or tetrahydroisoquinolinyl, $R^5$ is a group selected from the group consisting of the formulae (IV), (V), (VI), (VII), (VIII), (IX), (X), (XI), (XII), (XIII) and (XIV) below,

[Chemical Formula 9]

(IV)

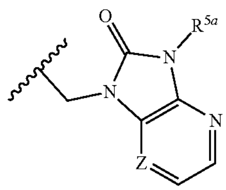

(V)

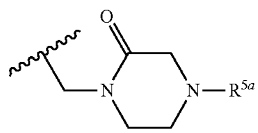

(VI)

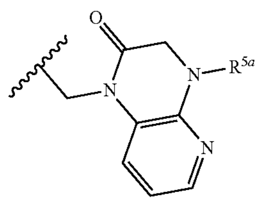

(VII)

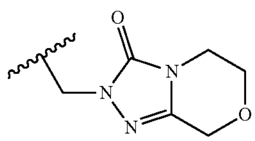

(VIII)

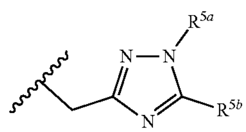

(IX)

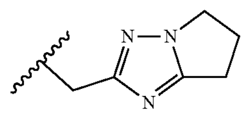

(X)

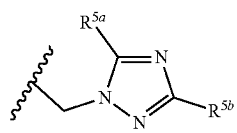

-continued (XI)

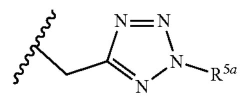

(XII)

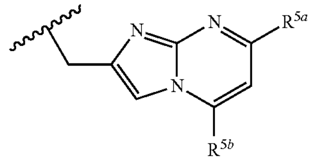

(XIII)

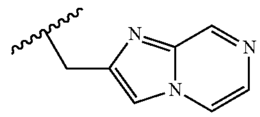

(XIV)

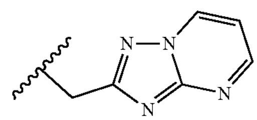

wherein $R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, thiazolyl or pyrazinyl, X is O, Y is F, and Z is N or CH.)

Note that, when a sign in a chemical formula in this specification is used in another chemical formula, the same sign represents the same meaning unless otherwise specified.

The present invention relates to a pharmaceutical composition comprising the compound of the formula (I) or a salt thereof and pharmaceutically acceptable excipients, in particular, a pharmaceutical composition for treating pancreatic cancer, in particular, a pharmaceutical composition for treating KRAS G12D mutant-positive pancreatic cancer. The pharmaceutical composition includes a therapeutic agent for pancreatic cancer, in particular, KRAS G12D mutant-positive pancreatic cancer, comprising the compound of the formula (I) or a salt thereof.

The present invention relates to use of the compound of the formula (I) or a salt thereof for the manufacture of a pharmaceutical composition for treating pancreatic cancer, in particular, KRAS G12D mutant-positive pancreatic cancer, to use of the compound of the formula (I) or a salt thereof for treating pancreatic cancer, in particular, KRAS G12D mutant-positive pancreatic cancer, to the compound of the formula (I) or a salt thereof for use in treatment of pancreatic cancer, in particular, KRAS G12D mutant-positive pancreatic cancer, and to a method for treating pancreatic cancer, in particular, KRAS G12D mutant-positive pancreatic cancer, including administering an effective amount of the compound of the formula (I) or a salt thereof to a subject.

The present invention also relates to the compound of the formula (I) or a salt thereof which is a G12D mutant KRAS inhibitor, to the compound of the formula (I) or a salt thereof for use as a G12D mutant KRAS inhibitor and to a G12D mutant KRAS inhibitor comprising the compound of the formula (I) or a salt thereof.

Note that the "subject" is a human or another animal that needs the treatment, and an aspect thereof is a human who needs the prevention or treatment.

Advantageous Effects of Invention

The compound of the formula (I) or a salt thereof has a G12D mutant KRAS inhibition activity and can be used as a therapeutic agent for pancreatic cancer.

DESCRIPTION OF EMBODIMENTS

The present invention will be explained in detail below.

In this specification, "optionally substituted" means being unsubstituted or having one to five substituents. In an aspect, the term means being unsubstituted or having one to three substituents. Note that when there are multiple substituents, the substituents may be the same as or different from each other.

The "$C_{1-12}$ alkyl" is linear or branched alkyl having 1 to 12 carbon atoms, and examples thereof include methyl, ethyl, n-propyl, isopropyl, n-butyl, isobutyl, sec-butyl, tert-butyl, n-pentyl, n-hexyl, dodecyl and the like (the numbers of carbon atoms are described similarly below). An aspect thereof is ethyl or dodecyl; another aspect is $C_{1-6}$ alkyl; another aspect is methyl, ethyl, n-propyl, isopropyl, n-butyl, isobutyl, sec-butyl, tert-butyl, n-pentyl, isopentyl, sec-pentyl or n-hexyl; and another aspect is methyl, ethyl, n-propyl, isopropyl, n-butyl, sec-butyl or isopentyl. An aspect thereof is $C_{1-3}$ alkyl; another aspect is methyl, ethyl or isopropyl; another aspect is methyl or ethyl; another aspect is methyl or isopropyl; another aspect is ethyl or isopropyl; another aspect is methyl; another aspect is ethyl; and another aspect is isopropyl.

The "$C_{2-3}$ alkenyl" is alkenyl having two to three carbon atoms, and examples thereof include vinyl and propenyl. An aspect thereof is vinyl, 1-propenyl or 2-propenyl. Another aspect is vinyl.

The "$C_{3-6}$ cycloalkyl" is cycloalkyl having three to six carbon atoms, and examples thereof include cyclopropyl, cyclobutyl, cyclopentyl and cyclohexyl. An aspect thereof is cyclopropyl, cyclobutyl or cyclohexyl; another aspect is cyclopropyl or cyclobutyl; another aspect is cyclopropyl; and another aspect is cyclobutyl.

The "4-membered to 7-membered saturated heterocyclic group" is, for example, a 4-membered to 7-membered saturated heterocyclic group containing one or two hetero atoms selected from the group consisting of oxygen, sulfur and nitrogen as ring-constituting atoms and may form a bridged ring or may form a spiro ring. Furthermore, the sulfur atom contained in the heterocyclic group may be oxidized. An aspect thereof is oxetanyl, tetrahydrofuranyl, tetrahydropyranyl, azetidinyl, pyrrolidinyl, piperidinyl, azepanyl, oxazolidinyl, imidazolidinyl, piperazinyl, morpholinyl, thiomorpholinyl, dioxothiomorpholinyl, azabicyclo[2.2.1]heptanyl, diazabicyclo[2.2.1]heptanyl, azaspiro[3.3]heptanyl, oxazaspiro[3.3]heptanyl or thiazaspiro[3.3]heptanyl; another aspect is oxetanyl, tetrahydrofuranyl, tetrahydropyranyl, azetidinyl, pyrrolidinyl, piperidinyl, piperazinyl, morpholinyl, thiomorpholinyl, dioxothiomorpholinyl, azaspiro[3.3]heptanyl or oxazaspiro[3.3]heptanyl; another aspect is azetidinyl, tetrahydropyranyl, morpholinyl or oxazaspiro[3.3]heptanyl; another aspect is azetidinyl or tetrahydropyranyl, another aspect is morpholinyl or oxazaspiro[3.3]heptanyl; and another aspect is tetrahydropyranyl.

The "6-membered heteroaryl" is, for example, heteroaryl of a 6-membered ring containing one to three nitrogen atoms as ring-constituting atoms. An aspect of the "6-membered heteroaryl" is pyridyl, pyrimidinyl, pyrazinyl, pyridazinyl or triazinyl; another aspect is pyridyl or pyrimidinyl; and another aspect is pyrimidinyl.

The "halogen" means F, Cl, Br and I. An aspect thereof is F, Cl or Br; another aspect is F or Cl; another aspect is F; another aspect is Cl; and another aspect is Br.

An aspect of the substituent acceptable in the "optionally substituted pyridyl", "optionally substituted oxazolyl" and "optionally substituted pyridylmethyl" is $C_{1-3}$ alkyl; another aspect is methyl or isopropyl; another aspect is methyl; and another aspect is isopropyl.

An aspect of the substituent acceptable in the "optionally substituted $C_{1-6}$ alkyl" and the "optionally substituted $C_{1-3}$ alkyl" is halogen, OH, $OCH_3$, cyano, $C_{1-3}$ alkyl, hydroxymethyl, methoxymethyl, cyanomethyl, difluoroethyl, optionally substituted $C_{3-6}$ cycloalkyl, optionally substituted pyridyl or optionally substituted 4-membered to 7-membered saturated heterocyclic group; another aspect is halogen, $OCH_3$, cyano, optionally substituted $C_{3-6}$ cycloalkyl, optionally substituted pyridyl or optionally substituted 4-membered to 7-membered saturated heterocyclic group; another aspect is F, $OCH_3$, cyano, optionally substituted $C_{3-6}$ cycloalkyl, optionally substituted pyridyl or optionally substituted 4-membered to 7-membered saturated heterocyclic group; another aspect is F, $OCH_3$ or cyano; another aspect is halogen or $OCH_3$; another aspect is F or $OCH_3$; and another aspect is halogen.

An aspect of the substituent acceptable in the "optionally substituted $C_{3-6}$ cycloalkyl" is halogen, $OCH_3$ or $C_{1-3}$ alkyl optionally substituted with $OCH_3$; another aspect is F, $OCH_3$ or $C_{1-3}$ alkyl optionally substituted with $OCH_3$; another aspect is $C_{1-3}$ alkyl optionally substituted with $OCH_3$; and another aspect is F, $OCH_3$ or methoxymethyl.

An aspect of the substituent acceptable in the "4-membered to 7-membered saturated heterocyclic group" is OH, $OCH_3$ or $C_{1-3}$ alkyl optionally substituted with a group selected from the group consisting of F, $OCH_3$ and cyano; and another aspect is OH, $OCH_3$, trifluoromethyl, difluoromethyl, methoxyethyl or cyanomethyl.

An aspect of the substituent acceptable in the "optionally substituted 6-membered heteroaryl" is $C_{1-3}$ alkyl or $N(CH_3)_2$, and another aspect is ethyl or $N(CH_3)_2$.

The "G12D mutation" represents a mutation in which the amino acid residue corresponding to the codon 12 in a wild type protein is converted from glycine to aspartic acid.

The "G12D mutant KRAS" represents KRAS having the "G12D mutation".

The "pancreatic cancer" is a malignant tumor occurring in the pancreas. Examples thereof include pancreatic ductal carcinoma and pancreatic ductal adenocarcinoma. An aspect thereof is pancreatic ductal carcinoma, and another aspect is pancreatic ductal adenocarcinoma.

The "KRAS G12D mutant-positive pancreatic cancer" is pancreatic cancer that is positive for G12D mutant KRAS, and examples thereof include pancreatic cancer having KRAS G12D mutation and pancreatic cancer which has a high positive rate for G12D mutant KRAS. An aspect thereof is KRAS G12D mutant-positive pancreatic ductal carcinoma and KRAS G12D mutant-positive pancreatic ductal adenocarcinoma; another aspect is KRAS G12D mutant-positive pancreatic ductal carcinoma; and another aspect is KRAS G12D mutant-positive pancreatic ductal adenocarcinoma.

Aspects of the compound of the formula (I) or a salt thereof in the present invention are shown below.

(1-1)

The compound or a salt thereof in which $R^1$ is $C_{1-3}$ alkyl optionally substituted with a group selected from the group consisting of F and $OCH_3$, halogen, cyclopropyl or $C_{2-3}$ alkenyl.

(1-2)

The compound or a salt thereof in which $R^1$ is cyclopropyl.

(2-1)

The compound or a salt thereof in which $R^2$ is naphthyl optionally substituted with OH or a group selected from the group consisting of the formula (IIa) and the formula (IIb) below,

[Chemical Formula 10]

(IIa)

(IIb)

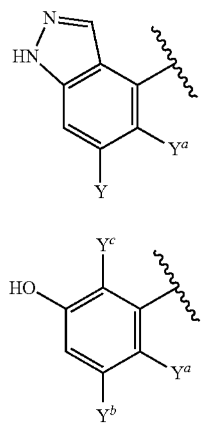

where Y and $Y^b$ are H, F or Cl, $Y^a$ is $C_{1-3}$ alkyl optionally substituted with F, cyano or cyclopropyl, or $Y^a$ and $Y^b$, together with the carbon to which they are attached, form cyclopentenyl, and $Y^c$ is H, F or methyl.

(2-2)

The compound or a salt thereof in which $R^2$ is the formula (IIc) below,

[Chemical Formula 11]

(IIc)

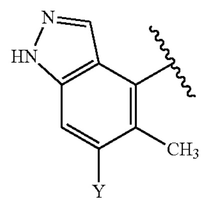

where Y is F.

(3-1)

The compound or a salt thereof in which $R^3$ is the formula (III) below,

[Chemical Formula 12]

(III)

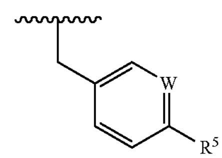

where W is CH or N.

(3-2)

The compound or a salt thereof in which $R^3$ is the formula (IIIa) below.

[Chemical Formula 13]

(IIIa)

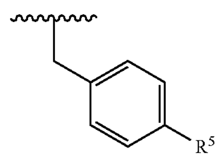

(4-1)

The compound or a salt thereof in which $R^4$ is optionally substituted $C_{1-6}$ alkyl, optionally substituted $C_{3-6}$ cycloalkyl, optionally substituted 4-membered to 7-membered saturated heterocyclic group, optionally substituted 6-membered heteroaryl or tetrahydroisoquinolinyl, X is O or $NR^x$, where $R^x$ is H or $C_{1-3}$ alkyl, or X—$R^4$ is a 4-membered to 7-membered saturated heterocyclic group or imidazolyl.

(4-2)

The compound or a salt thereof in which $R^4$ is $C_{1-6}$ alkyl, where the $C_{1-6}$ alkyl is optionally substituted with a group selected from the group consisting of F; $OCH_3$; cyclopropyl optionally substituted with $OCH_3$; cyclobutyl optionally substituted with a group selected from the group consisting of F and methoxymethyl; oxetanyl optionally substituted with $OCH_3$; tetrahydrofuranyl; tetrahydropyranyl optionally substituted with a group selected from the group consisting of OH, $CF_3$ and cyanomethyl; and pyridyl optionally substituted with $C_{1-3}$ alkyl, $C_{3-6}$ cycloalkyl optionally substituted with $OCH_3$, azetidinyl optionally substituted with F, tetrahydropyranyl, pyrimidinyl optionally substituted with a group selected from the group consisting of $C_{1-3}$ alkyl and $N(CH_3)_2$ or tetrahydroisoquinolinyl, X is O or $NR^x$, where $R^x$ is H or $C_{1-3}$ alkyl, or X—$R^4$ is a morpholinyl, oxazaspiro[3.3]heptanyl or imidazolyl.

(4-3)

The compound or a salt thereof in which $R^4$ is tetrahydropyranyl, optionally substituted pyridylmethyl, or tetrahydroisoquinolinyl, and X is O.

(4-4)

The compound or a salt thereof in which $R^4$ is tetrahydropyranyl, and

X is O.

(5-1)

The compound or a salt thereof in which $R^5$ in the formula (III) is H, $CONR^6R^7$ or a group selected from the group consisting of the formulae (IV), (V), (VI), (VII), (VIII), (IX), (X), (XI), (XII), (XIII), (XIV) and (XV) below,

[Chemical Formula 14]

(IV)

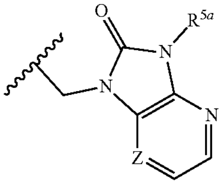

(V)

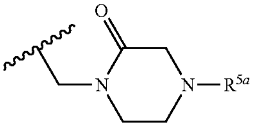

(VI)

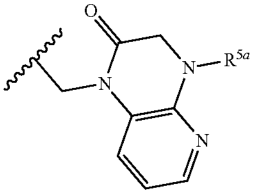

(VII)

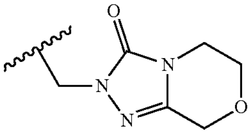

(VIII)

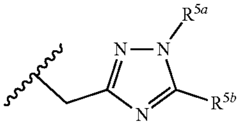

(IX)

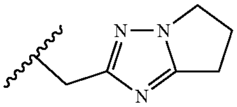

(X)

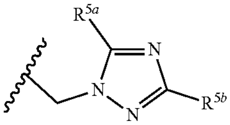

(XI)

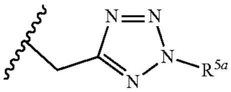

-continued (XII)

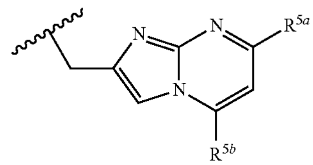

(XIII)

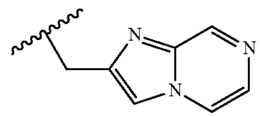

(XIV)

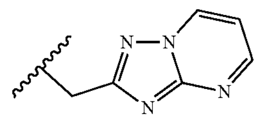

(XV)

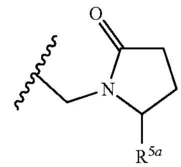

where $R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$, together with the nitrogen to which they are attached, may form a 4-membered to 7-membered saturated heterocyclic ring, where the 4-membered to 7-membered saturated heterocyclic ring is optionally substituted with optionally substituted Ci-6 alkyl, and Z is N or CH.

(5-2)

The compound or a salt thereof in which $R^5$ in the formula (III) is H, $CONR^6R^7$ or a group selected from the group consisting of the formulae (IV), (V), (VI), (VII), (VIII), (IX), (X), (XI), (XII), (XIII), (XIV) and (XV), where $R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$, together with the nitrogen to which they are attached, may form morpholinyl or piperazinyl, where the piperazinyl is optionally substituted with optionally substituted $C_{1-6}$ alkyl, and Z is N or CH.

(5-3)

The compound or a salt thereof in which $R^5$ in the formula (III) is H, $CONR^6R^7$ or a group selected from the group consisting of the formulae (IV), (V), (VI), (VII), (VIII), (IX), (X), (XI), (XII), (XIII), (XIV) and (XV), where $R^{5a}$ and $R^{5b}$, which are the same as or different from each other, are H, $C_{1-3}$ alkyl optionally substituted with F, cyclopropyl, cyclopropylmethyl, oxetanyl, tetrahydropyranyl, oxazolyl optionally substituted with $C_{1-3}$ alkyl, thiazolyl or pyrazinyl, $R^6$ and $R^7$, which are the same as or different from each other, are H or $C_{1-6}$ alkyl, or $R^6$ and $R^7$, together with the nitrogen to which they are attached, may form morpholinyl or piperazinyl, where the piperazinyl is optionally substituted with methoxyethyl, and Z is N or CH.

(5-4)

The compound or a salt thereof in which $R^5$ in the formula (IIIa) is a group selected from the group consisting of the formulae (IV), (V), (VI), (VII), (VIII), (IX), (X), (XI), (XII), (XIII) and (XIV) below,

[Chemical Formula 15]

(IV)

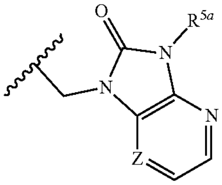

(V)

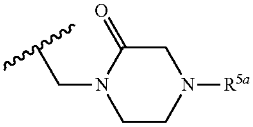

(VI)

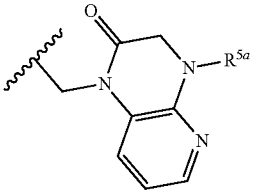

(VII)

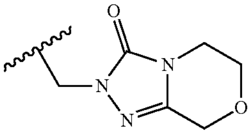

(VIII)

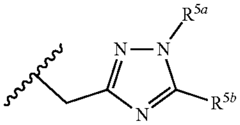

(IX)

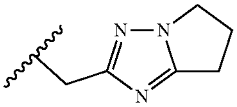

(X)

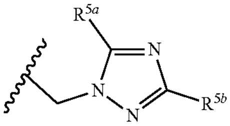

(XI)

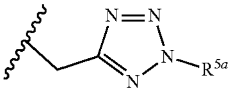

-continued (XII)

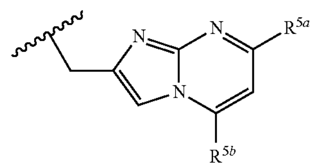

(XIII)

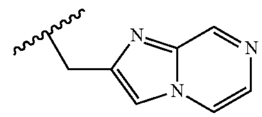

(XIV)

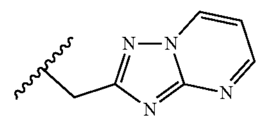

where $R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, thiazolyl or pyrazinyl, and Z is N or CH.

(5-5)

The compound or a salt thereof in which $R^5$ in the formula (IIIa) is a group selected from the group consisting of the formulae (IV), (V), (VI), (VII), (VIII), (IX), (X), (XI), (XII), (XIII) and (XIV), where $R^{5a}$ and $R^{5b}$, which are the same as or different from each other, are H, $C_{1-3}$ alkyl optionally substituted with F, cyclopropyl, cyclopropylmethyl, oxetanyl, tetrahydropyranyl, thiazolyl or pyrazinyl, and Z is N or CH.

(6)

The compound or a salt thereof in which $R^4$ is tetrahydropyranyl, optionally substituted pyridylmethyl or tetrahydroisoquinolinyl. An aspect thereof is the compound or a salt thereof in which $R^4$ is tetrahydropyranyl. Another aspect is the compound or a salt thereof in which $R^4$ is optionally substituted pyridylmethyl. Another aspect is the compound or a salt thereof in which $R^4$ is tetrahydroisoquinolinyl.

(7)

The compound or a salt thereof in which $R^5$ in the formula (III) is a group selected from the group consisting of the formulae (IV), (V), (VI), (VII), (VIII), (IX), (X), (XI), (XII), (XIII) and (XIV). An aspect thereof is the compound or a salt thereof in which $R^5$ is the formula (IV). Another aspect is the compound or a salt thereof in which $R^5$ is the formula (V). Another aspect is the compound or a salt thereof in which $R^5$ is the formula (VI). Another aspect is the compound or a salt thereof in which $R^5$ is the formula (VII). Another aspect is the compound or a salt thereof in which $R^5$ is the formula (VIII). Another aspect is the compound or a salt thereof in which $R^5$ is the formula (IX). Another aspect is the compound or a salt thereof in which $R^5$ is the formula (X). Another aspect is the compound or a salt thereof in which $R^5$ is the formula (XI). Another aspect is the compound or a salt thereof in which $R^5$ is the formula (XII). Another aspect is the compound or a salt thereof in which $R^5$ is the formula (XIII). Another aspect is the compound or a salt thereof in which $R^5$ is the formula (XIV).

(8)

The compound or a salt thereof in which $R^{5a}$ and $R^{5b}$, which are the same as or different from each other, are optionally substituted $C_{1-3}$ alkyl, cyclopropyl, cyclopropylmethyl, oxetanyl, tetrahydropyranyl, thiazolyl or pyrazinyl. An aspect thereof is the compound or a salt thereof in which $R^{5a}$ and $R^{5b}$, which are the same as or different from each other, are optionally substituted $C_{1-3}$ alkyl. Another aspect is the compound or a salt thereof in which $R^{5a}$ and $R^{5b}$, which are the same as or different from each other, are cyclopropyl. Another aspect is the compound or a salt thereof in which $R^{5a}$ and $R^{5b}$, which are the same as or different from each other, are cyclopropylmethyl. Another aspect is the compound or a salt thereof in which $R^{5a}$ and $R^{5b}$, which are the same as or different from each other, are oxetanyl. Another aspect is the compound or a salt thereof in which $R^{5a}$ and $R^{5b}$ which are the same as or different from each other, are tetrahydropyranyl. Another aspect is the compound or a salt thereof in which $R^{5a}$ and $R^{5b}$, which are the same as or different from each other, are thiazolyl. Another aspect is the compound or a salt thereof in which $R^{5a}$ and $R^{5b}$, which are the same as or different from each other, are pyrazinyl.

(9)

The compound or a salt thereof which is a combination of any compatible two or more of the aspects described in (1-1) to (8) above.

Specific examples of the combination described in (9) above include the aspects below.

(10-1)

The compound or a salt thereof which is a combination of the aspects of (1-1), (2-1), (3-1), (4-1) and (5-1) above.

(10-2)

The compound or a salt thereof which is a combination of the aspects of (1-1), (2-1), (3-1), (4-2) and (5-2) above.

(10-3)

The compound or a salt thereof which is a combination of the aspects of (1-2), (2-2), (3-2), (4-3) and (5-4) above.

(10-4)

The compound or a salt thereof which is a combination of the aspects of (1-2), (2-2), (3-2), (4-4) and (5-5) above.

Examples of specific compounds included in the present invention as an aspect include the following compounds:

1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-3-methyl-1,3-dihydro-2H-imidazo[4,5-b]pyrazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-methylpiperazin-2-one, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-[(4-{[1-(oxetan-3-yl)-1H-1,2,4-triazol-3-yl]methyl}phenyl)methoxy]quinazoline, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-ethylpiperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(oxan-4-yl)piperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(propan-2-yl)piperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(cyclopropylmethyl)piperazin-2-one, 1-[(4-{[(6-cyclopropyl-4-[(1S,4S)-2,5-diazabicyclo[2.2.1]heptan-2-yl]-7-(6-fluoro-5-methyl-1H-indazol-4-yl)-2-{[(5R)-5,6,7,8-tetrahydroisoquinolin-5-yl]oxy}quinazolin-8-yl)oxy]methyl}phenyl)methyl]-3-methyl-1,3-dihydro-2H-imidazo[4,5-b]pyridin-2-one, 6-cyclopropyl-4-[(1S,4S)-2,5-diazabicyclo[2.2.1]heptan-2-yl]-8-({4-[(5,7-dimethylimidazo[1,2-a]pyrimidin-2-yl)methyl]phenyl}methoxy)-7-(6-fluoro-5-methyl-1H-indazol-4-yl)-2-[(oxan-4-yl)oxy]quinazoline, 1-[(4-{[(6-cyclopropyl-4-[(1S,4S)-2,5-diazabicyclo[2.2.1]heptan-2-yl]-7-(6-fluoro-5-methyl-1H-indazol-4-yl)-2-{[2-(propan-2-yl)pyridin-3-yl]methoxy}quinazolin-8-yl)oxy]methyl}phenyl)methyl]-3-methyl-1,3-dihydro-2H-imidazo[4,5-b]pyridin-2-one, 6-cyclopropyl-4-[(1S,4S)-2,5-diazabicyclo[2.2.1]heptan-2-yl]-7-(6-fluoro-5-methyl-1H-indazol-4-yl)-8-[(4-{[5-methyl-3-(pyrazin-2-yl)-1H-1,2,4-triazol-1-yl]methyl}phenyl)methoxy]-2-[(oxan-4-yl)oxy]quinazoline, 2-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-2,5,6,8-tetrahydro-3H-[1,2,4]triazolo[3,4-c][1,4]oxazin-3-one, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-({4-[([1,2,4]triazolo[1,5-a]pyrimidin-2-yl)methyl]phenyl}methoxy)quinazoline, 6-cyclopropyl-8-({4-[(1-cyclopropyl-1H-1,2,4-triazol-3-yl)methyl]phenyl}methoxy)-4-[(1 S,4S)-2,5-diazabicyclo[2.2.1]heptan-2-yl]-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-8-({4-[(5-ethyl-1-methyl-1H-1,2,4-triazol-3-yl)methyl]phenyl}methoxy)-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-({4-[(2-methyl-2H-tetrazol-5-yl)methyl]phenyl}methoxy)-2-[(oxan-4-yl)oxy]quinazoline, 6-cyclopropyl-4-[(1S,4S)-2,5-diazabicyclo[2.2.1]heptan-2-yl]-8-[(4-{[5-(difluoromethyl)-1-methyl-1H-1,2,4-triazol-3-yl]methyl}phenyl)methoxy]-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-8-({4-[(6,7-dihydro-5H-pyrrolo[1,2-b][1,2,4]triazol-2-yl)methyl]phenyl}methoxy)-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-[(4-{[1-(oxan-4-yl)-1H-1,2,4-triazol-3-yl]methyl}phenyl)methoxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-({4-[(imidazo[1,2-a]pyrazin-2-yl)methyl]phenyl}methoxy)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-[(4-{[1-methyl-5-(1,3-thiazol-2-yl)-1H-1,2,4-triazol-3-yl]methyl}phenyl)methoxy]-2-[(oxan-4-yl)oxy]quinazoline, 6-cyclopropyl-8-({4-[(5-cyclopropyl-1-methyl-1H-1,2,4-triazol-3-yl)methyl]phenyl}methoxy)-4-[(1 S,4S)-2,5-diazabicyclo[2.2.1]heptan-2-yl]-7-(6-fluoro-5-methyl-1H-indazol-4-yl)-2-[(oxan-4-yl)oxy]quinazoline and 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]

phenyl}methyl)-4-methyl-3,4-dihydropyrido[2,3-b]pyrazin-2(1H)-one, and a salt thereof.

The compound of the formula (I) may have tautomers or geometrical isomers depending on the type of the substituent. In this specification, the compound of the formula (I) is sometimes described only as one of isomers, but the present invention includes isomers other than the above one and includes separated isomers or mixtures thereof.

In addition, the compound of the formula (I) may have an asymmetric carbon atom or an axial chirality and may have diastereomers based on them. The present invention includes separated diastereomers of the compound of the formula (I) or mixtures thereof.

Furthermore, the present invention also includes pharmaceutically acceptable prodrugs of the compound represented by the formula (I). A pharmaceutically acceptable prodrug is a compound having a group that can be converted into an amino group, a hydroxy group, a carboxyl group or the like by solvolysis or under physiological conditions. Examples of groups to form a prodrug include groups described in Prog. Med., 1985, 5, p. 2157-2161 or in "Iyakuhin no Kaihatsu (development of pharmaceuticals)", Vol. 7, Bunshi-sekkei (molecular design), Hirokawa Shoten, 1990, p. 163-198.

In addition, the salt of the compound of the formula (I) is a pharmaceutically acceptable salt of the compound of the formula (I) and may be an acid addition salt or a salt formed with a base depending on the type of the substituent. Examples thereof include salts shown in P. Heinrich Stahl, Handbook of Pharmaceutical Salts Properties, Selection, and Use, Wiley-VCH, 2008. Specific examples include an acid addition salt with an inorganic acid, such as hydrochloric acid, hydrobromic acid, hydroiodic acid, sulfuric acid, nitric acid and phosphoric acid, or with an organic acid, such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid and glutamic acid, a salt with an inorganic metal, such as sodium, potassium, magnesium, calcium and aluminum, a salt with an organic base, such as methylamine, ethylamine and ethanolamine, a salt with various amino acids and amino acid derivatives, such as acetylleucine, lysine and omithine, an ammonium salt and the like.

Furthermore, the present invention also includes various hydrates, solvates and crystal polymorphism substances of the compound of the formula (I) and a salt thereof. The present invention also includes the compounds which are labeled with various radioactive or nonradioactive isotopes.

(Production Method)

The compound of the formula (I) and a salt thereof can be produced by applying various known synthetic methods using characteristics based on the basic structure or the type of substituent thereof. Here, depending on the type of functional group, it is sometimes effective as a production technique to substitute the functional group with an appropriate protective group (a group that can be easily converted to the functional group) in the process from a raw material to an intermediate. Examples of the protective group include protective groups described in P. G. M. Wuts and T. W. Greene, "Greene's Protective Groups in Organic Synthesis", 5th edition, John Wiley & Sons Inc., 2014 and the like, and a group appropriately selected from the protective groups is used depending on the reaction conditions. In such a method, a reaction is carried out with the protective group introduced, and then the protective group is removed, as required, whereby a desired compound can be obtained.

In addition, a prodrug of the compound of the formula (I) can be produced by introducing a special group in a process from a raw material to an intermediate as for the above protective group or by further carrying out a reaction using the compound of the formula (I) obtained. This reaction can be carried out by applying a method known to a person skilled in the art, such as common esterification, amidation and dehydration.

Typical methods for producing the compound of the formula (I) will be explained below. The production methods can also be carried out referring to a reference attached to the explanation. Note that the production method of the present invention is not limited to the examples described below.

In this specification, the following abbreviations are sometimes used.

DMF: N,N-dimethylformamide, DMA: N,N-dimethylacetamide, THF: tetrahydrofuran, MeCN: acetonitrile, MeOH: methanol, EtOH: ethanol, DOX: 1,4-dioxane, DMSO: dimethyl sulfoxide, TEA: triethylamine, DIPEA: N,N-diisopropylethylamine, tBuOK: potassium tert-butoxide, $PdCl_2(dppf)\text{-}CH_2Cl_2$: [1,1'-bis(diphenylphosphino)ferrocene]palladium(II) dichloride-dichloromethane adduct, Pd/C: palladium carbon, LAH: lithium aluminium hydride, Me: methyl group.

[Chemical Formula 16]

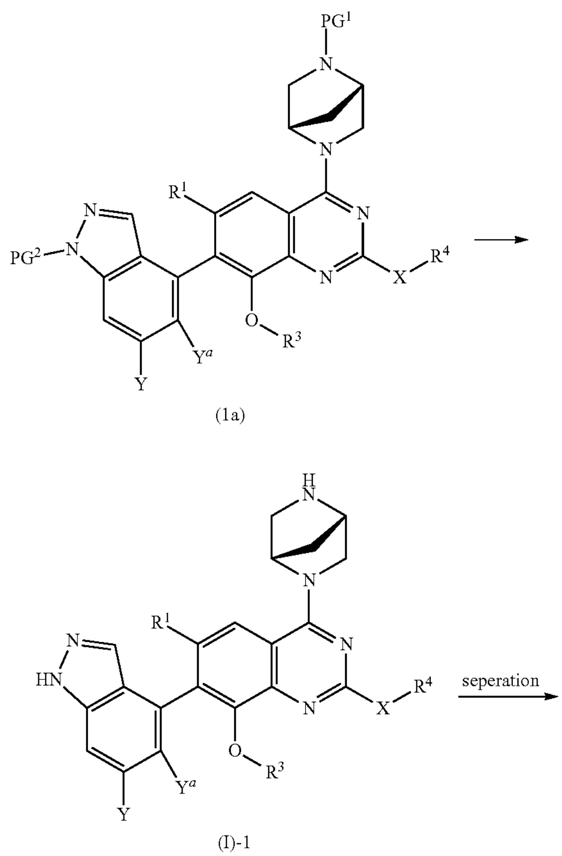

(1a)

(I)-1

-continued

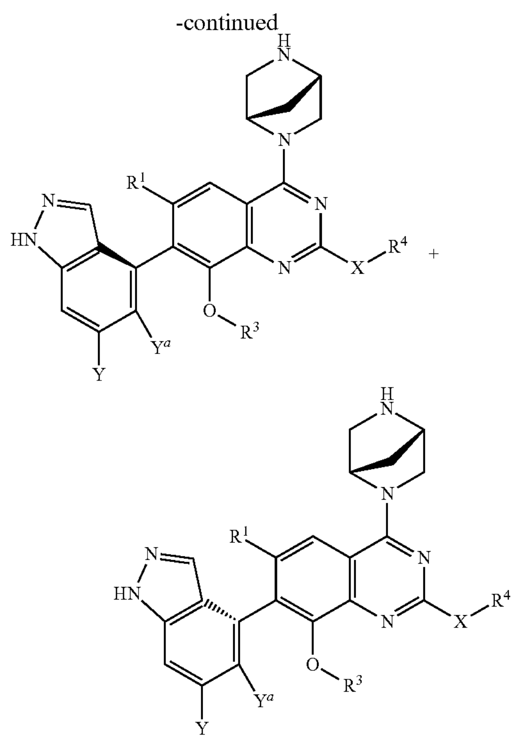

(In the formula, $PG^1$ represents a protective group, and $PG^2$ represents a protective group or a hydrogen atom.)

A compound of the formula (I)-1, which is representative of the compound of the formula (I), can be obtained by subjecting a compound (1a) to a deprotection reaction. Examples of the protective group which can be deprotected under acidic conditions here include tert-butoxycarbonyl group, a triphenylmethyl group, a tetrahydro-2H-pyran-2-yl group and the like.

This reaction is performed by stirring the compound from under cooling to under reflux with heat generally for 0.1 hours to five days. Examples of the solvent used here include, but are not particularly limited to, an alcohol, such as MeOH and EtOH, a halogenated hydrocarbon, such as dichloromethane, 1,2-dichloroethane and chloroform, an ether, such as diethyl ether, THF, DOX and dimethoxyethane, DMF, DMSO, MeCN or water and a mixture thereof. Examples of the deprotection reagent include, but are not particularly limited to, an acid, such as hydrogen chloride (DOX solution), trifluoroacetic acid and methanesulfonic acid.

By selecting a protective group, the deprotection can be performed by a catalytic hydrogenation reaction. Examples of the protective group include a benzyl group, a p-methoxybenzyl group, a benzyloxycarbonyl group and the like. The deprotection can also be performed using a fluoride ion source such as tetra-n-butylammonium fluoride. Examples of the protective group include a tert-butyl(dimethyl)silyl group, a (trimethylsilyl)ethoxymethyl group and the like. Furthermore, examples of the protective group which can be deprotected under basic conditions include an acetyl group, a trifluoroacetyl group, a benzoyl group and the like. Moreover, protective groups which can be deprotected under different deprotection conditions can be selected for $PG^1$ and $PG^2$, and the deprotection can be performed stepwise.

For example, the following can be referred as a reference about this reaction.

P. G. M. Wuts and T. W. Greene, "Greene's Protective Groups in Organic Synthesis", 5th edition, John Wiley & Sons Inc., 2014

Note that when the compound (1a) as a raw material has an axial chirality, an optically active substance which is obtained by once separating the compound (1a) may be used for this reaction.

A compound in which $R^2$ in the formula (I) is naphthyl optionally substituted with OH or the formula (IIb) can be obtained by the same production method as described above.

By subjecting the compound of the formula (I) to the following operation as a salt formation reaction, the hydrochloride of the compound of the formula (I) can be obtained.

The compound of the formula (I) which is believed to form a salt with hydrochloric acid from the characteristics of the chemical structure is dissolved in a halogenated hydrocarbon, such as dichloromethane, and an alcohol, such as MeOH, and stirred under ice cooling, generally for 0.1 hours to a day, after adding hydrogen chloride (4M DOX solution) under ice cooling. The reaction mixture is concentrated under reduced pressure, and an ether, such as diethyl ether, is added to the resulting residue. The produced solid is taken by filtration and is dried under reduced pressure, thus obtaining the hydrochloride of the compound of the formula (I).

By subjecting the hydrochloride of the compound of the formula (I) to the following operation as a desalting reaction, the compound of the formula (I) can be obtained.

The hydrochloride of the compound of the formula (I) is purified by octadecylsilyl (ODS) column chromatography (MeCN/0.1% aqueous formic acid solution), and a fraction containing the target substance is collected and is made basic with saturated aqueous sodium hydrogen carbonate solution. Then the solution is subjected to extraction with $CHCl_3$/MeOH (5/1). The combined organic layer is dried over anhydrous sodium sulfate, and the solution is concentrated under reduced pressure. The resulting solid is washed with diethyl ether and dried under reduced pressure, thus obtaining the compound of the formula (I).

(Raw Material Synthesis 1)

[Chemical Formula 17]

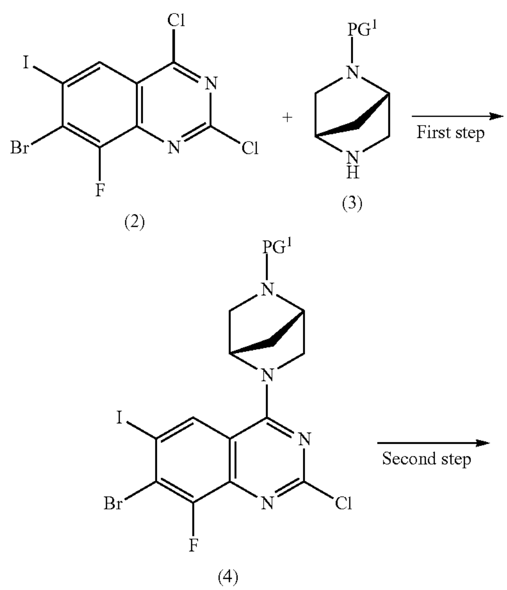

(2) (3) (4)

-continued

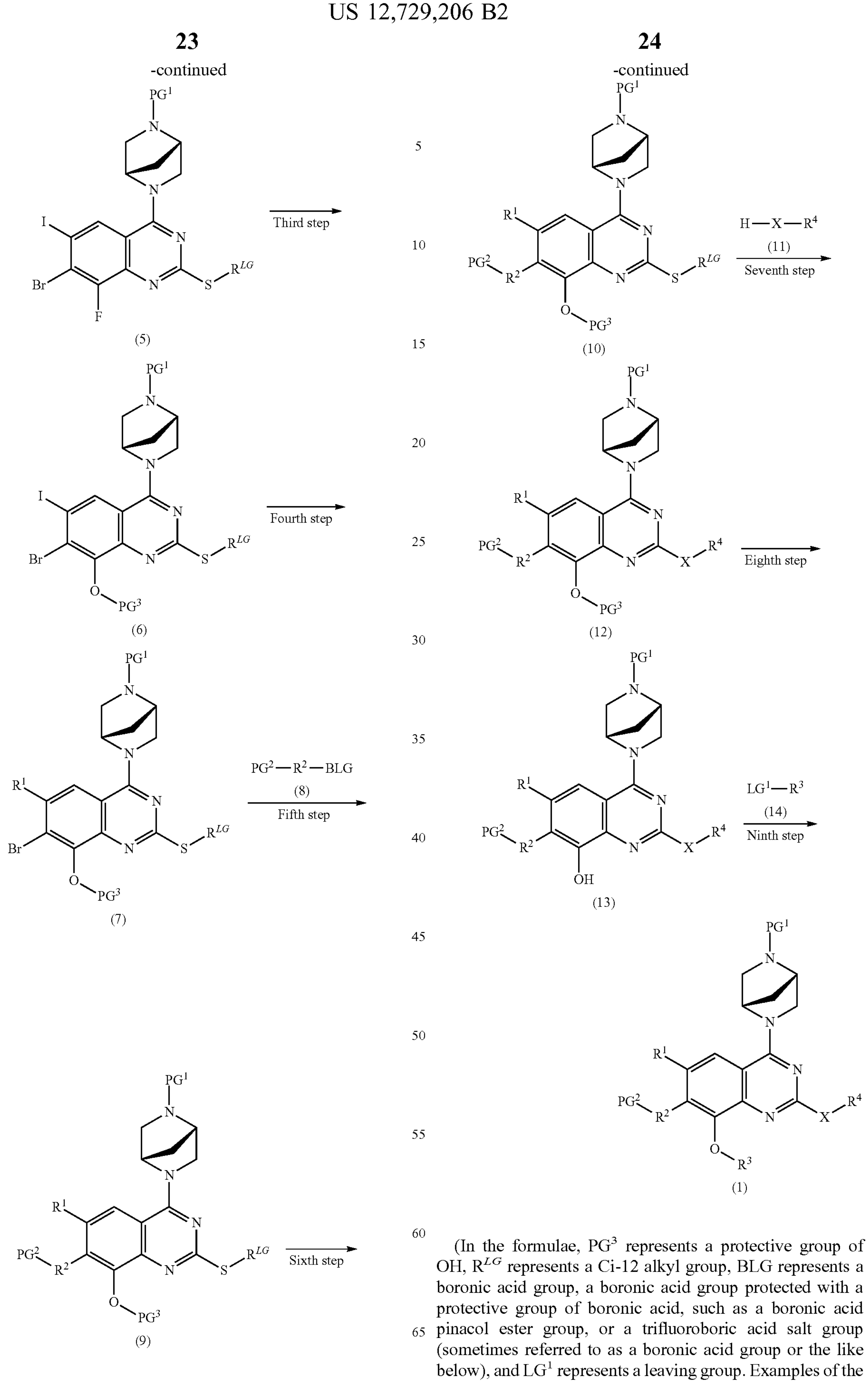

(5)

(6)

(7)

(9)

(10)

(12)

(13)

(1)

(In the formulae, $PG^3$ represents a protective group of OH, $R^{LG}$ represents a Ci-12 alkyl group, BLG represents a boronic acid group, a boronic acid group protected with a protective group of boronic acid, such as a boronic acid pinacol ester group, or a trifluoroboric acid salt group (sometimes referred to as a boronic acid group or the like below), and $LG^1$ represents a leaving group. Examples of the leaving group shown here include Cl, Br, I, a methanesulfonyl group, a p-toluenesulfonyl group and the like.)

This production method is a first method for producing a raw material compound (1).

(First Step)

This step is a method for producing a compound (4) by an ipso substitution reaction of a compound (2) and a compound (3).

In this reaction, the compound (2) and the compound (3) are used in an equal amount or with one compound thereof in an excess amount, and the mixture of the compounds is stirred in a solvent inactive for the reaction or with no solvent, from under cooling to under reflux with heat, preferably at 0° C. to 80° C., generally for 0.1 hours to five days. Examples of the solvent used here include, but are not particularly limited to, a halogenated hydrocarbon, such as dichloromethane, 1,2-dichloroethane and chloroform, an aromatic hydrocarbon, such as benzene, toluene and xylene, an ether, such as diethyl ether, THF, DOX and 1,2-dimethoxyethane, DMF, DMSO, ethyl acetate, MeCN and a mixture thereof. Performing the reaction in the presence of an organic base, such as TEA, DIPEA, N-methylmorpholine (NMM), 1,4-diazabicyclo[2.2.2]octane (DABCO) and tBuOK, or an inorganic base, such as potassium carbonate, sodium carbonate and cesium carbonate, is sometimes advantageous for smoothly proceeding the reaction.

(Second Step)

This step is a method for producing a compound (5) by an ipso substitution reaction of the compound (4) and $R^{LG}$—SH. Examples of the $R^{LG}$-SH used here include $C_{1-12}$ alkylthiols.

The reaction conditions are the same as in the first step of the Raw Material Synthesis 1.

(Third Step)

This step is a method for producing a compound (6) by an ipso substitution reaction of the compound (5) and $PG^3$-OH. Examples of the $PG^3$-OH used here include benzyl alcohol and p-methoxybenzyl alcohol.

The reaction conditions are the same as in the first step of the Raw Material Synthesis 1.

(Fourth Step)

This step is a method for producing a compound (7) by a Suzuki-Miyaura coupling reaction of the compound (6) and a boronic acid derivative composed of an $R^1$-boronic acid group or the like. Examples of the boronic acid group or the like used here include, but are not particularly limited to, a boronic acid group, a boronic acid ester group, a boronic acid pinacol ester group, a triol borate salt group and a trifluoroboric acid salt group.

In this reaction, the compound (6) and the boronic acid derivative composed of an $R^1$-boronic acid group or the like are used in an equal amount or with one compound thereof in an excess amount, and the mixture of the compounds is stirred in a solvent inactive for the reaction, in the presence of a base and a palladium catalyst, from at room temperature to under reflux with heat, preferably at 20° C. to 140° C., generally for 0.1 hours to five days. Examples of the solvent used here include, but are not particularly limited to, a halogenated hydrocarbon, such as dichloromethane, 1,2-dichloroethane and chloroform, an aromatic hydrocarbon, such as benzene, toluene and xylene, an ether, such as diethyl ether, THF, DOX and 1,2-dimethoxyethane, an alcohol, such as MeOH, EtOH, isopropyl alcohol and butanol, DMF, DMSO, MeCN, 1,3-dimethylimidazolidin-2-one, water and a mixture thereof. The base is an inorganic base, such as tripotassium phosphate, sodium carbonate, potassium carbonate and sodium hydroxide. The palladium catalyst is tetrakis(triphenylphosphine)palladium, bis(triphenylphosphine)palladium(II) dichloride, [1,1'-bis(diphenylphosphino)ferrocene]palladium(II) dichloride-dichloromethane adduct, (1E,4E)-1,5-diphenylpenta-1,4-dien-3-one/palladium (3:2) and (2-dicyclohexylphosphino-2',6'-diisopropoxy-1,1'-biphenyl)[2-(2'-amino-1,1'-biphenyl)]palladium(II) methanesulfonate or the like. Performing the reaction in the presence of a ligand, such as dicyclohexyl(2',6'-dimethoxybiphenyl-2-yl)phosphine, dicyclohexyl(2',6'-diisopropoxy-[1,1'-biphenyl]-2-yl)phosphine, is sometimes advantageous for smoothly proceeding the reaction. In addition, heating the mixture by microwave irradiation is sometimes advantageous for smoothly proceeding the reaction.

REFERENCE

J. Am. Chem. Soc., 2005, 127, p. 4685-4696

(Fifth Step)

This step is a method for producing a compound (9) by a Suzuki-Miyaura coupling reaction of the compound (7) and a compound (8).

The reaction conditions are the same as in the fourth step of the Raw Material Synthesis 1.

(Sixth Step)

This step is a method for producing a compound (10) by an oxidation reaction of the compound (9).

In this reaction, the compound (9) is treated with an oxidant in an equal amount or an excess amount in a solvent inactive for the reaction, from under cooling to under heating, preferably at −20° C. to 80° C., generally for 0.1 hours to three days. In this reaction, oxidation with m-chloroperbenzoic acid, perbenzoic acid, peracetic acid, sodium hypochlorite or hydrogen peroxide is suitably used. Examples of the solvent include an aromatic hydrocarbon, an ether, a halogenated hydrocarbon such as dichloromethane, DMF, DMSO, ethyl acetate, MeCN and a mixture thereof. Other examples of the oxidant include cumene hydroperoxide, Oxone, active manganese dioxide, chromic acid, potassium permanganate, sodium periodate and the like.

REFERENCE

The Chemical Society of Japan, "Jikken Kagaku Koza (lectures on experimental chemistry)", 5th edition, Vol. 17, Maruzen, 2004

(Seventh Step)

This step is a method for producing a compound (12) by an ipso substitution reaction of the compound (10) and a compound (11).

The reaction conditions are the same as in the first step of the Raw Material Synthesis 1.

(Eighth Step)

This step is a method for producing the compound (13) by a catalytic hydrogenation reaction of the compound (12).

This reaction can be performed by stirring the compound (12) under hydrogen atmosphere, from under normal pressure to under increased pressure, in a solvent inactive for the reaction, such as MeOH, EtOH and ethyl acetate, in the presence of a metal catalyst, from under cooling to under heating, preferably at room temperature, for an hour to five days. As the metal catalyst, a palladium catalyst, such as Pd/C and palladium black, a platinum catalyst, such as a platinum plate and platinum oxide, a nickel catalyst, such as reduced nickel and Raney nickel, or the like is used.

(Ninth Step)

This step is a method for producing the compound (1) by a reaction of the compound (13) and a compound (14).

This reaction is performed using the compound (13) and the compound (14) in an equal amount or with one compound thereof in an excess amount by reacting a mixture of the compounds in the presence of a base, in a solvent inactive for the reaction, from under cooling to under reflux with heat, preferably at 0° C. to 80° C., generally for 0.1 hours to five days. The solvent used here is not particularly limited, and examples thereof include an aromatic hydrocarbon, such as benzene, toluene and xylene, an alcohol, such as MeOH and EtOH, an ether, such as diethyl ether, THF, DOX and 1,2-dimethoxyethane, a halogenated hydrocarbon, such as dichloromethane, 1,2-dichloroethane and chloroform, DMF, DMSO, ethyl acetate, MeCN and a mixture thereof. Examples of the base include, but are not particularly limited to, for example, an organic base, such as TEA, DIPEA, 1,8-diazabicyclo[5.4.0]-7-undecene, n-butyllithium and tBuOK, and an inorganic base, such as sodium hydroxide, sodium carbonate, potassium carbonate, cesium carbonate and sodium hydride. Performing the reaction in the presence of a phase transfer catalyst, such as tetra-n-butylammonium chloride, is sometimes advantageous.

For example, the following can be referred as a reference about this reaction.

The Chemical Society of Japan, "Jikken Kagaku Koza (lectures on experimental chemistry)", 5th edition, Vol. 14, Maruzen, 2005

(Raw Material Synthesis 2)

[Chemical Formula 18]

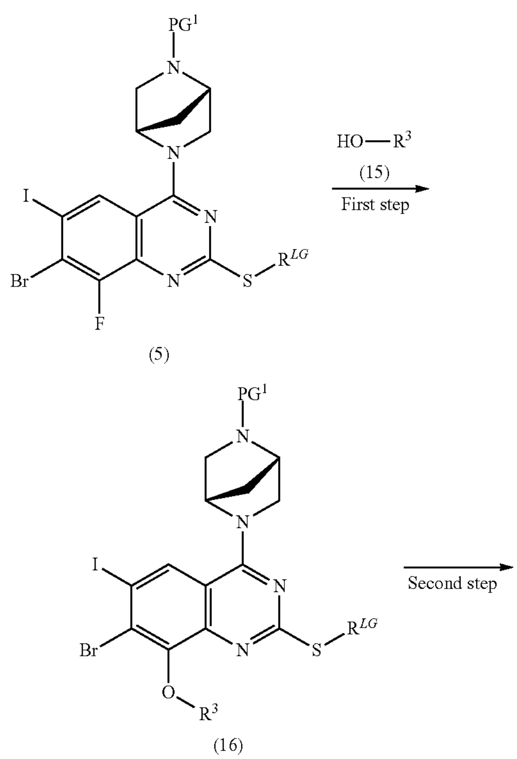

(5)

(16)

-continued

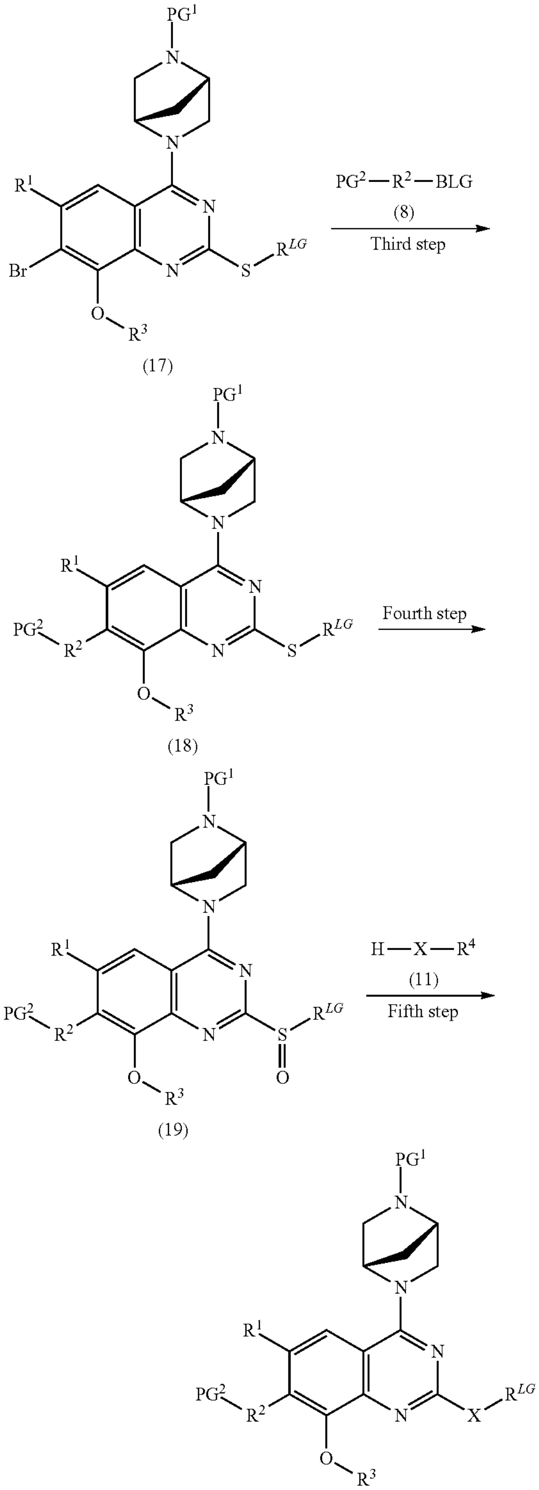

(17)

(18)

(19)

(1)

This production method is a second method for producing the raw material compound (1).

(First Step)

This step is a method for producing a compound (16) by an ipso substitution reaction of the compound (5) and a compound (15).

The reaction conditions are the same as in the first step of the Raw Material Synthesis 1.

(Second Step)

This step is a method for producing a compound (17) by a Suzuki-Miyaura coupling reaction of the compound (16) and a boronic acid derivative composed of an $R^1$-boronic acid group or the like.

The reaction conditions are the same as in the fourth step of the Raw Material Synthesis 1.

(Third Step)

This step is a method for producing a compound (18) by a Suzuki-Miyaura coupling reaction of the compound (17) and the compound (8).

The reaction conditions are the same as in the fourth step of the Raw Material Synthesis 1.

(Fourth Step)

This step is a method for producing a compound (19) by an oxidation reaction of the compound (18).

The reaction conditions are the same as in the sixth step of the Raw Material Synthesis 1.

(Fifth Step)

This step is a method for producing the compound (1) by an ipso substitution reaction of the compound (19) and the compound (11).

The reaction conditions are the same as in the first step of the Raw Material Synthesis 1.

(Raw Material Synthesis 3)

[Chemical Formula 19]

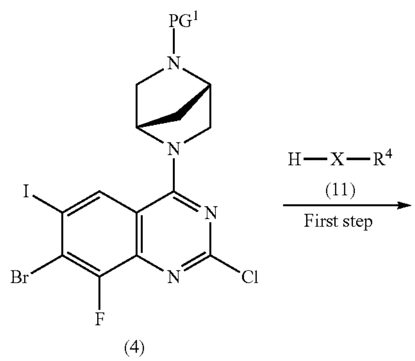

(4)

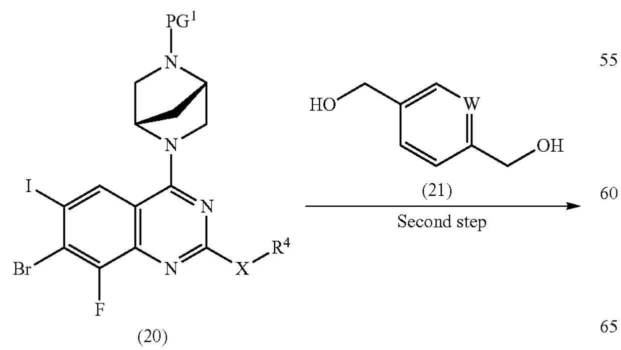

(20)

-continued

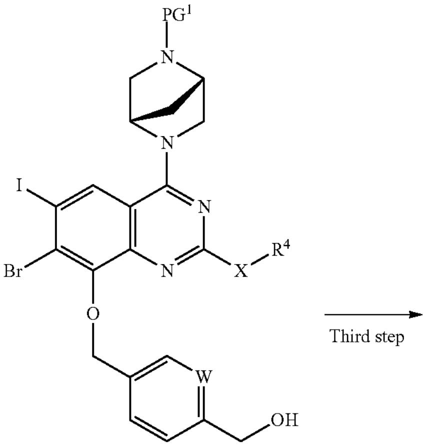

(22)

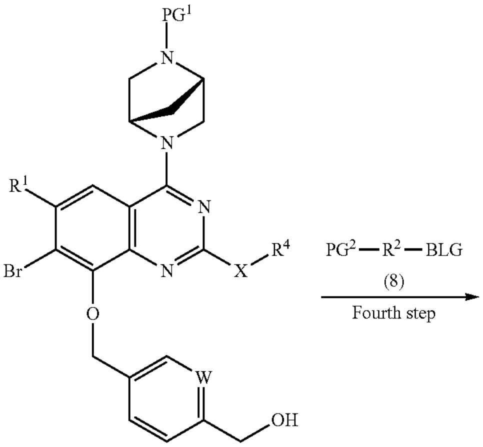

(22)

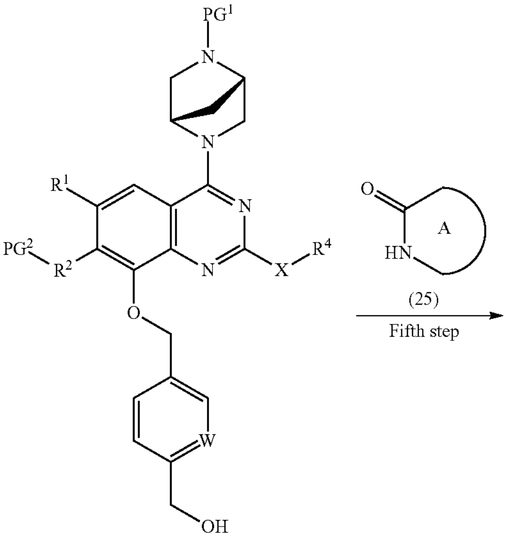

(24)

-continued

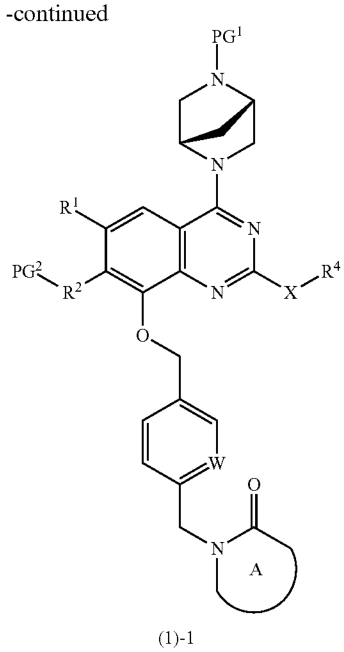

(1)-1

(In the formulae, A in a compound (25) represents a cyclic amide moiety of the formula (IV), (V), (VI), or (VII).)

This production method is a method for producing a raw material compound (1)-1 included in the compound (1).

(First Step)

This step is a method for producing a compound (20) by an ipso substitution reaction of the compound (4) and the compound (11).

The reaction conditions are the same as in the first step of the Raw Material Synthesis 1.

(Second Step)

This step is a method for producing a compound (22) by an ipso substitution reaction of the compound (20) and a compound (21).

The reaction conditions are the same as in the first step of the Raw Material Synthesis 1.

(Third Step)

This step is a method for producing a compound (23) by a Suzuki-Miyaura coupling reaction of the compound (22) and a boronic acid derivative composed of an $R^1$-boronic acid group or the like.

The reaction conditions are the same as in the fourth step of the Raw Material Synthesis 1.

(Fourth Step)

This step is a method for producing a compound (24) by a Suzuki-Miyaura coupling reaction of the compound (23) and a compound (8).

The reaction conditions are the same as in the fourth step of the Raw Material Synthesis 1.

(Fifth Step)

This step is a method for producing the compound (1)-1 by converting a hydroxy group of the compound (24) into a leaving group, which is then subjected to a reaction with a compound (25).

In this reaction, a compound obtained by reacting the compound (24) with thionyl chloride, methanesulfonic anhydride or a halogenated sulfonyl compound, such as methanesulfonyl chloride and paratoluenesulfonyl chloride in a solvent inactive for the reaction, in the presence of a base, from under ice cooling to under reflux with heat, preferably at −20° C. to 60° C., generally for 0.1 hours to five days, and the compound (25) are used in an equal amount or with one compound thereof in an excess amount, and the mixture of the compounds is stirred in a solvent inactive for the reaction, in the presence of a base, from under ice cooling to under reflux with heat, preferably at 0° C. to 120° C., generally for 0.1 hours to five days.

Examples of the solvent include, but are not particularly limited to, an aromatic hydrocarbon, such as toluene, an ether, such as DOX, a halogenated hydrocarbon, such as dichloromethane, DMF, DMSO, ethyl acetate, MeCN and a mixture thereof. Examples of the base include an organic base, such as TEA, DIPEA, NMM and tBuOK, and an inorganic base, such as sodium hydroxide, potassium carbonate, sodium carbonate and potassium hydroxide, and the like.

(Raw Material Synthesis 4)

[Chemical Formula 20]

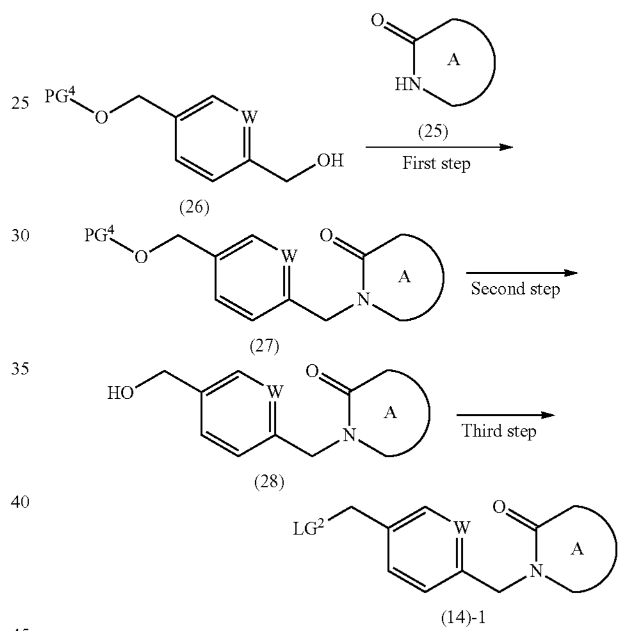

(26)

(27)

(28)

(14)-1

(In the formula, $PG^4$ represents a protective group or a hydrogen atom, and $LG^2$ represents a leaving group.)

The production method is a method for producing a compound (14)-1 in which $R^3$ in the raw material compound (14) is the formula (III), and $R^5$ in the formula (III) is the formula (IV) or the formula (V).

(First Step)

This step is a method for producing a compound (27) by converting a hydroxy group of a compound (26) into a leaving group, followed by a reaction of the resulting compound with the compound (25).

The reaction conditions are the same as in the fifth step of the Raw Material Synthesis 3.

(Second Step)

This step is a method for producing a compound (28) by subjecting the compound (27) to a deprotection reaction.

For example, the following can be referred as a reference about this reaction.

P. G. M. Wuts and T. W. Greene, "Greene's Protective Groups in Organic Synthesis", 5th edition, John Wiley & Sons Inc., 2014

(Third Step)

This step is a method for producing the compound (14)-1 by converting a hydroxy group of the compound (28) into a leaving group.

The reaction conditions are the same as in the conversion reaction into a leaving group described in the fifth step of the Raw Material Synthesis 3.

(Raw Material Synthesis 5)

[Chemical Formula 21]

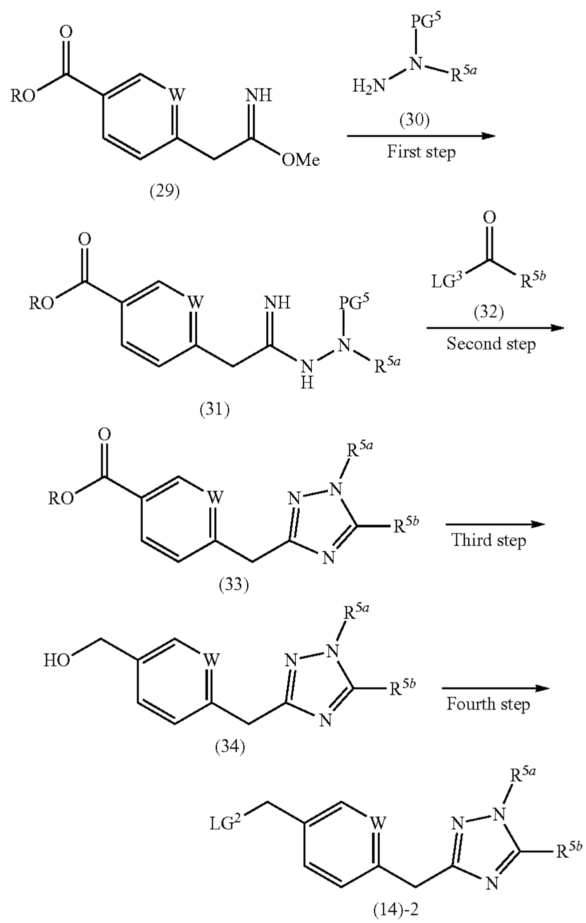

(In the formulae, R represents a $C_{1-3}$ alkyl group, $PG^5$ represents a protective group or a hydrogen atom, and $LG^3$ represents a leaving group or a hydroxy group.)

The production method is a method for producing a compound (14)-2 in which $R^3$ in the raw material compound (14) is the formula (III), and $R^5$ in the formula (III) is the formula (VIII).

(First Step)

This step is a method for producing a compound (31) by a reaction of a compound (29) and a compound (30).

In this reaction, the compound (29) and the compound (30) are used in an equal amount or with one compound thereof in an excess amount, and the mixture of the compounds is stirred in a solvent inactive for the reaction, from under cooling to under heating, preferably at −20° C. to 60° C., generally for 0.1 hours to 5 days. Examples of the solvent include, but are not particularly limited to, an ether, such as THF and DOX, a halogenated hydrocarbon, such as dichloromethane, an alcohol, DMF, DMSO, ethyl acetate, MeCN, pyridine and a mixture thereof. Performing the reaction in the presence of an organic base, such as TEA, DIPEA and NMM, or an inorganic base, such as potassium carbonate, sodium carbonate and potassium hydroxide, is sometimes advantageous for smoothly proceeding the reaction.

(Second Step)

This step is a method for producing a compound (33) by subjecting the compound (31) to a deprotection reaction and then subjecting the resulting compound and a compound (32) to an acylation reaction, followed by a cyclization reaction.

For example, the following can be referred as a reference about the deprotection reaction of this reaction.

P. G. M. Wuts and T. W. Greene, "Greene's Protective Groups in Organic Synthesis", 5th edition, John Wiley & Sons Inc., 2014

In this reaction, the compound (31) is subjected to a deprotection reaction, and then the resulting compound and the compound (32) are used in an equal amount or with one compound thereof in an excess amount, and the mixture of the compounds is stirred in the presence of a condensing agent, in a solvent inactive for the reaction, from under cooling to under heating, preferably at −20° C. to 60° C., generally for 0.1 hours to 5 days. Examples of the solvent include, but are not particularly limited to, an aromatic hydrocarbon, such as toluene, an ether, such as THF and DOX, a halogenated hydrocarbon such as dichloromethane, an alcohol, DMF, DMSO, ethyl acetate, MeCN and a mixture thereof. Examples of the condensing agent include O-(7-azabenzotriazol-1-yl)-N,N,N',N'-tetramethyluronium hexafluorophosphatem, 1-(3-dimethylaminopropyl)-3-ethylcarbodiimide or the hydrochloride thereof, dicyclohexylcarbodiimide, 1,1'-carbonyldiimidazole, diphenylphosphoryl azide and the like. Use of an additive (for example, 1-hydroxybenzotriazole) is sometimes preferred for the reaction. Performing the reaction in the presence of an organic base, such as TEA, DIPEA and NMM, or an inorganic base, such as potassium carbonate, sodium carbonate and potassium hydroxide, is sometimes advantageous for smoothly proceeding the reaction.

Alternatively, a method in which the compound (32) is converted into a reactive derivative, which is then subjected to an acylation reaction, can be used. Examples of the reactive derivative of a carboxylic acid include an acid halogenation product obtained by a reaction with a halogenating agent, such as phosphorus oxychloride, thionyl chloride and oxalyl dichloride, a mixed acid anhydride obtained by a reaction with isobutyl chloroformate or the like, an active ester obtained by condensation with 1-hydroxybenzotriazole or the like and the like. The reaction of such a reactive derivative and the compound obtained by deprotection of the compound (31) can be performed in a solvent inactive for the reaction, such as a halogenated hydrocarbon, an aromatic hydrocarbon and an ether, from under cooling to under heating, preferably at −20° C. to 60° C.

REFERENCE

S. R. Sandler and W. Karo, "Organic Functional Group Preparations", 2nd edition, Vol. 1, Academic Press Inc., 1991

The Chemical Society of Japan, "Jikken Kagaku Koza (lectures on experimental chemistry)", 5th edition, Vol. 16, Maruzen, 2005

Furthermore, in this reaction, the compound obtained by the acylation reaction is stirred in a solvent inactive for the reaction, from at room temperature to under heating, preferably at 20° C. to 150° C., generally for 0.1 hours to 5 days. Examples of the solvent include, but are not particularly limited to, an aromatic hydrocarbon, such as xylene, an alcohol, such as isoamyl alcohol, DMF, DMA, DMSO and a mixture thereof.

(Third Step)

This step is a method for producing a compound (34) by a reduction reaction of the compound (33).

This reaction is performed by reacting the compound (33) with a reductant in an equal amount or an excess amount in a solvent inactive for the reaction, from under cooling to under reflux with heat, preferably at −20° C. to 60° C., generally for 0.1 hours to five days. Examples of the solvent used here include, but are not particularly limited to, an aromatic hydrocarbon, such as benzene, toluene and xylene, and an ether, such as diethyl ether, THF, DOX and 1,2-dimethoxyethane. Examples of the reductant include, but are not limited to, LAH, borane-tetrahydrofuran complex, diborane and the like.

For example, the following can be referred as a reference about this reaction.

The Chemical Society of Japan, "Jikken Kagaku Koza (lectures on experimental chemistry)", 5th edition, Vol. 14, Maruzen, 2005

(Fourth Step)

This step is a method for producing the compound (14)-2 by converting a hydroxy group of the compound (34) into a leaving group.

The reaction conditions are the same as in the conversion reaction into a leaving group described in the fifth step of the Raw Material Synthesis 3.

(Raw Material Synthesis 6)

[Chemical Formula 22]

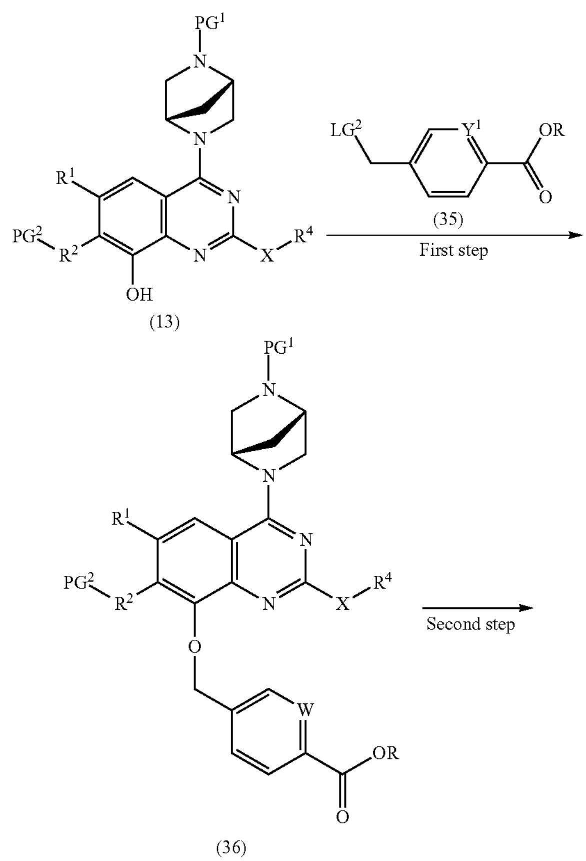

(13)

(35)

(36)

-continued

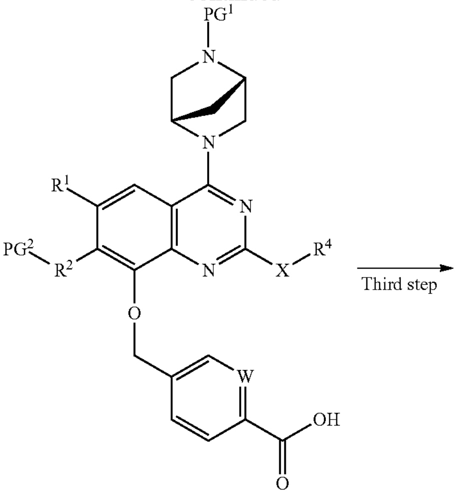

(37)

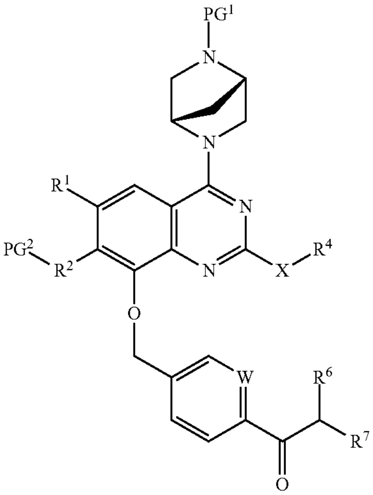

(1)-2

This production method is a method for producing a raw material compound (1)-2 included in the compound (1).

(First Step)

This step is a method for producing a compound (36) by a reaction of the compound (13) and a compound (35).

The reaction conditions are the same as in the ninth step of the Raw Material Synthesis 1.

(Second Step)

This step is a method for producing a compound (37) by hydrolysis of the compound (36).

This reaction is performed by stirring the compound (36) from under cooling to under reflux with heat, generally for 0.1 hours to five days. Examples of the solvent used here include, but are not particularly limited to, an alcohol, acetone, N,N-dimethylformamide, tetrahydrofuran and the like. In addition, a mixed solvent of the above solvent and water is sometimes suitable for the reaction. Examples of the hydrolysis reagent include, but are not particularly limited to, an aqueous sodium hydroxide solution, an aqueous potassium hydroxide solution, trimethyltin hydroxide and the like.

For example, the following can be referred as a reference about this reaction.

The Chemical Society of Japan, "Jikken Kagaku Koza (lectures on experimental chemistry) (5th edition)", Vol. 16 (2005) (Maruzen)

Angew. Chem. Int. Ed. 2005, 44, p. 1378-1382.

(Third Step)

This step is a method for producing a compound (1)-2 by an amidation reaction of the compound (37).

In this reaction, the compound (37) and an amine compound are used in an equal amount or with one compound thereof in an excess amount, and the mixture of the compounds is stirred in the presence of a condensing agent, in a solvent inactive for the reaction, from under cooling to under heating, preferably at −20° C. to 60° C., generally for 0.1 hours to five days. Examples of the solvent include, but are not particularly limited to, an aromatic hydrocarbon, such as toluene, an ether, such as THF and DOX, a halogenated hydrocarbon, such as dichloromethane, an alcohol, N,N-dimethylformamide, DMSO, ethyl acetate, MeCN and a mixture thereof. Examples of the condensing agent include (benzotriazol-1-yloxy)tripyrrolidinophosphonium hexafluorophosphate (PyBOP), 0-(7-azabenzotriazol-1-yl)-N,N,N',N'-tetramethyluronium hexafluorophosphate (HATU), 1-(3-dimethylaminopropyl)-3-ethylcarbodiimide or the hydrochloride thereof, N,N'-dicyclohexylcarbodiimide (DCC), 1,1'-carbonyldiimidazole (CDI), diphenylphosphoryl azide (DPPA) and the like. Use of an additive (for example, 1-hydroxybenzotriazole) is sometimes preferred for the reaction. Performing the reaction in the presence of an organic base, such as TEA, DIPEA and NMM, or an inorganic base, such as potassium carbonate, sodium carbonate and potassium hydroxide, is sometimes advantageous for smoothly proceeding the reaction.

Alternatively, a method in which the compound (37) is converted into a reactive derivative, which is then subjected to an acylation reaction, can be used. Examples of the reactive derivative of a carboxylic acid include an acid halogenation product obtained by a reaction with a halogenating agent, such as phosphorus oxychloride and thionyl chloride, a mixed acid anhydride obtained by a reaction with isobutyl chloroformate or the like, an active ester obtained by condensation with 1-hydroxybenzotriazole or the like and the like. The reaction of such a reactive derivative and the amine compound can be performed in a solvent inactive for the reaction, such as a halogenated hydrocarbon, an aromatic hydrocarbon and an ether, from under cooling to under heating, preferably at −20° C. to 120° C.

REFERENCE

S. R. Sandler and W. Karo, "Organic Functional Group Preparations", 2nd edition, Vol. 1, Academic Press Inc., 1991

The Chemical Society of Japan, "Jikken Kagaku Koza (lectures on experimental chemistry (5th edition)", Vol. 16 (2005) (Maruzen)

(Raw Material Synthesis 7)

[Chemical Formula 23]

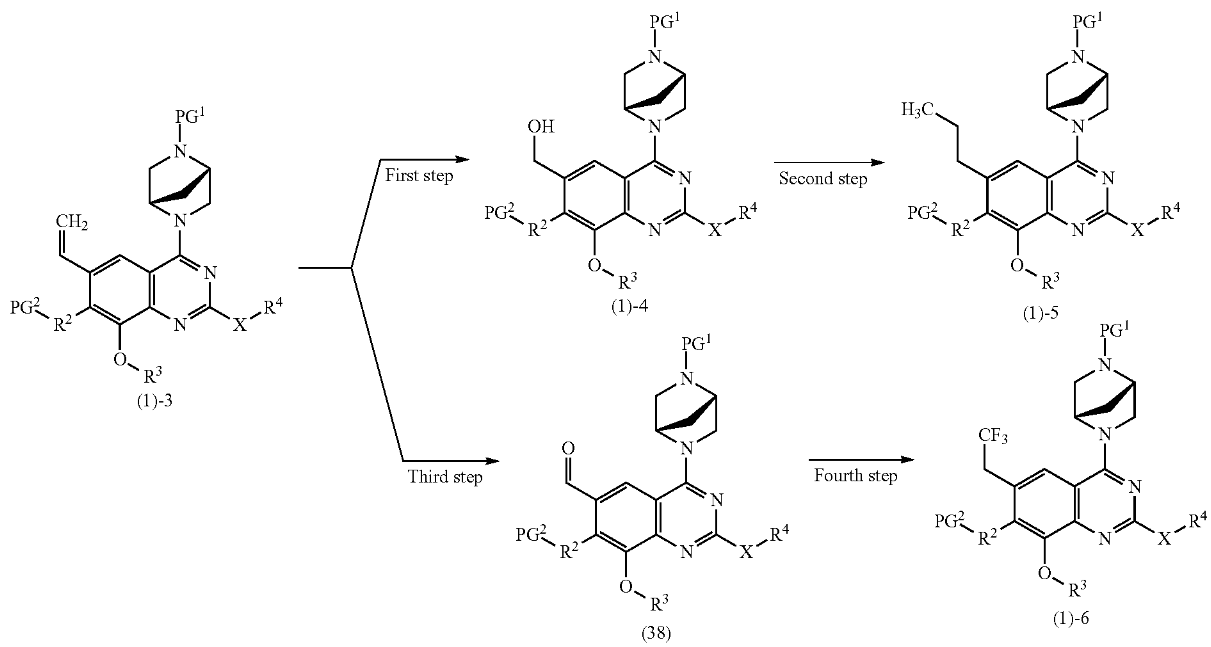

(1)-3 (1)-4 (1)-5 (38) (1)-6

This production method is a method for producing raw material compounds (1)-4, (1)-5 and (1)-6 included in the compound (1).

(First Step)

This step is a method for producing the compound (1)-4 by subjecting the compound (1)-3 to ozonolysis and then to a reduction reaction.

In this reaction, the compound (1)-3 and ozone are first used in an equal amount or with one compound thereof in an excess amount, and the mixture of the compounds is stirred in a solvent inactive for the reaction, from under cooling to room temperature, preferably at −78° C. to 0° C., generally for 0.1 hours to 1 day. Subsequently, the ozone is removed with oxygen or the like. A reductant in an equal amount or an excess amount is then added to the reaction solution, and the mixture is stirred under cooling to room temperature, preferably at −78° C. to at room temperature, generally for 0.1 hours to 1 day. Examples of the reductant used here include a phosphite ester, such as trimethyl phosphite, dimethyl sulfide and the like. Examples of the solvent include, but are not particularly limited to, a halogenated hydrocarbon, such as dichloromethane, 1,2-dichloroethane and chloroform, an alcohol, such as methanol and ethanol, a hydrocarbon, such as pentane, ethyl acetate, water and mixtures thereof.

The subsequent reduction reaction is performed by adding a reductant in an equal amount or an excess amount to the reaction solution and reacting the mixture under cooling to under reflux with heat, preferably at −20° C. to 60° C., generally for 0.1 hours to 5 days.

Examples of the reductant here include, but are not limited to, LAH, sodium borohydride and the like.

For example, the following can be referred as a reference about this reaction.

J. Med. Chem., 2012, 55, p. 3364-3386

The Chemical Society of Japan, "Shin Jikken Kagaku Koza (lectures on new experimental chemistry)", Vol. 14 (1977) (Maruzen)

(Second Step)

This step is a method for producing the compound (1)-5 by a methylation reaction of the compound (1)-4.

In this reaction, the compound (1)-4 and a methylating agent are used in an equal amount or with one compound thereof in an excess amount, and the mixture of the compounds is stirred in a solvent inactive for the reaction or with no solvent, from under cooling to under reflux with heat, preferably at 0° C. to 80° C., generally for 0.1 hours to five days. Examples of the methylating agent include methyl iodide, dimethyl sulfate, methyl trifluoromethanesulfonate and the like. Examples of the solvent include, but are not particularly limited to, a halogenated hydrocarbon, such as dichloromethane, 1,2-dichloroethane and chloroform, an ether, such as diethyl ether, THF, DOX and 1,2-dimethoxyethane, DMF, DMSO, ethyl acetate, MeCN and a mixture thereof. Performing the reaction in the presence of an organic base, such as TEA, DIPEA, 1,4-diazabicyclo[2.2.2]octane (DABCO) and tBuOK, or an inorganic base, such as sodium hydride, potassium carbonate, sodium carbonate and cesium carbonate, is sometimes advantageous for smoothly proceeding the reaction.

(Third Step)

This step is a method for producing a compound (38) by ozonolysis of the compound (1)-3.

The reaction conditions are the same as in the production method by ozonolysis in the first step of the Raw Material Synthesis 7.

For example, the following can be referred as a reference about this reaction.

The Chemical Society of Japan, "Shin Jikken Kagaku Koza (lectures on new experimental chemistry)", Vol. 15 (1976) (Maruzen)

(Fourth Step)

This step is a method for producing the compound (1)-6 by reacting the compound (38) with a difluoroolefinating agent, followed by a trifluoromethylation reaction using a fluorinating agent.

In this reaction, the compound (38) and the difluoroolefinating agent are used in an equal amount or with one compound thereof in an excess amount, and the mixture of the compounds is stirred in a solvent inactive for the reaction, from under cooling to under reflux with heat, preferably at 0° C. to 80° C., generally for 0.1 hours to five days.

Subsequently, the fluorinating agent in the solvent inactive for the reaction is added to the reaction solution in an equal amount or an excess amount, and the mixture is stirred from under cooling to under reflux with heat, preferably at 0° C. to 80° C., generally for 0.1 hours to five days. Examples of the difluoroolefinating agent include $Ph_3P^+CF_2CO_2^-$, $(Me_2N)_3P^+CF_2CO_2^-$ and the like. Examples of the fluorinating agent include tetra-n-butylammonium fluoride and the like. Examples of the solvent include, but are not particularly limited to, an aromatic hydrocarbon, such as toluene, an ether, such as THF, DOX and 1,2-dimethoxyethane, DMF, DMA, ethyl acetate, MeCN and a mixture thereof.

For example, the following can be referred as a reference about this reaction.

J. Org. Chem., 2014, 79, p. 7122-7131

The compound of the formula (I) is isolated and purified as a free compound, a salt, hydrate, solvate or crystal polymorphous substance thereof or a substance in amorphous solid form. A salt of the compound of the formula (I) can also be produced by subjecting the compound to a salt formation reaction which is an ordinary method.

The isolation and purification are performed by applying a common chemical operation, such as extraction, fractional crystallization and various types of fraction chromatography.

Various types of isomers can be produced by selecting an appropriate raw material compound or can be separated by using a difference in physiochemical properties between the isomers. For example, an optical isomer can be obtained by a general optical resolution method of a racemate (for example, fractional crystallization for inducing to a diastereomer salt with an optically active base or acid, chromatography using a chiral column or the like and the like) and can also be produced from an appropriate optically active raw material compound.

In addition, the compound of the formula (I) or an intermediate thereof sometimes has an axial chirality and is obtained as a mixture of diastereomers, and each diastereomer can be isolated by separation using a common separation operation, for example, ODS column chromatography or silica gel column chromatography.

The pharmacological activities of the compounds of the formula (I) were confirmed by the following tests.

Test Example 1: Evaluation of KRAS G12D/SOS/c-Raf Complex Formation Inhibitory Activity Using human recombinant KRAS G12D, SOS and c-Raf proteins, the inhibitory activity of subject compounds on the complex formation of the proteins was examined by a time-resolved fluorescence resonance energy transfer (TR-FRET) method.

Biotinylated AviTag-KRAS G12D (amino acid region of 1-185, GDP) (2.5 μL; 400 nM) and subject compounds dissolved in an assay buffer (50 mM HEPES, 150 mM NaCl, 5 mM $MgCl_2$, 0.05% Tween 20, pH 7.0) were added to a 384-well plate (from Corning) in a liquid volume of 2.5 μL at 40,000 nM to 40 nM. Son of Sevenless (SOS) (amino acid region of 564-1049, 2.5 μL; 1.3 μM) and c-Raf (amino acid region of 51-131) GST (2.5 μL; 130 nM) containing GTP (from Sigma-Aldrich; 2 μM) were added to the plate, and the plate was allowed to stand for 1 hour at room temperature. Then, a mixture liquid (10 μL) of LANCE Ulight-anti-GST (from PerkinElmer; 120 nM) and LANCE Eu-W1024 labeled Streptoavidin (from PerkinElmer; 100 ng/mL) was added, and the 620-nm and 665-nm fluorescence intensities were measured using EnVision 2104 (from PerkinElmer) under the conditions of an excitation wavelength of 337 nm. After standardizing the values with the fluorescence intensity at a reference wavelength of 620 nm, the 50% inhibitory concentrations ($IC_{50}$) were calculated by Sigmoid-Emax model nonlinear regression analysis with the signaling value in treatment with the solvent taken as 0% inhibition and with the signaling value without the addition of GTP taken as 100% inhibition. The results of some subject compounds of the formula (I) are shown in Table 1 below.

TABLE 1

| Ex | $IC_{50}$ (nM) |
|---|---|
| 1 | 44 |
| 2 | 96 |
| 3 | 75 |
| 4 | 100 |
| 5 | 107 |
| 6 | 91 |
| 7 | 105 |
| 8 | 40 |
| 9 | 44 |
| 10 | 33 |
| 11 | 110 |
| 12 | 74 |
| 13 | 77 |
| 14 | 143 |
| 15 | 88 |
| 16 | 226 |
| 18 | 92 |
| 19 | 65 |
| 20 | 70 |
| 22 | 161 |
| 23 | 68 |

Test Example 2: Evaluation of ERK Phosphorylation Inhibitory Activity on Human KRAS G12D Mutant-Positive Pancreatic Cancer Line AsPC-1

The ERK phosphorylation inhibitory activities of subject compounds were evaluated by measuring phosphorylation of the 202th threonine (Thr202) and the 204th tyrosine (Tyr204) of ERK located downstream of the KRAS signal by cell ELISA.

AsPC-1 cells (ATCC, CRL-1682) were seeded at 36 μL/well on a 384-well plate (from Greiner bio-one) to give $2.0\times10^4$ cells per well. As for the cell culture conditions, RPMI-1640 medium (from Sigma-Aldrich) containing 10% fetal bovine serum (from GE Life Sciences) was used in the presence of 5% $CO_2$ at 37° C.

The next day, the subject compounds (6 points having final concentrations in the range of 10 μM to 0.3 nM), trametinib (MEK inhibitor) of a final concentration of 1 μM as a positive control and DMSO, which was the solvent for the subject compounds, as a negative control were diluted 100-fold with a fresh medium and were each added at 4 μL per well, followed by culturing for 2 hours. After culturing, a 30% glyoxal solution (40% glyoxal [from Wako] was diluted with Phosphate Buffered Saline [PBS; from Wako) was quickly added at 30 μL per well, and the plate was allowed to stand for an hour at room temperature to thus immobilize the cells. Then, the plate was centrifuged (110× g, seven seconds, hereinafter centrifugation was performed under the same conditions unless otherwise specified) to remove the supernatant, and 0.1% Triton X-100 (from Amersham Biosciences)—containing PBS was added at 20 μL per well. After allowing the plate to stand for 10 minutes at room temperature, the supernatant was removed by centrifugation, and the same operation was further repeated. Next, 0.5% sodium dodecyl sulfate (SDS; from Invitrogen)-containing PBS was added at 20 μL per well. The plate was allowed to stand at room temperature for 30 minutes and was then centrifuged to remove the supernatant. Subsequently, a blocking solution (Intercept Blocking Buffer; from LI-COR Biosciences) was added at 20 μL per well, and the plate was allowed to stand for an hour at room temperature. The supernatant was removed by centrifugation, and an ERK (Thr202/Tyr204) phosphorylation antibody (Phospho-p44/42 MAPK (Erk 1/2) (Thr202/Tyr204) (D13.14.4E) XP Rabbit mAb; from Cell Signaling Technology) diluted 2,500-fold with the blocking solution was added at 10 μL per well as a primary antibody. The plate was allowed to stand at 4° C. overnight.

The next day, the plate was centrifuged to remove the supernatant, and 0.05% Tween-20-containing PBS (from Thermo Scientific; 20×PBS Tween-20 was diluted 20-fold with ion exchange water and used) was added at 20 μL per well. The supernatant was removed by centrifugation to thus wash each well. The washing was performed three times in total. After washing, an IRDye 800CW Goat anti-Rabbit IgG (from LI-COR Biosciences) diluted 1,000-fold with the blocking solution was added at 10 μL per well as a secondary antibody, and the plate was allowed to stand for an hour at room temperature. The plate was centrifuged to remove the supernatant, and each well was washed three times with 0.05% Tween-20-containing PBS in the same manner as after the primary antibody reaction. Centrifugation after the third washing was performed at 171×g for 17 seconds. After removing the supernatant, the plate was dried as it was with air at room temperature for three hours or more, and the 800-nm fluorescent signals were measured with Aerius (from LI-COR Biosciences).

With the signaling value at the time of addition of DMSO taken as 0% inhibition and with the signaling value at the time of addition of 1 μL trametinib taken as 100% inhibition, the 50% inhibition values ($IC_{50}$) were calculated by Sigmoid-Emax model nonlinear regression analysis. The results of some subject compounds of the formula (I) are shown in Table 2 below.

TABLE 2

| Ex | $IC_{50}$ (nM) |
|---|---|
| 2 | 49 |
| 3 | 55 |
| 4 | 37 |
| 5 | 32 |
| 6 | 36 |
| 8 | 30 |
| 9 | 44 |
| 10 | 41 |
| 11 | 81 |
| 12 | 72 |
| 13 | 78 |
| 14 | 42 |
| 16 | 93 |

Test Example 3: Evaluation of Non-Anchorage-Dependent Cell Growth Inhibitory Activity on Human KRAS G12D Mutant-Positive Pancreatic Cancer Line AsPC-1

The non-anchorage-dependent cell growth inhibitory activities of subject compounds were evaluated by spheroid 3D cell culture.

AsPC-1 cells were seeded at 36 μL/well on a low-cell-adhesive round bottom 384-well plate (Prime Surface: from Sumitomo Bakelite) to give $5\times10^2$ cells per well. The cell culture was performed under the same conditions as in the Test Example 2.

The next day, the subject compounds (6 points having final concentrations in the range of 10 μM to 3.0 nM) and DMSO, which was the solvent for the subject compounds, as a negative control were diluted 100-fold with a fresh medium and were each added at 4 μL per well. After culturing in the presence of 5% $CO_2$ at 37° C. for six days, CellTiter Glo 2.0 (from Promega) was added at 20 μL per well. After stirring with a plate mixer (from FINEPCR) at normal temperature for an hour, the luminescent signals were measured with ARVO X3 (from PerkinElmer).

With the signaling value in treatment with DMSO taken as 0% inhibition and with the signaling value in the medium alone without cells taken as 100% inhibition, the 50% inhibition values ($IC_{50}$) were calculated by Sigmoid-Emax model nonlinear regression analysis. The results of some subject compounds of the formula (I) are shown in Table 3 below.

TABLE 3

| Ex | $IC_{50}$ (nM) |
|---|---|
| 1 | 68 |
| 2 | 166 |
| 3 | 128 |
| 4 | 99 |
| 5 | 83 |
| 6 | 92 |
| 7 | 80 |
| 8 | 73 |
| 9 | 84 |
| 10 | 77 |
| 11 | 133 |
| 12 | 153 |
| 13 | 130 |
| 14 | 154 |
| 15 | 152 |
| 16 | 216 |
| 18 | 192 |
| 19 | 189 |
| 20 | 138 |
| 22 | 209 |

Test Example 4: Evaluation of Anti-Tumor Activity in Human KRAS G12D Mutant-Positive Pancreatic Cancer Line PK-1 Xenograft Mouse PK-1 cells (RIKEN BRC, RCB1972) were cultured using RPMI-1640 medium (from Sigma-Aldrich) containing 10% fetal bovine serum (from GE Life Sciences) in the presence of 5% $CO_2$ at 37° C. The PK-1 cells were collected and suspended in PBS, and an equivalent of Matrigel (from Becton, Dickinson and Company) was added. A cell suspension prepared at $3.0\times10^7$ cells/mL was subcutaneously inoculated in a volume of 100 μL in 4- to 5-week-old male nude mice (CAnN.Cg-Foxn1$^{nu}$/CrlCrlj (nu/nu), from Charles River Laboratories Japan). After about two weeks of the inoculation, the mice were divided into groups so that all the groups had approximately the same tumor volume and body weight, and administration of a subject compound was started on the next day. The test was conducted for five mice for each of a solvent group and a subject compound administration group. An aqueous solution (solvent A) of 10% propylene glycol (from Maruishi Pharmaceutical. Co., Ltd.), 5% polyoxyethylene sorbitan monooleate (Tween 80; from Nacalai Tesque, Inc.), 2.5% citric acid monohydrate (from Nacalai Tesque) and 2.5% KLEPTOSE HPB (form Roquette) was orally administered to the solvent group, while a mixture of the solvent A and the subject compounds was orally administered to the subject compound administration group. The administration was performed twice a day for 14 weeks, and the tumor size and the body weight were measured twice a week. The tumor volume was calculated by using the following formula.

$$[\text{Tumor volume}(mm^3)]=[\text{Major axis of tumor (mm)}]\times[\text{Minor axis of tumor (mm)}]^2\times0.5$$

The tumor growth inhibition (%) by the subject compound was calculated with the tumor volume of the subject compound administration group on the previous day of the start of the administration taken as 100% inhibition and the tumor volume of the solvent group of the day of the final measurement taken as 0% inhibition. In addition, when the tumor volume of the subject compound administration group was smaller than the tumor volume on the previous day of the start of the administration, the tumor regression (%) by the subject compound was calculated with the tumor volume on the previous day of the start of the administration taken as 0% regression and with the tumor volume 0 taken as 100% regression.

As a result of the above tests, in some compounds of the formula (I), a G12D mutant KRAS inhibitory activity and anti-tumor activity were found. Accordingly, the compound of the formula (I) can be used for the treatment or the like of pancreatic cancer, in particular, KRAS G12D mutant-positive pancreatic cancer.

A pharmaceutical composition that contains one or two or more compounds of the formula (I) or salts thereof as active ingredients can be prepared by a usually used method using an excipient usually used in the art, that is, a pharmaceutical excipient, a pharmaceutical carrier or the like.

The administration may be either oral administration with a tablet, pill, capsule, granule, powder, liquid or other agent or parenteral administration with an intraarticular, intravenous, intramuscular or other injection, a suppository, an eye drop, an ophthalmic ointment, a transdermal solution, an ointment, a transdermal patch, a transmucosal solution, a transmucosal patch, an inhalant or the like.

As a solid composition for oral administration, a tablet, powder, granular or other agent is used. In such a solid composition, one or two or more active ingredients are mixed with at least one inactive excipient. The composition may contain an inactive additive, for example, a lubricant, a disintegrator, a stabilizer or a dissolution aid, according to an ordinary method. A tablet or pill may be coated with a sugar coating or a film soluble in the stomach or intestine, when needed.

Liquid compositions for oral administration include a pharmaceutically acceptable emulsion, solution, suspension, syrup or elixir agent and the like and contain a generally used inactive diluent, for example, purified water or EtOH (ethanol). The liquid composition may contain, in addition to the inactive diluent, an adjuvant, such as a solubilizer, a wetting agent and a suspending agent, a sweetening agent, a flavor, a fragrant or a preservative.

The injection agents for parenteral administration include a sterile aqueous or nonaqueous solution, suspension or emulsion agent. Examples of the aqueous solvent include distilled water for injection or physiological saline. An example of the nonaqueous solvent is an alcohol, such as EtOH. Such a composition may further contain an isotonizing agent, a preservative, a wetting agent, an emulsifier, a dispersant, a stabilizer or a dissolution aid. These are sterilized, for example, by filtration through a bacteria keeping filter, incorporation of a microbicide or irradiation. In addition, such a composition can be produced as a sterile solid composition, which is dissolved or suspended in sterile water or a sterile solvent for injection before use.

The transmucosal agent, such as an inhalant or a transnasal agent, is used in a solid, liquid or semi-solid form and can be produced according to a conventionally known method. For example, a known excipient and in addition, a pH modifier, a preservative, a surfactant, a lubricant, a stabilizer, a thickener or the like may be appropriately added. The administration can be performed by using an appropriate device for inhalation or insufflation. For example, the agent can be administered using a known device, such as a metering and administering inhalation device, or an atomizer, as a compound alone or a powder of a mixture formulated, or as a solution or a suspension in combination with a pharmaceutically acceptable carrier. A dry powder inhaler or the like may be for a single administration or multiple administrations, and dry powder or powder-containing capsule can be used. Alternatively, the agent may be used in a form of a pressurized aerosol spray or the like using an appropriate ejection agent, for example, a suitable gas, such as a chlorofluoroalkane or carbon dioxide.

In the case of a common oral administration, the daily dose is appropriately about 0.001 to 100 mg/kg body weight, preferably 0.1 to 30 mg/kg body weight, further preferably 0.1 to 10 mg/kg body weight, and the dose is given at once or is divided into two to four times. In the case of intravenous administration, the daily dose is appropriately about 0.0001 to 10 mg/kg body weight and is given at once or is divided into multiple times in a day. In addition, the daily dose of a transmucosal agent is about 0.001 to 100 mg/kg body weight and is given at once or is divided into multiple times in a day. The dose is appropriately decided depending on the individual case taking the symptom, age, sex and the like into account.

Depending on the route of administration, dosage form, site of administration and types of excipient and additive, the pharmaceutical composition of the present invention contains 0.01 to 100% by weight, in an aspect, 0.01 to 50% by weight, of one or more compounds of the formula (I) or salts thereof which are active ingredients.

The compound of the formula (I) can be used in combination with various therapeutic agents or preventive agents for a disease to which the compound of the formula (I) is considered to have an effectiveness. The combination use may be simultaneous administration or separate administration either sequential or with a desired interval. A simultaneous administration preparation may be a formulated agent or may be separately formulated.

EXAMPLES

The production method of the compound of the formula (I) will be explained in further detail below based on the Examples. Note that, the present invention is not to be limited to the compounds described in the following Examples. The production methods of raw material compounds are also shown in the Production Examples. The production method of the compound of the formula (I) is not limited only to the production methods of specific Examples described below, and the compound of the formula (I) can also be produced by a combination of the production methods or a method that is obvious to a person skilled in the art.

Note that, in this specification, a compound is sometimes named by using a naming soft, such as ACD/Name (registered trademark, Advanced Chemistry Development, Inc.).

For the purpose of convenience, the concentration mol/L is shown as M. For example, 1M aqueous sodium hydroxide solution means an aqueous sodium hydroxide solution of 1 mol/L.

Production Example 1

A mixture of 7-bromo-2,4-dichloro-8-fluoro-6-iodoquinazoline (100 g), DOX (1000 mL), THF (500 mL) was cooled with ice, and then DIPEA (240 mL), tert-butyl (1S,4S)-2,5-diazabicyclo[2.2.1]heptane-2-carboxylate (48 g) were added. The mixture was stirred at room temperature overnight. Water was added to the reaction mixture, and the mixture was extracted with ethyl acetate. The organic layer was washed with an aqueous sodium chloride solution, dried over anhydrous magnesium sulfate and then concentrated under reduced pressure until the total amount of the solution became about 400 mL. A mixed solvent (hexane/ethyl acetate=4/1, 1000 mL) was added to the resulting solution, and the mixture was stirred at room temperature for two hours. The precipitated solid was filtered to give tert-butyl (1S,4S)-5-(7-bromo-2-chloro-8-fluoro-6-iodoquinazolin-4-yl)-2,5-diazabicyclo[2.2.1]heptane-2-carboxylate (123 g) as a solid.

Production Example 2

To a mixture of tert-butyl (1S,4S)-5-(7-bromo-2-chloro-8-fluoro-6-iodoquinazolin-4-yl)-2,5-diazabicyclo[2.2.1]heptane-2-carboxylate (20.1 g), DMF (150 mL) and DABCO (3.85 g), cesium carbonate (12.3 g) and dodecane-1-thiol (9.05 mL) were added under ice cooling. The mixture was stirred at 50° C. overnight. Ethyl acetate and water were added to the reaction mixture, and the organic layer and the aqueous layer were separated by a separation operation. The resulting aqueous layer was subjected to extraction twice with ethyl acetate. The organic layers were combined, washed with aqueous sodium chloride solution twice and then dried over anhydrous magnesium sulfate. The solution was concentrated under reduced pressure, thus obtaining tert-butyl (1S,4S)-5-[7-bromo-2-(dodecylsulfanyl)-8-fluoro-6-iodoquinazolin-4-yl]-2,5-diazabicyclo[2.2.1]heptane-2-carboxylate (26.0 g) as an oily substance.

Production Example 4

Under argon flow, to a mixture of tert-butyl (1S,4S)-5-[7-bromo-2-(dodecylsulfanyl)-8-fluoro-6-iodoquinazolin-4-yl]-2,5-diazabicyclo[2.2.1]heptane-2-carboxylate (38.5 g), benzyl alcohol (6.12 g) and THF (390 mL), tBuOK (6.54 g) was added under ice cooling, and the mixture as stirred at the same temperature for 1.5 hours. To the reaction mixture, benzyl alcohol (0.5 mL) and tBuOK (540 mg) were added under ice cooling, and the mixture was further stirred at the same temperature for an hour. Water and saturated aqueous ammonium chloride solution were added to the reaction mixture, and the mixture was extracted with ethyl acetate. The organic layer was washed with saturated aqueous sodium chloride solution and dried over anhydrous magnesium sulfate. The solution was concentrated under reduced pressure, and the resulting residue was purified by silica gel column chromatography (hexane/ethyl acetate), thus obtaining tert-butyl (1S,4S)-5-[8-(benzyloxy)-7-bromo-2-(dodecylsulfanyl)-6-iodoquinazolin-4-yl]-2,5-diazabicyclo[2.2.1]heptane-2-carboxylate (41.5 g) as a gum.

Production Example 7

Under argon atmosphere, a mixture of tert-butyl (1S,4S)-5-[8-(benzyloxy)-7-bromo-2-(dodecylsulfanyl)-6-iodoquinazolin-4-yl]-2,5-diazabicyclo[2.2.1]heptane-2-carboxylate (41.5 g), MeCN (500 mL), DOX (330 mL), water (165 mL), cyclopropylboronic acid (8.0 g), tripotassium phosphate (38 g), $PdCl_2(dppf)\cdot CH_2Cl_2$ (4.0 g) was stirred at 100° C. for 3 hours. After the reaction mixture was allowed to cool to room temperature, the solution was concentrated under reduced pressure. Saturated aqueous sodium chloride solution was added to the resulting residue, and the mixture was extracted with $CHCl_3$. The organic layer was dried over anhydrous magnesium sulfate, and the solution was concentrated under reduced pressure. The resulting residue was purified by silica gel column chromatography (hexane/ethyl acetate), thus obtaining tert-butyl (1S,4S)-5-[8-(benzyloxy)-7-bromo-6-cyclopropyl-2-(dodecylsulfanyl)quinazolin-4-yl]-2,5-diazabicyclo[2.2.1]heptane-2-carboxylate (27.1 g) as a gum.

Production Example 10

A mixture of tert-butyl (1S,4S)-5-[8-(benzyloxy)-7-bromo-6-cyclopropyl-2-(dodecylsulfanyl)quinazolin-4-yl]-2,5-diazabicyclo[2.2.1]heptane-2-carboxylate (33.6 g), 6-fluoro-5-methyl-1-(tetrahydro-2H-pyran-2-yl)-4-(4,4,5,5-tetramethyl-1,3,2-dioxaborolan-2-yl)-1H-indazole (19.3 g), tripotassium phosphate (38 g), dicyclohexyl(2',6'-diisopropoxy-[1,1'-biphenyl]-2-yl)phosphine (3.1 g), (2-dicyclohexylphosphino-2',6'-diisopropoxy-1,1'-biphenyl)[2-(2'-amino-1,1'-biphenyl)]palladium (II) methanesulfonate (5.6 g), DOX (500 mL) and water (80 mL) was bubbled with argon and then stirred under argon atmosphere at 100° C. for 3.5 hours. After the reaction mixture was concentrated under reduced pressure to approximately ½ volume of the solution, an aqueous sodium chloride solution was added, and the mixture was extracted with ethyl acetate. After anhydrous magnesium sulfate and celite were added to the organic layer, followed by stirring, the insoluble matter was filtered through celite. After the filtrate was concentrated under reduced pressure, the resulting residue was purified by silica gel column chromatography (hexane/ethyl acetate), thus obtaining tert-butyl (1S,4S)-5-{8-(benzyloxy)-6-cyclopropyl-2-(dodecylsulfanyl)-7-[6-fluoro-5-methyl-1-(oxan-2-yl)-1H-indazol-4-yl]quinazolin-4-yl}-2,5-diazabicyclo[2.2.1]heptane-2-carboxylate (33.0 g) as a foam-like solid.

Production Example 13

To a solution of tert-butyl (1S,4S)-5-{8-(benzyloxy)-6-cyclopropyl-2-(dodecylsulfanyl)-7-[6-fluoro-5-methyl-1-(oxan-2-yl)-1H-indazol-4-yl]quinazolin-4-yl}-2,5-diazabicyclo[2.2.1]heptane-2-carboxylate (34.5 g) in $CH_2Cl_2$ (350 mL), m-chloroperbenzoic acid (about 30% water content, 10 g) was added under ice cooling, and the mixture was stirred at the same temperature for 30 minutes. Under ice cooling, aqueous sodium thiosulfate solution and saturated aqueous sodium hydrogen carbonate solution were added to the reaction mixture. The aqueous layer and the organic layer were separated by a separation operation, and the resulting aqueous layer was subjected to extraction twice with $CH_2Cl_2$. The resulting organic layer was mixed and dried over anhydrous sodium sulfate. After the resulting solution was concentrated under reduced pressure, toluene was added to the residue. The mixture was concentrated under reduced pressure again, thus obtaining tert-butyl (1S,4S)-5-{8-(benzyloxy)-6-cyclopropyl-2-(dodecane-1-sulfinyl)-7-[6-fluoro-5-methyl-1-(oxan-2-yl)-1H-indazol-4-yl]quinazolin-4-yl}-2,5-diazabicyclo[2.2.1]heptane-2-carboxylate (35.1 g) as a foam-like solid.

Production Example 15

To a mixture of tert-butyl (1S,4S)-5-{8-(benzyloxy)-6-cyclopropyl-2-(dodecane-1-sulfinyl)-7-[6-fluoro-5-methyl-1-(oxan-2-yl)-1H-indazol-4-yl]quinazolin-4-yl}-2,5-diazabicyclo[2.2.1]heptane-2-carboxylate (35.1 g) and THF (420 mL), tetrahydro-2H-pyran-4-ol (5.9 g) and tBuOK (6.4 g) were added at room temperature, and the mixture was stirred for an hour. Water and saturated aqueous ammonium chloride solution were added to the reaction mixture, and the mixture was extracted with ethyl acetate twice. The resulting organic layer was mixed, washed with saturated aqueous sodium chloride solution and dried over anhydrous magnesium sulfate. The solution was concentrated under reduced pressure, and the resulting residue was purified by silica gel column chromatography (basic silica gel, hexane/ethyl acetate), thus obtaining tert-butyl (1S,4S)-5-{8-(benzyloxy)-6-cyclopropyl-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (23.9 g) as a foam-like solid.

Production Example 18

A mixture of tert-butyl (1S,4S)-5-{8-(benzyloxy)-6-cyclopropyl-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (23.9 g), 10% Pd/C (50% water content, 4.8 g) and EtOH (290 ml) was stirred under hydrogen atmosphere at room temperature for eight hours. The resulting reaction mixture was filtered through celite and washed with EtOH (100 ml). To the filtrate, 10% Pd/C (50% water content, 2.4 g) was added again, and the mixture was stirred under hydrogen atmosphere at room temperature overnight. After the resulting reaction mixture was filtered through celite, the filtrate was concentrated under reduced pressure, thus obtaining tert-butyl (1S,4S)-5-{6-cyclopropyl-7-[6-fluoro-5-methyl-1-(oxan-2-yl)-1H-indazol-4-yl]-8-hydroxy-2-[(oxan-4-yl)oxy]quinazolin-4-yl}-2,5-diazabicyclo[2.2.1]heptane-2-carboxylate (20.9 g) as a foam-like solid.

Production Example 19

To a $CH_2Cl_2$ (66 mL) solution of 1-{[4-(hydroxymethyl)phenyl]methyl}-3-methyl-1,3-dihydro-2H-imidazo[4,5-b]pyrazin-2-one (3.3 g), thionyl chloride (3.5 mL) was added under ice cooling, and the mixture was stirred at the same temperature for two hours. The reaction mixture was concentrated under reduced pressure to give the residue as a solid (3.6 g). To a DMF (60 mL) solution of tert-butyl (1S,4S)-5-{6-cyclopropyl-7-[6-fluoro-5-methyl-1-(oxan-2-yl)-1H-indazol-4-yl]-8-hydroxy-2-[(oxan-4-yl)oxy]quinazolin-4-yl}-2,5-diazabicyclo[2.2.1]heptane-2-carboxylate (6.0 g) and the solid obtained above (2.91 g), cesium carbonate (8.3 g) was added at room temperature, and the mixture was stirred at the same temperature for an hour then at 50° C. overnight. Water was added to the reaction mixture, and the mixture was stirred for 10 minutes. The resulting insoluble matter was taken by filtration, thus obtaining tert-butyl (1S,4S)-5-{6-cyclopropyl-7-[6-fluoro-5-methyl-1-(oxan-2-yl)-1H-indazol-4-yl]-8-({4-[(3-methyl-2-oxo-2,3-dihydro-1H-imidazo[4,5-b]pyrazin-1-yl)methyl]phenyl}methoxy)-2-[(oxan-4-yl)oxy]quinazolin-4-yl}-2,5-diazabicyclo[2.2.1]heptane-2-carboxylate (7.88 g) as a solid.

Production Example 38

To a $CH_2Cl_2$ (140 mL) solution of [4-({[tert-butyldi(methyl)silyl]oxy}methyl)phenyl]methanol (7.0 g), methanesulfonic anhydride (9.66 g) and DIPEA (11.4 mL) were added under ice cooling, and the mixture was stirred at the same temperature for an hour. Water was added to the reaction mixture under ice cooling. The organic layer and the aqueous layer were separated by a separation operation, and the aqueous layer was subjected to extraction twice with $CH_2Cl_2$. The resulting organic layer was mixed and then dried over anhydrous sodium sulfate, and the solution was concentrated under reduced pressure. To a DMF (140 mL) solution of the resulting residue and 1-methyl-1,3-dihydro-2H-imidazo[4,5-b]pyrazin-2-one (5.0 g), tBuOK (4.70 g) was added under ice cooling, and the mixture was stirred at the same temperature for 1 hour then at room temperature for 1 hour. Under ice cooling, saturated aqueous ammonium chloride solution was added to the reaction mixture, and the mixture was extracted with ethyl acetate. The organic layer was washed with saturated aqueous sodium chloride solution and then dried over anhydrous sodium sulfate, and the solution was concentrated under reduced pressure. To a THF (70 mL) solution of the resulting residue, tetra-n-butylammonium fluoride (1M THF solution, 42 mL) was added, and the mixture was stirred at room temperature overnight. The reaction mixture was concentrated under reduced pressure, and the resulting residue was purified by silica gel column chromatography ($CHCl_3$/MeOH), thus obtaining 1-{[4-(hydroxymethyl)phenyl]methyl}-3-methyl-1,3-dihydro-2H-imidazo[4,5-b]pyrazin-2-one (4.84 g) as a solid.

Production Example 45

To a mixture of 2-(chloromethyl)imidazo[1,2-a]pyrazine (1 g), [4-(hydroxymethyl)phenyl]borate (1.8 g), DOX (24 mL), water (4.8 mL) and tripotassium phosphate (3.2 g), $PdCl_2$(dppf)-$CH_2Cl_2$ (490 mg) was added, and the mixture was stirred under microwave irradiation at 130° C. for two hours. The resulting reaction mixture was filtered through celite and washed with ethyl acetate. The filtrate was concentrated under reduced pressure, the resulting residue was purified by silica gel column chromatography ($CHCl_3$/MeOH), thus obtaining{4-[(imidazo[1,2-a]pyrazin-2-yl)methyl]phenyl}methanol (1.15 g) as a solid.

Production Example 48

Trifluoroacetic acid (18 mL) was added to a mixture of 6-fluoro-5-methyl-1-(oxan-2-yl)-4-(4,4,5,5-tetramethyl-1,3,2-dioxaborolan-2-yl)-1H-indazole (16 g), triisopropylsilane (24 mL) and $CH_2Cl_2$ (320 mL) at room temperature, and the mixture was stirred for four days. The resulting reaction mixture was concentrated under reduced pressure until approximately the same amount of solvent as that of $CH_2Cl_2$ used was distilled off. THF and water were added to the resulting residue, and saturated aqueous sodium hydrogen carbonate solution was added portionwise with stirring under ice cooling until the reaction solution became weakly basic. The resulting mixture was extracted with $CHCl_3$, and the organic layer was dried over anhydrous magnesium sulfate. The solution was concentrated under reduced pressure, and the resulting residue was purified by silica gel column chromatography (hexane/ethyl acetate), thus obtaining 6-fluoro-5-methyl-4-(4,4,5,5-tetramethyl-1,3,2-dioxaborolan-2-yl)-1H-indazole (11.2 g) as a solid.

Production Example 49

To a pyridine (20 mL) solution of tert-butyl 2-methylcarbamate (1.58 mL), methyl 4-(2-imino-2-methoxyethyl)benzoate monohydrochloride (2.0 g) was added at room temperature, and the mixture was stirred at the same temperature overnight. The reaction mixture was concentrated under reduced pressure, and the resulting residue was washed with a mixed solvent (hexane/ethyl acetate=1/4), thus obtaining tert-butyl 2-{2-[4-(methoxycarbonyl)phenyl]ethaneimidoyl}-1-methylhydrazine-1-carboxylate monohydrochloride (2.06 g) as a solid.

Production Example 50

To a pyridine (6.0 mL) solution of cyclopropylhydrazine dihydrochloride (392 mg), methyl 4-(2-imino-2-methoxyethyl)benzoate monohydrochloride (600 mg) was added at room temperature, and the mixture was stirred at the same temperature overnight. The reaction mixture was concentrated under reduced pressure, and formic acid (6.0 mL) was added to the resulting residue. The mixture was stirred at 105° C. for three hours and then at 110° C. for two hours. The reaction mixture was concentrated under reduced pressure, and saturated aqueous sodium hydrogen carbonate solution were added to the residue. The mixture was extracted with ethyl acetate. The organic layer was washed with saturated aqueous sodium chloride solution and dried over anhydrous magnesium sulfate. The solution was concentrated under reduced pressure, and the resulting residue was purified by silica gel column chromatography (basic silica gel, hexane/ethyl acetate), thus obtaining methyl 4-[(1-cyclopropyl-1H-1,2,4-triazol-3-yl)methyl]benzoate (210 mg) as an oily substance.

Production Example 52

To a pyridine (20 mL) solution of 1-aminopyrrolidin-2-one monohydrochloride (1.3 g), methyl 4-(2-imino-2-methoxyethyl) benzoate monohydrochloride (2.55 g) was added at room temperature. The mixture was stirred at the same temperature for an hour and then at 100° C. for three days. Toluene was added to the reaction mixture, and the mixture was concentrated under reduced pressure. The resulting residue was adsorbed onto basic silica gel and then purified by silica gel column chromatography (basic silica gel, hexane/ethyl acetate), thus obtaining methyl 4-[(6,7-dihydro-5H-pyrrolo[1,2-b][1,2,4]triazol-2-yl)methyl]benzoate (1.13 g) as a solid.

Production Example 53

Under nitrogen flow, LAH (30 mg) was added under ice cooling to a THF (4.0 mL) solution of methyl 4-[(1-cyclopropyl-1H-1,2,4-triazol-3-yl)methyl] benzoate (205 mg), and the mixture was stirred at the same temperature for 30 minutes. Sodium sulfate decahydrate (513 mg) was added in small portions to the reaction mixture under ice cooling, and the mixture was stirred at the same temperature for 10 minutes and then at room temperature for 30 minutes. The reaction mixture was filtered through celite, and the filtrate was concentrated under reduced pressure to give {4-[(1-cyclopropyl-1H-1,2,4-triazol-3-yl)methyl]phenyl}methanol (182 mg) as an oily substance.

Production Example 63

Under argon atmosphere, to a mixture of methyl 4-[(2H-tetrazol-5-yl)methyl]benzoate (3.63 g), potassium carbonate (3.5 g) and DMF (80 mL), iodomethane (5.2 mL) was added under ice cooling. The mixture was stirred at room temperature for 3 hours, and then saturated aqueous ammonium chloride solution was added under ice cooling. Ethyl acetate and water were added to the reaction mixture, and the organic layer and the aqueous layer were separated by a separation operation. The resulting aqueous layer was subjected to extraction with ethyl acetate three times. The organic layer was mixed and dried over anhydrous sodium sulfate, and the solution was concentrated under reduced pressure. The resulting residue was purified by silica gel column chromatography (expanded with hexane/ethyl acetate and followed by $CHCl_3$/MeOH), thus obtaining a mixture (3.7 g) of methyl 4-[(2-methyl-2H-tetrazol-5-yl) methyl] benzoate and a position isomer thereof as a solid.

Production Example 64

A mixture of benzyl 4-[(1H-1,2,4-triazol-3-yl)methyl] benzoate (1.85 g), cesium carbonate (3.2 g), N-methylpyrrolidone (15 mL), 3-iodooxetane (1.79 g) was stirred under microwave irradiation at 150° C. for 30 minutes. After the reaction mixture was allowed to cool to room temperature, water was added, and the mixture was extracted with ethyl acetate. The organic layer was washed with water and saturated aqueous sodium chloride solution and dried over anhydrous magnesium sulfate. The filtrate was concentrated under reduced pressure, and the resulting residue was purified by silica gel column chromatography (expanded with hexane/ethyl acetate, followed by $CHCl_3$/MeOH), thus obtaining benzyl 4-{[1-(oxetan-3-yl)-1H-1,2,4-triazol-3-yl] methyl}benzoate (1.70 g) as an oily substance.

Production Example 65

To tert-butyl 2-{2-{2-[4-(methoxycarbonyl)phenyl]ethanimidoyl}-1-methylhydrazine-1-carboxylate monohydrochloride (400 mg), DOX (4.0 mL), MeOH (4.0 mL) and hydrogen chloride (4M DOX solution, 2.8 mL) was added in this order at room temperature, and the mixture was stirred at room temperature for three hours. Hydrogen chloride (4M DOX solution, 2.8 mL) was added, and the mixture was stirred for another two hours at room temperature. The reaction mixture was concentrated under reduced pressure, and $CH_2Cl_2$ (8.0 mL) was added to the resulting residue. Under ice cooling, DIPEA (0.957 mL) and cyclopropanecarboxylic acid chloride (0.154 mL) were added, and the mixture was stirred at room temperature for an hour. The reaction mixture was concentrated under reduced pressure. M (4.0 ml) was added to the resulting residue, and the mixture was stirred at 120° C. for four hours. Aqueous sodium hydrogen carbonate solution were added to the reaction mixture, and the mixture was extracted with ethyl acetate. The combined organic layer was washed with water and saturated aqueous sodium chloride solution and dried over anhydrous magnesium sulfate. The solution was concentrated under reduced pressure, and the resulting residue was purified by silica gel column chromatography (basic silica gel, hexane/ethyl acetate), thus obtaining methyl 4-[(5-cyclopropyl-1-methyl-1H-1,2,4-triazol-3-yl)methyl] benzoate (168 mg) as an oily substance.

Production Example 69

To a mixture of 2-(5-methyl-1H-1,2,4-triazol-3-yl)pyrazine (3.9 g), methyl 4-(bromomethyl)benzoate (4.4 g) and DMF (60 mL), potassium carbonate (6.7 g) and potassium iodide (4.0 g) were added under ice cooling, and the mixture was stirred at 60° C. overnight. Saturated aqueous ammonium chloride solution was added to the reaction mixture under ice cooling, and then water and ethyl acetate was added thereto. The organic layer and the aqueous layer were separated by a separation operation, and the resulting aqueous layer was subjected to extraction twice with ethyl acetate. The organic layer was mixed and dried over anhydrous sodium sulfate, and the solution was concentrated under reduced pressure. The resulting residue was purified by silica gel column chromatography (hexane/ethyl acetate), thus obtaining methyl 4-{[5-methyl-3-(pyrazin-2-yl)-1H-1,2,4-triazol-1-yl]methyl}benzoate (1.33 g) as a solid.

Production Example 70

A mixture of 4-[(4H-1,2,4-triazol-5-yl)methyl]benzoic acid (1.0 g), 2-methyl-6-nitrobenzoic anhydride (3.7 g), TEA (1.5 mL), N,N-dimethyl-4-aminopyridine (122 mg) and $CH_2Cl_2$ (20 mL) was stirred at room temperature for 30 minutes. Then, benzyl alcohol (2.4 mL) was added, and the mixture was stirred at room temperature for an hour. Potassium carbonate (1.5 g) was added to the reaction mixture, and the mixture was stirred at room temperature for two hours. Acetic acid (0.62 mL) and water were added to the resulting reaction mixture, and the mixture was extracted with $CHCl_3$. The organic layer was dried over anhydrous magnesium sulfate, and the solution was concentrated under reduced pressure. Potassium carbonate (1.5 g), benzyl alcohol (5.0 mL) and THF (5.0 mL) were added to the resulting residue, and the mixture was stirred at 80° C. for two hours. After the reaction mixture was allowed to cool to room temperature, acetic acid (0.62 mL) and water were added, and the mixture was extracted with $CHCl_3$. The organic layer was dried over anhydrous magnesium sulfate, and the solution was concentrated under reduced pressure. The resulting residue was purified by silica gel column chromatography ($CHCl_3$/MeOH) and then solidified by adding hexane, thus obtaining benzyl 4-[(1H-1,2,4-triazol-3-yl) methyl]benzoate (1.24 g) as a solid.

Production Example 71

To a solution of tert-butyl (1S,4S)-5-{6-cyclopropyl-7-[6-fluoro-5-methyl-1-(oxan-2-yl)-1H-indazol-4-yl]-8-{[4-(hydroxymethyl)phenyl]methoxy}-2-[(oxan-4-yl)oxy]quinazolin-4-yl}-2,5-diazabicyclo[2.2.1]heptane-2-carboxylate (400 mg) in $CH_2Cl_2$ (5.0 mL), DIPEA (0.30 mL) and methanesulfonic anhydride (210 mg) were added under ice cooling, and the mixture was stirred at the same temperature for an hour. Water was added to the reaction mixture under ice cooling. The organic layer and the aqueous layer were separated by a separation operation, and the aqueous layer was subjected to extraction with $CH_2Cl_2$ three times. The resulting organic layer was mixed and then dried over anhydrous sodium sulfate, and the solution was concentrated under reduced pressure. Separately, to a solution of 4-methyl-3,4-dihydropyridine[2,3-b]pyrazin-2(1H)-one (196 mg) in DMF (5.0 mL), sodium hydride (about 60% mineral oil dispersion, 48 mg) was added under ice cooling, and the mixture was stirred at the same temperature for 10 minutes under argon atmosphere. A solution of the concentrated residue in DMF (5.0 mL) was added to the resulting reaction mixture under ice cooling, and then the mixture was stirred at room temperature overnight. Saturated aqueous ammonium chloride solution and ethyl acetate were added to the reaction mixture under ice cooling. The organic layer and the aqueous layer were separated by a separation operation, and the aqueous layer was subjected to extraction twice with ethyl acetate. The resulting organic layers were mixed and then dried over anhydrous sodium sulfate, and the solution was concentrated under reduced pressure. The resulting residue was purified by silica gel column chromatography ($CHCl_3$/MeOH), thus obtaining tert-butyl (1S,4S)-5-{6-cyclopropyl-7-[6-fluoro-5-methyl-1-(oxan-2-yl)-1H-indazol-4-yl]-8-({4-[(4-methyl-2-oxo-3,4-dihydropyrido[2,3-b]pyrazin-1(2H)-yl)methyl]phenyl}methoxy)-2-[(oxan-4-yl)oxy]quinazolin-4-yl}-2,5-diazabicyclo[2.2.1]heptane-2-carboxylate (250 mg) as a foam-like solid.

In the same manner as in the production methods of the Production Examples described above, the compounds shown in Tables 4 to 29 below were produced. In addition, the production methods, the structures and the physiochemical data of the compounds of the Production Examples are shown in Tables 4 to 29.

Example 1

Trifluoroacetic acid (13 mL) was added to a mixture of tert-butyl (1S,4S)-5-{6-cyclopropyl-7-[6-fluoro-5-methyl-1-(oxan-2-yl)-1H-indazol-4-yl]-8-({4-[(3-methyl-2-oxo-2,3-dihydro-1H-imidazo[4,5-b]pyrazin-1-yl)methyl]phenyl}methoxy)-2-[(oxan-4-yl)oxy]quinazolin-4-yl}-2,5-diazabicyclo[2.2.1]heptane-2-carboxylate (7.88 g), triisopropylsilane (3.0 mL) and $CH_2Cl_2$ (30 mL) at room temperature, and then the mixture was stirred overnight. The resulting reaction mixture was concentrated under reduced pressure to give a mixture containing two diastereomers of 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-3-methyl-1,3-dihydro-2H-imidazo[4,5-b]pyrazin-2-one. The obtained mixture was purified by ODS column chromatography (MeCN/0.10% aqueous formic acid solution), thus obtaining a fraction containing (1) a high-polarity diastereomer (peak-1) and (2) a low-polarity diastereomer (peak-2). A saturated aqueous sodium hydrogen carbonate solution was added to a fraction containing the low-polarity diastereomer (peak-2), and the mixture was extracted with a mixed solvent ($CHCl_3$/MeOH=4/1). The organic layer was dried over anhydrous sodium sulfate and concentrated under reduced pressure, thus obtaining a low-polarity diastereomer (2.39 g) of 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-3-methyl-1,3-dihydro-2H-imidazo[4,5-b]pyrazin-2-one as a solid.

In the same manner as in the production methods of the Examples described above, the compounds shown in Tables 30 to 37 below were produced. In addition, the structures of the compounds of the Examples are shown in Tables 30 to 37 below, and the physiochemical data of the compounds of the Examples are shown in Table 38.

In the tables presented below, the following abbreviations are sometimes used. PEx: Production Example No., Ex: Example No., PSyn: Production Example No. produced by the same method, Syn: Example No. produced by the same method (for example, 1 represents Example 1), Str: chemical structural formula (A compound with "*" in the chemical structural formula represents that the compound is a single diastereomer based on axial chirality and a low-polarity diastereomer (peak-2) under separation conditions for ODS column chromatography (MeCN/0.1% aqueous formic acid solution). A compound with "#" in the chemical structural formula represents a mixture of position isomers), DAT: physiochemical data, ESI+: m/z value in mass spectrometry (ionization method ESI, $[M+H]^+$ unless otherwise specified), NMR: δ value (ppm) of peak in $^1H$-NMR (500 MHz) in DMSO-$d_6$, s: singlet (spectrum), d: doublet (spectrum), t: triplet (spectrum), m: multiplet (spectrum), br: broad (spectrum) (example: br s).

TABLE 4

| PEx | PSyn | Str | DAT |
|---|---|---|---|
| 1 | 1 | 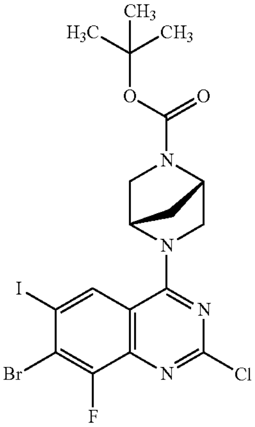 [SMILES: CC(C)(C)OC(=O)N1C[C@@H]2C[C@H]1CN2c1nc(Cl)nc2c(F)c(Br)c(I)cc12] | ESI+: 583.1, 585.1 |
| 2 | 2 | 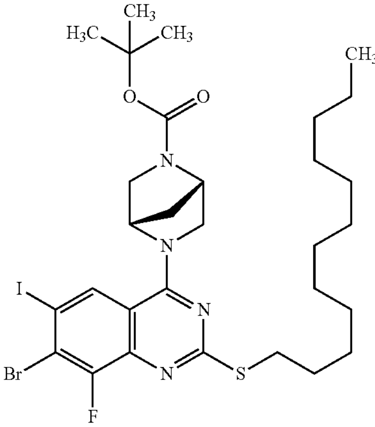 [SMILES: CCCCCCCCCCCCSc1nc(N2C[C@@H]3C[C@H]2CN3C(=O)OC(C)(C)C)c2cc(I)c(Br)c(F)c2n1] | ESI+: 751.3 |
| 3 | 2 | 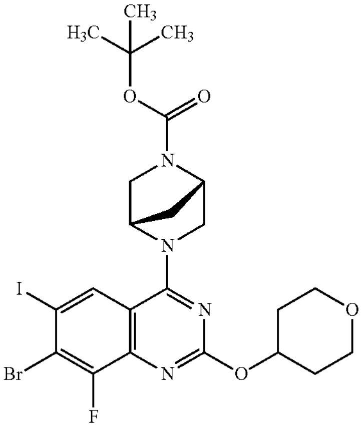 [SMILES: CC(C)(C)OC(=O)N1C[C@@H]2C[C@H]1CN2c1nc(OC2CCOCC2)nc2c(F)c(Br)c(I)cc12] | ESI+: 651.0 |

TABLE 5
| PEx | PSyn | Str | DAT |
|---|---|---|---|
| 4 | 4 | 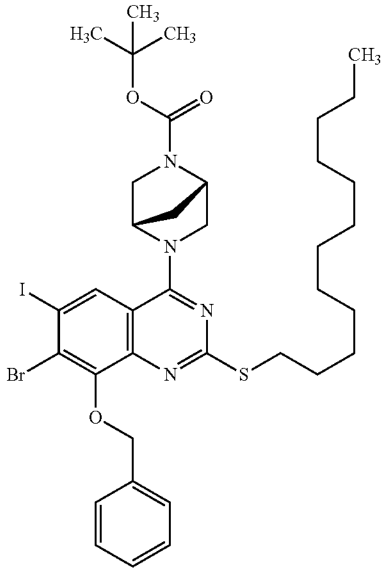 [SMILES: CCCCCCCCCCCCSc1nc(N2C[C@@H]3C[C@H]2CN3C(=O)OC(C)(C)C)c2cc(I)c(Br)c(OCc3ccccc3)c2n1] | ESI+: 837.5 |
| 5 | 4 | 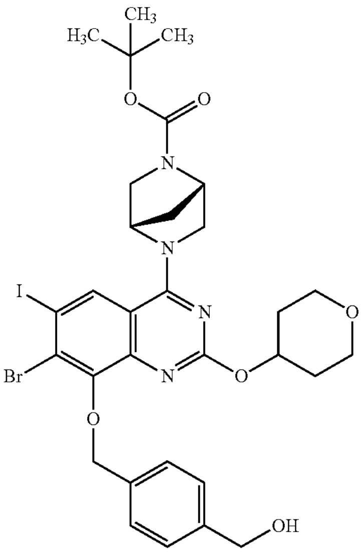 [SMILES: CC(C)(C)OC(=O)N1C[C@@H]2C[C@H]1CN2c1nc(OC2CCOCC2)nc2c(OCc3ccc(CO)cc3)c(Br)c(I)cc12] | ESI+: 769.3 |
TABLE 6
| PEx | PSyn | Str | DAT |
|---|---|---|---|
| 6 | 4 | 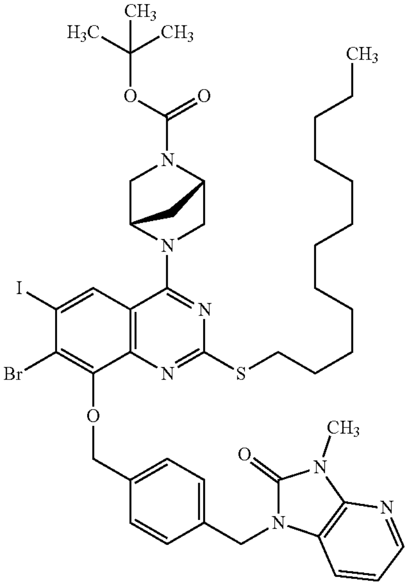 [SMILES: CCCCCCCCCCCCSc1nc(N2C[C@@H]3C[C@H]2CN3C(=O)OC(C)(C)C)c2cc(I)c(Br)c(OCc3ccc(Cn4c(=O)n(C)c5ncccc54)cc3)c2n1] | ESI+: 998.4, 1000.3 |
| 7 | 7 | 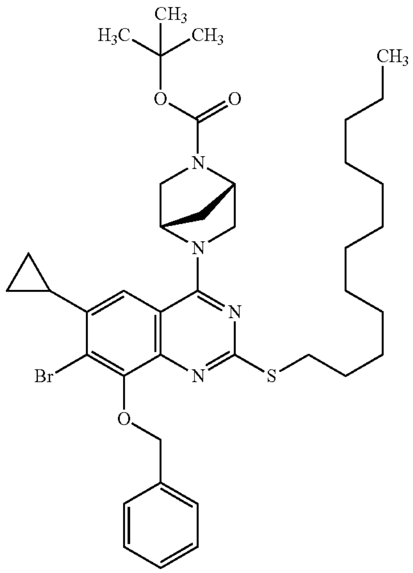 [SMILES: CCCCCCCCCCCCSc1nc(N2C[C@@H]3C[C@H]2CN3C(=O)OC(C)(C)C)c2cc(C3CC3)c(Br)c(OCc3ccccc3)c2n1] | ESI+: 753.5 |

TABLE 7
| PEX | PSyn | Str | DAT |
|---|---|---|---|
| 8 | 7 | 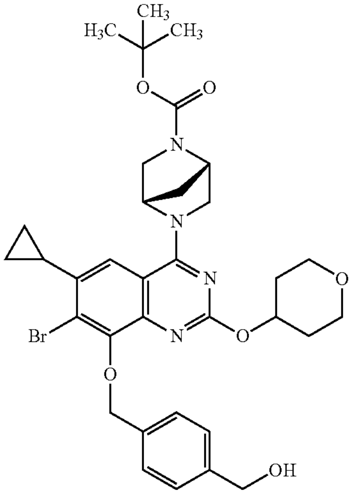 [SMILES: CC(C)(C)OC(=O)N1C[C@@H]2C[C@H]1CN2c1nc(OC2CCOCC2)nc2c(OCc3ccc(CO)cc3)c(Br)c(C3CC3)cc12] | ESI+: 683.3 |
| 9 | 7 | 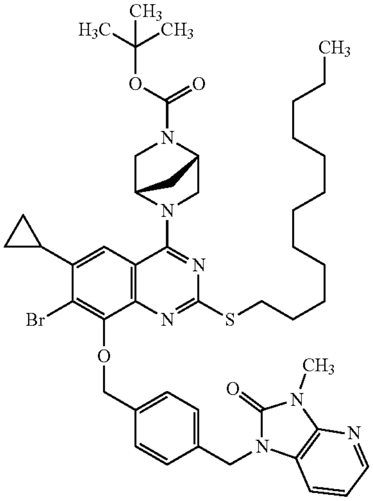 [SMILES: CCCCCCCCCCCCSc1nc(N2C[C@@H]3C[C@H]2CN3C(=O)OC(C)(C)C)c2cc(C3CC3)c(Br)c(OCc3ccc(Cn4c(=O)n(C)c5ncccc54)cc3)c2n1] | ESI+: 912.7, 914.6 |
TABLE 8
| PEx | PSyn | Str | DAT |
|---|---|---|---|
| 10 | 10 | 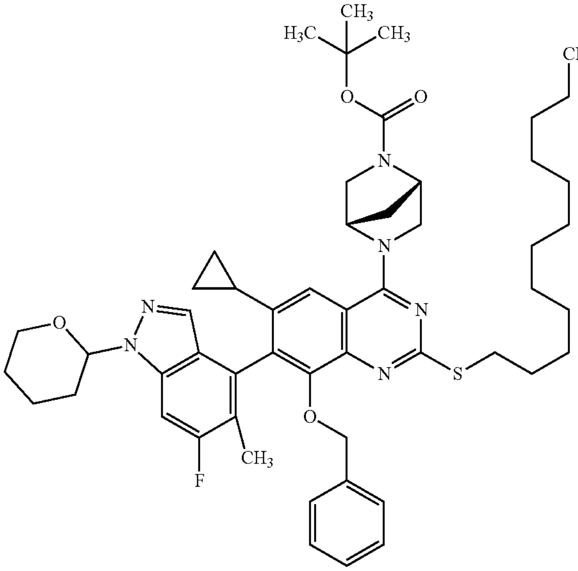 | ESI+: 905.8 |

TABLE 8-continued
| PEx | PSyn | Str | DAT |
|---|---|---|---|
| 11 | 10 | 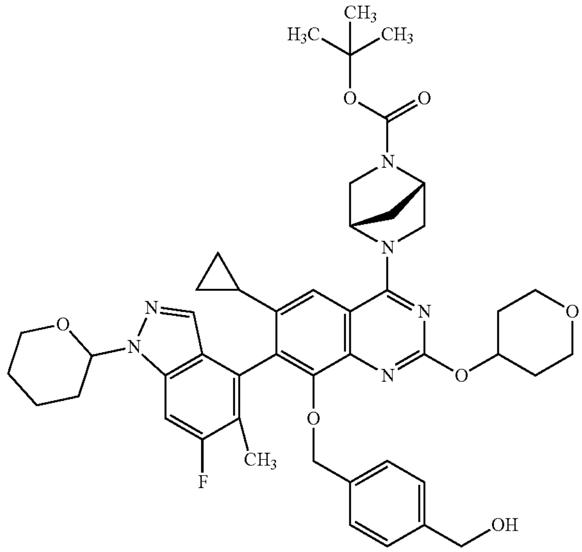 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CO)cc1] | ESI+: 835.7 |
TABLE 9
| PEx | PSyn | Str | DAT |
|---|---|---|---|
| 12 | 10 | 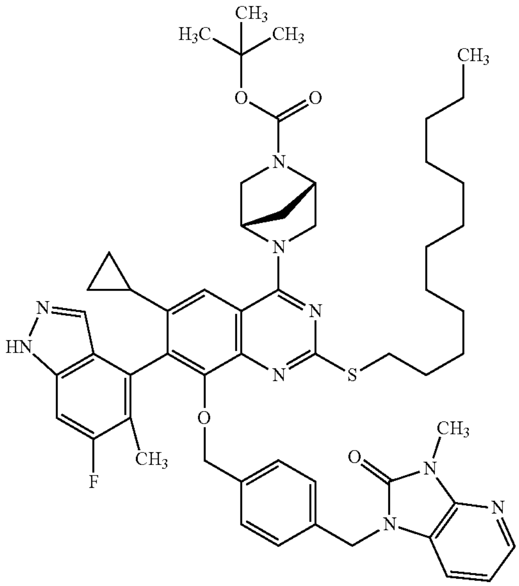 [SMILES: CCCCCCCCCCCCSc1nc(N2C[C@@H]3C[C@H]2CN3C(=O)OC(C)(C)C)c2cc(C3CC3)c(-c3c(C)c(F)cc4[nH]ncc34)c(OCc3ccc(Cn4c(=O)n(C)c5ncccc54)cc3)c2n1] | ESI+: 982.8 |

TABLE 9-continued
| PEx | PSyn | Str | DAT |
|---|---|---|---|
| 13 | 13 | 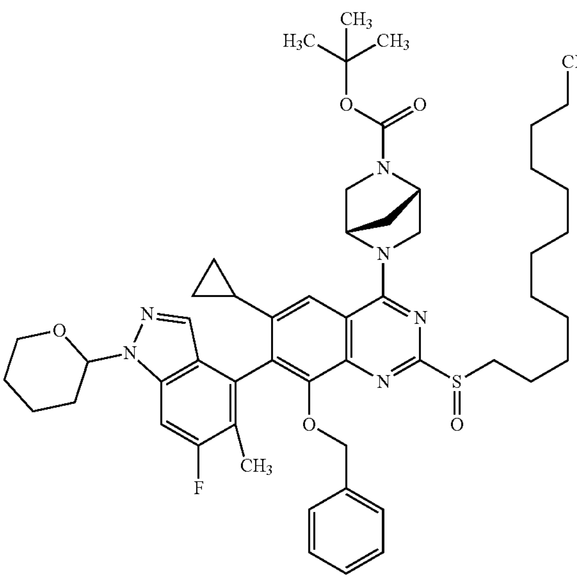 | ESI+: 921.8 |
TABLE 10
| PEx | PSyn | Str | DAT |
|---|---|---|---|
| 14 | 13 | 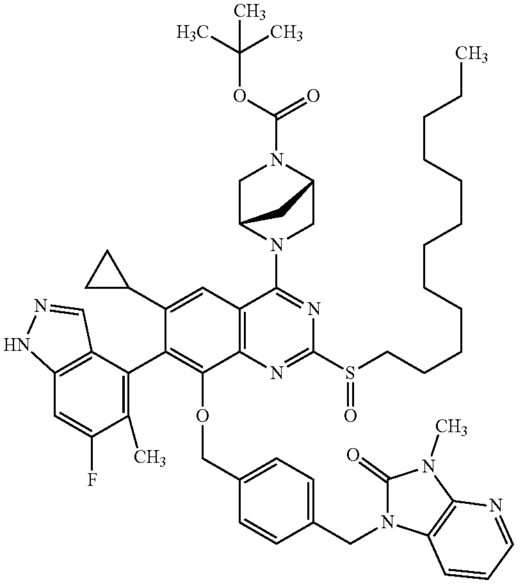 [SMILES: CCCCCCCCCCCCS(=O)c1nc(N2C[C@@H]3C[C@H]2CN3C(=O)OC(C)(C)C)c2cc(C3CC3)c(-c3c(C)c(F)cc4[nH]ncc34)c(OCc3ccc(Cn4c(=O)n(C)c5ncccc54)cc3)c2n1] | ESI+: 998.6 |

TABLE 10-continued
| PEx | PSyn | Str | DAT |
| --- | --- | --- | --- |
| 15 | 15 | 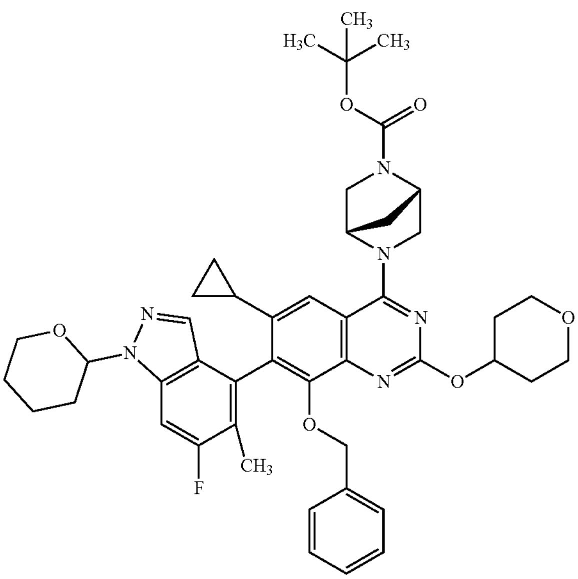 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccccc1] | ESI+: 805.7 |
TABLE 11
| PEx | PSyn | Str | DAT |
| --- | --- | --- | --- |
| 16 | 15 | 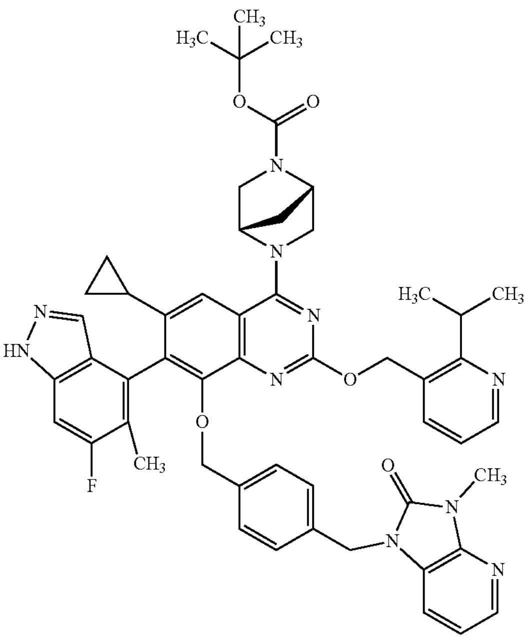 [SMILES: Cc1c(F)cc2[nH]ncc2c1-c1c(C2CC2)cc2c(N3C[C@@H]4C[C@H]3CN4C(=O)OC(C)(C)C)nc(OCc3cccnc3C(C)C)nc2c1OCc1ccc(Cn2c(=O)n(C)c3ncccc32)cc1] | ESI+: 931.8 |

TABLE 11-continued
| PEx | PSyn | Str | DAT |
|---|---|---|---|
| 17 | 15 | 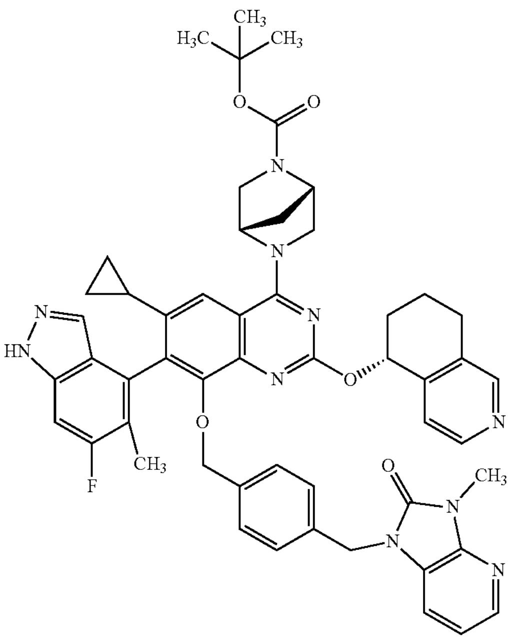 [SMILES: Cc1c(F)cc2[nH]ncc2c1-c1c(C2CC2)cc2c(N3C[C@@H]4C[C@H]3CN4C(=O)OC(C)(C)C)nc(O[C@@H]3CCCc4cnccc43)nc2c1OCc1ccc(Cn2c(=O)n(C)c3ncccc32)cc1] | ESI+: 929.6 |
TABLE 12
| PEx | PSyn | Str | DAT |
|---|---|---|---|
| 18 | 18 | 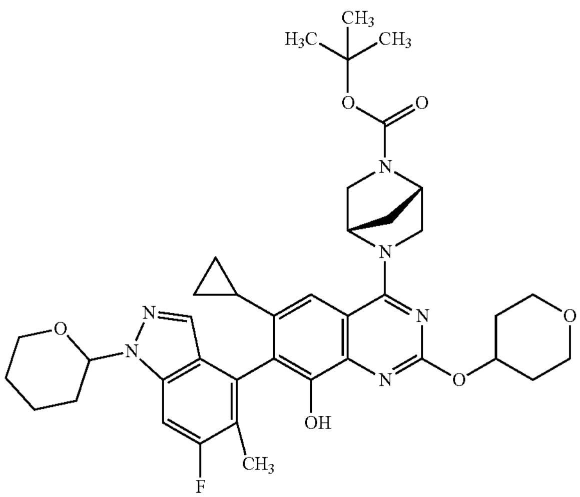 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1O] | ESI+: 715.5 |

TABLE 12-continued
| PEx | PSyn | Str | DAT |
| --- | --- | --- | --- |
| 19 | 19 | 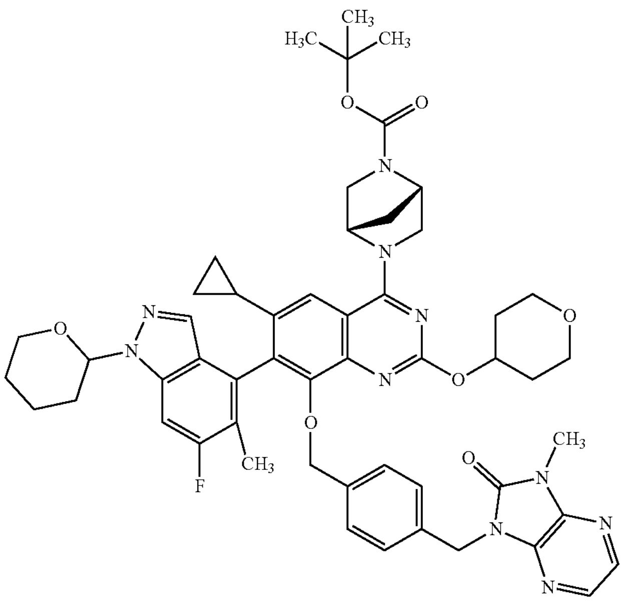 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cn2c(=O)n(C)c3nccnc32)cc1] | ESI+: 967.8 |
TABLE 13
| PEx | PSyn | Str | DAT |
| --- | --- | --- | --- |
| 20 | 19 | 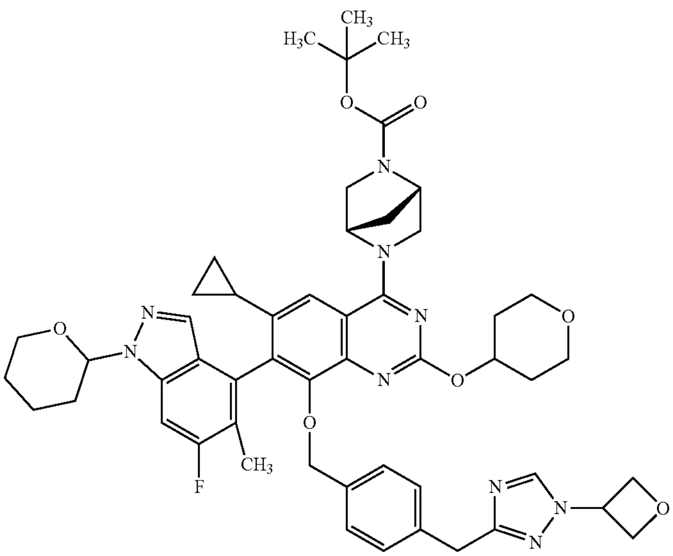 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2ncn(C3COC3)n2)cc1] | ESI+: 942.7 |

TABLE 13-continued
| PEx | PSyn | Str | DAT |
| --- | --- | --- | --- |
| 21 | 19 | 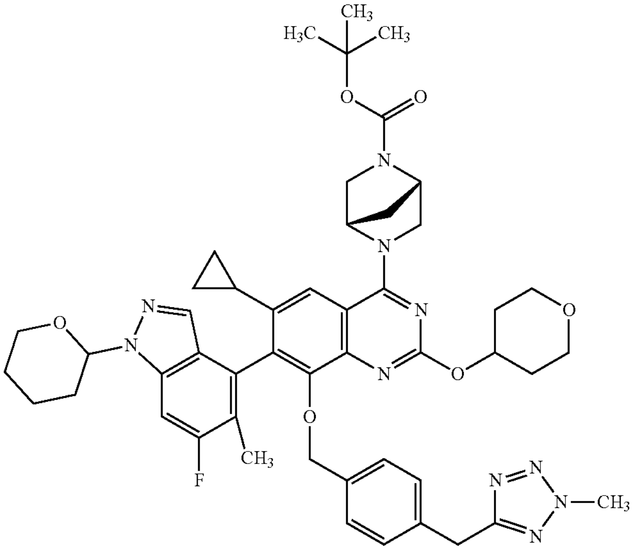 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nnn(C)n2)cc1] | ESI+: 901.7 |
TABLE 14
| PEx | PSyn | Str | DAT |
| --- | --- | --- | --- |
| 22 | 19 | 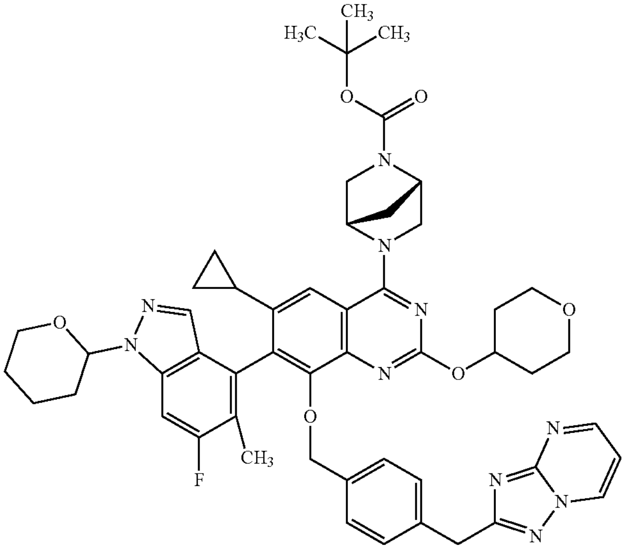 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nc3ncccn3n2)cc1] | ESI+: 937.7 |

TABLE 14-continued
| PEx | PSyn | Str | DAT |
|---|---|---|---|
| 23 | 19 | 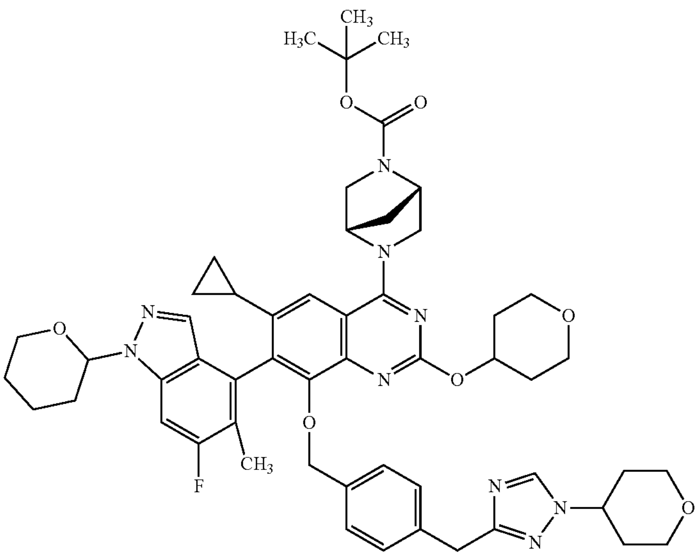 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2ncn(C3CCOCC3)n2)cc1] | ESI+: 970.7 |
TABLE 15
| PEx | PSyn | Str | DAT |
|---|---|---|---|
| 24 | 19 | 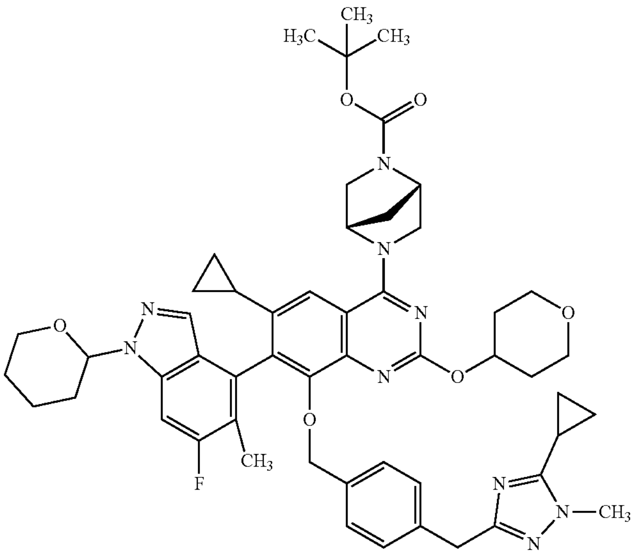 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nc(C3CC3)n(C)n2)cc1] | ESI+: 940.8 |

TABLE 15-continued
| PEx | PSyn | Str | DAT |
| --- | --- | --- | --- |
| 25 | 19 | 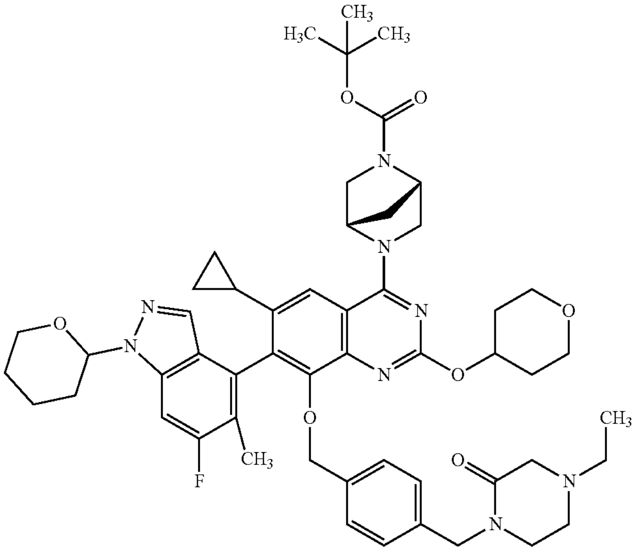 [SMILES: CCN1CCN(Cc2ccc(COc3c(-c4c(C)c(F)cc5c4cnn5C4CCCCO4)c(C4CC4)cc4c(N5C[C@@H]6C[C@H]5CN6C(=O)OC(C)(C)C)nc(OC5CCOCC5)nc34)cc2)C(=O)C1] | ESI+: 945.6 |
TABLE 16
| PEx | PSyn | Str | DAT |
| --- | --- | --- | --- |
| 26 | 19 | 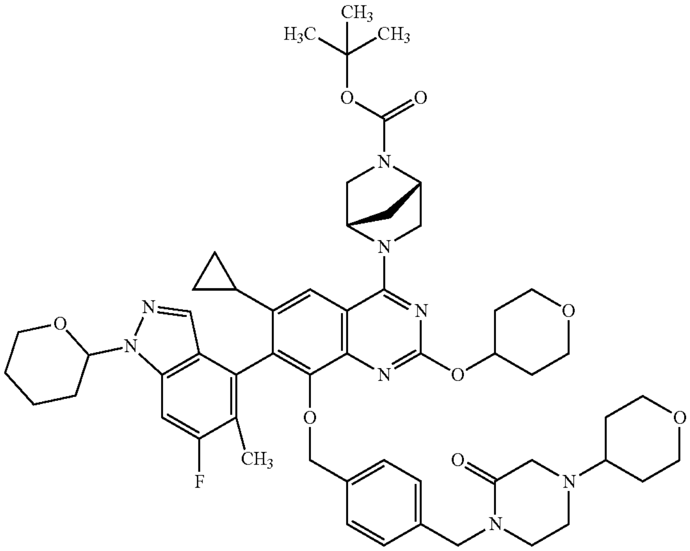 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CN2CCN(C3CCOCC3)CC2=O)cc1] | ESI+: 1001.8 |

TABLE 16-continued
| PEx | PSyn | Str | DAT |
| --- | --- | --- | --- |
| 27 | 19 | 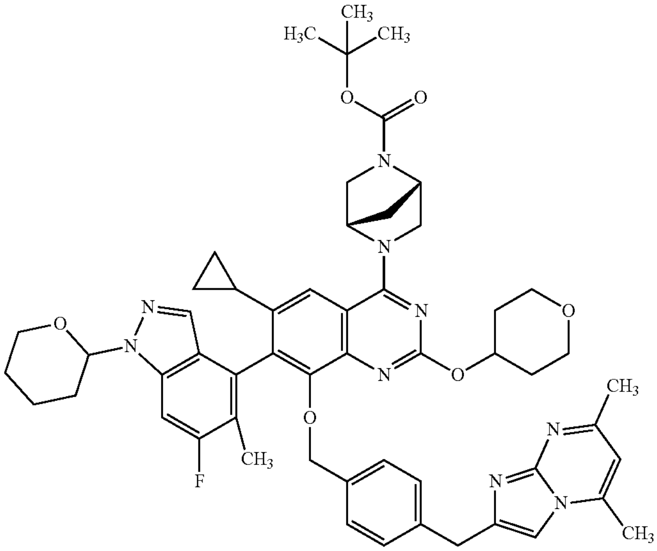 [SMILES: Cc1cc(C)n2cc(Cc3ccc(COc4c(-c5c(C)c(F)cc6c5cnn6C5CCCCO5)c(C5CC5)cc5c(N6C[C@@H]7C[C@H]6CN7C(=O)OC(C)(C)C)nc(OC6CCOCC6)nc45)cc3)nc2n1] | ESI+: 986.7 [M + Na]+ |
TABLE 17
| PEx | PSyn | Str | DAT |
| --- | --- | --- | --- |
| 28 | 19 | 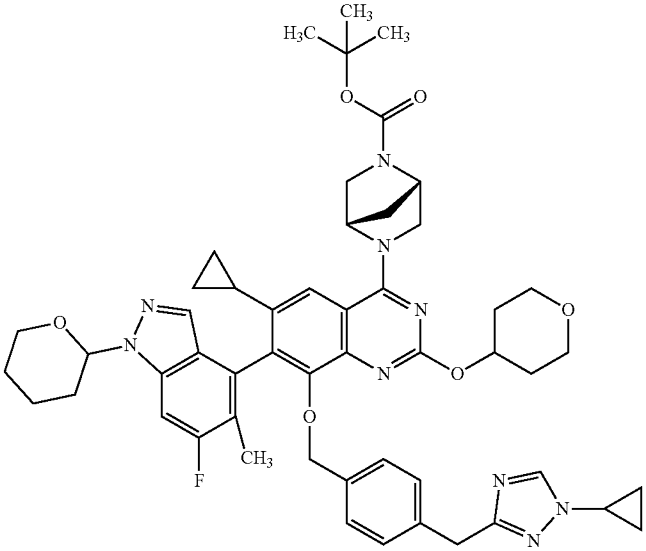 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2ncn(C3CC3)n2)cc1] | ESI+: 926.7 |

TABLE 17-continued
| PEx | PSyn | Str | DAT |
| --- | --- | --- | --- |
| 29 | 19 | 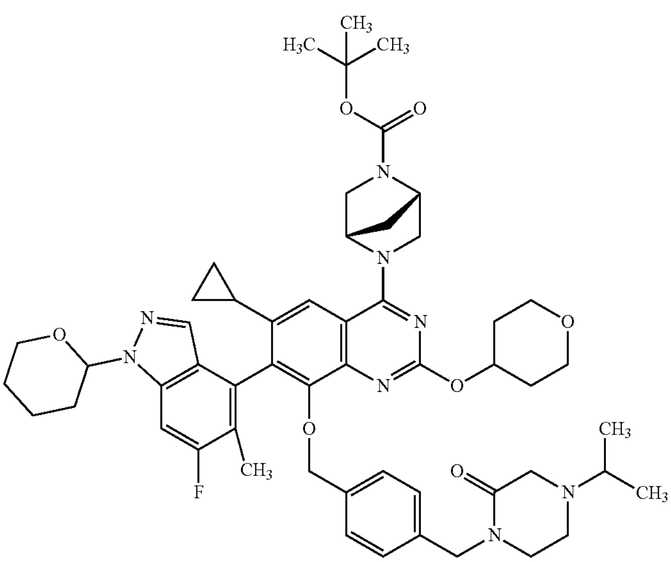 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CN2CCN(C(C)C)CC2=O)cc1] | ESI+: 959.7 |
TABLE 18
| PEx | PSyn | Str | DAT |
| --- | --- | --- | --- |
| 30 | 19 | 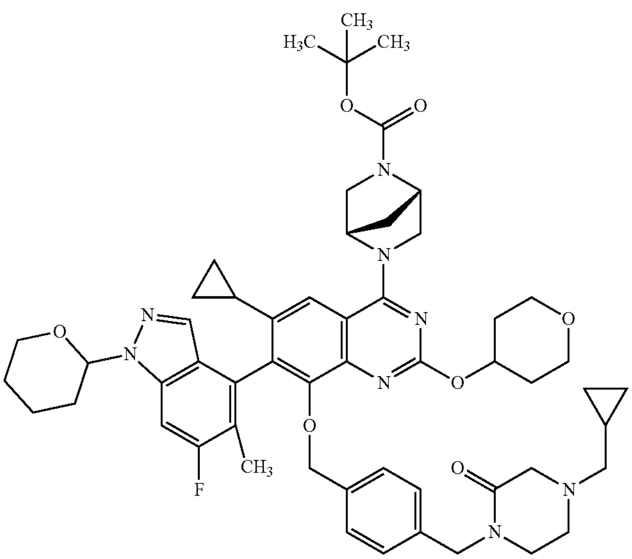 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CN2CCN(CC3CC3)CC2=O)cc1] | ESI+: 971.6 |

TABLE 18-continued
| PEx | PSyn | Str | DAT |
|---|---|---|---|
| 31 | 19 | 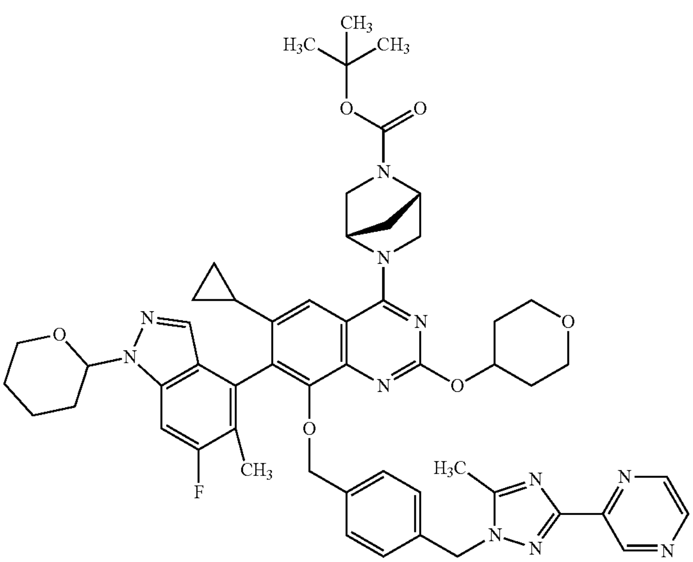 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cn2nc(-c3cnccn3)nc2C)cc1] | ESI+: 1000.7 [M + Na]+ |
TABLE 19
| PEx | PSyn | Str | DAT |
|---|---|---|---|
| 32 | 19 | 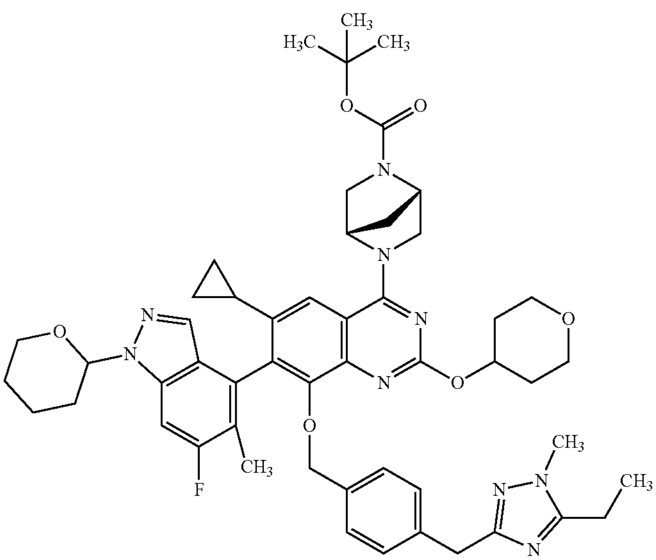 [SMILES: CCc1nc(Cc2ccc(COc3c(-c4c(C)c(F)cc5c4cnn5C4CCCCO4)c(C4CC4)cc4c(N5C[C@@H]6C[C@H]5CN6C(=O)OC(C)(C)C)nc(OC5CCOCC5)nc34)cc2)nn1C] | ESI+: 928.6 |

TABLE 19-continued
| PEx | PSyn | Str | DAT |
|---|---|---|---|
| 33 | 19 | 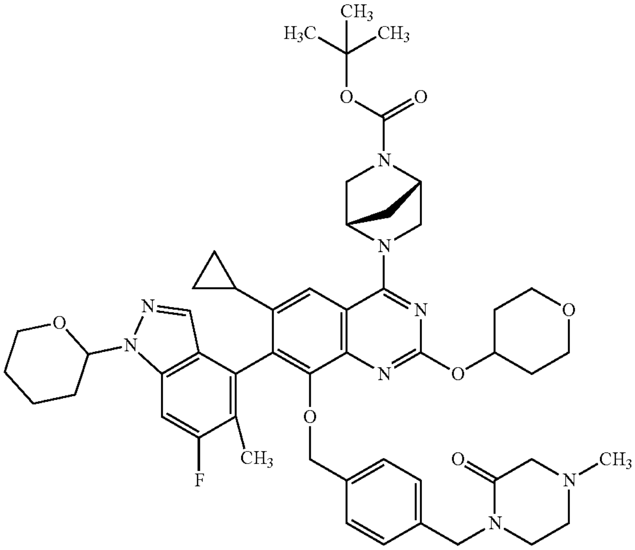 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CN2CCN(C)CC2=O)cc1] | ESI+: 931.7 |
TABLE 20
| PEx | PSyn | Str | DAT |
|---|---|---|---|
| 34 | 19 | 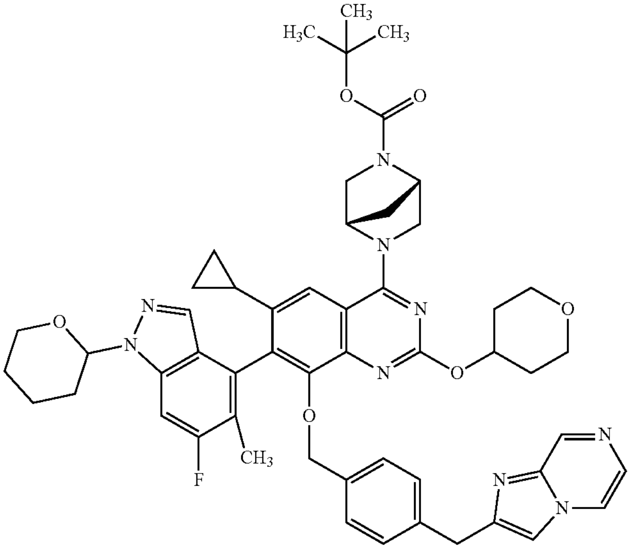 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2cn3ccncc3n2)cc1] | ESI+: 936.7 |

TABLE 20-continued
| PEx | PSyn | Str | DAT |
|---|---|---|---|
| 35 | 19 | 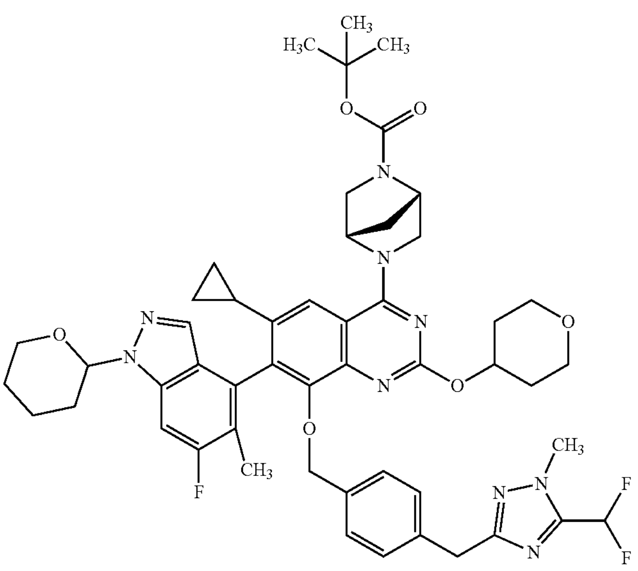 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nc(C(F)F)n(C)n2)cc1] | ESI+: 950.7 |
TABLE 21
| PEx | PSyn | Str | DAT |
|---|---|---|---|
| 36 | 19 | 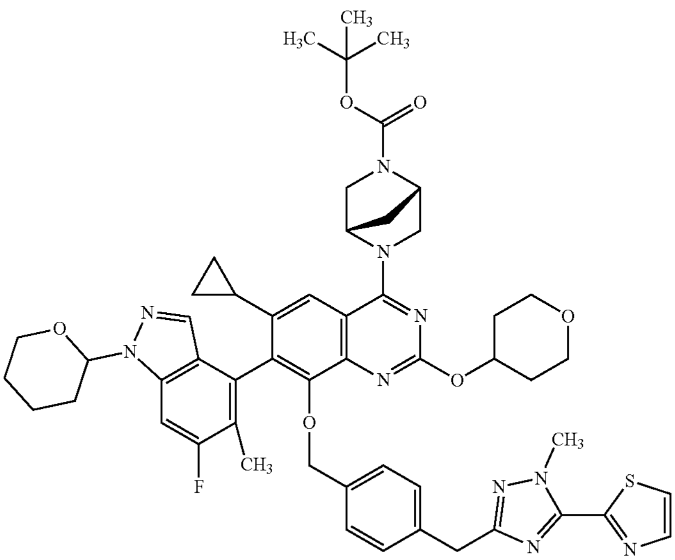 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nc(-c3nccs3)n(C)n2)cc1] | ESI+: 983.7 |

TABLE 21-continued
| PEx | PSyn | Str | DAT |
|---|---|---|---|
| 37 | 19 | 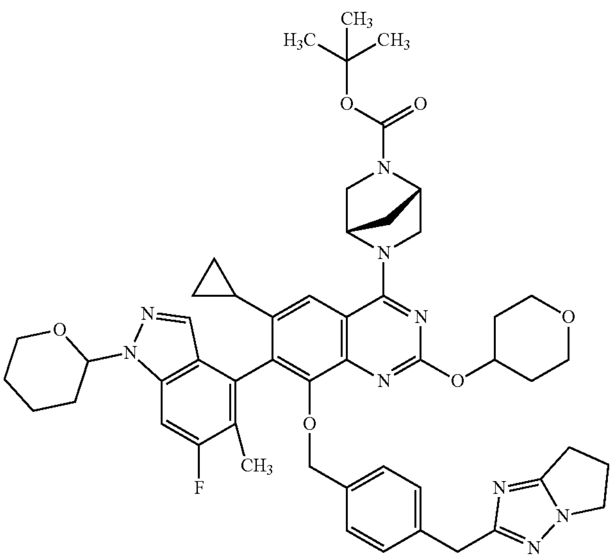 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cc2nc3n(n2)CCC3)cc1] | ESI+: 926.7 |
TABLE 22
| PEx | PSyn | Str | DAT |
|---|---|---|---|
| 38 | 38 | 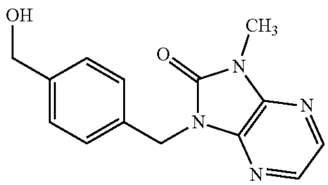 [SMILES: Cn1c(=O)n(Cc2ccc(CO)cc2)c2nccnc21] | ESI+: 271.3 |
| 39 | 38 | 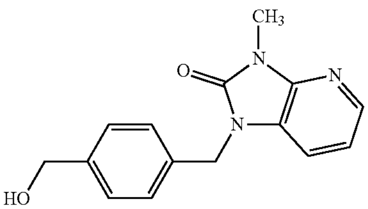 [SMILES: Cn1c(=O)n(Cc2ccc(CO)cc2)c2cccnc21] | ESI+: 270.2 |
| 40 | 38 | 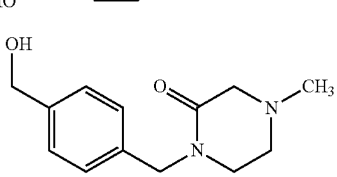 | ESI+: 235.3 |
TABLE 23
| PEx | PSyn | Str | DAT |
|---|---|---|---|
| 41 | 38 | 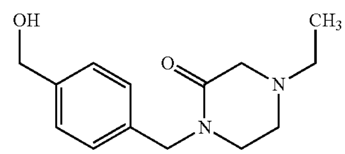 [SMILES: CCN1CCN(Cc2ccc(CO)cc2)C(=O)C1] | ESI+: 249.3 |

TABLE 23-continued
| PEx | PSyn | Str | DAT |
|---|---|---|---|
| 42 | 38 | 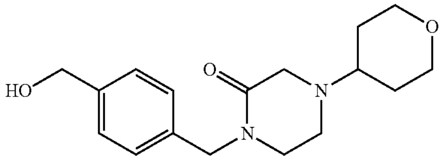 [SMILES: O=C1CN(C2CCOCC2)CCN1Cc1ccc(CO)cc1] | ESI+: 305.3 |
| 43 | 38 | 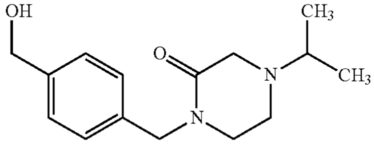 [SMILES: CC(C)N1CCN(Cc2ccc(CO)cc2)C(=O)C1] | ESI+: 263.4 |
| 44 | 38 | 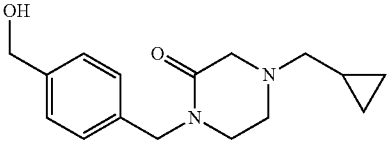 [SMILES: O=C1CN(CC2CC2)CCN1Cc1ccc(CO)cc1] | ESI+: 275.4 |
| 45 | 45 | 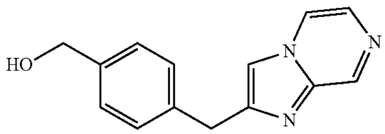 [SMILES: OCc1ccc(Cc2cn3ccncc3n2)cc1] | ESI+: 240.3 |
| 46 | 45 | 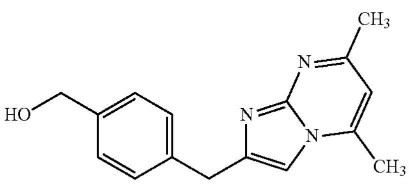 [SMILES: Cc1cc(C)n2cc(Cc3ccc(CO)cc3)nc2n1] | ESI+: 268.4 |
TABLE 24
| PEx | PSyn | Str | DAT |
|---|---|---|---|
| 47 | 45 | 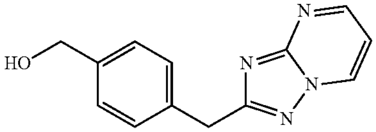 [SMILES: OCc1ccc(Cc2nc3ncccn3n2)cc1] | ESI+: 241.4 |
| 48 | 48 | 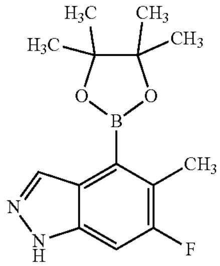 [SMILES: Cc1c(F)cc2[nH]ncc2c1B1OC(C)(C)C(C)(C)O1] | ESI+: 277.3 |

TABLE 24-continued
| PEx | PSyn | Str | DAT |
|---|---|---|---|
| 49 | 49 | 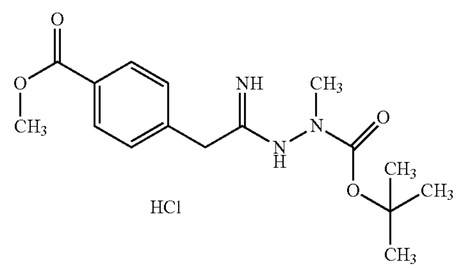 HCl | ESI+: 322.6 |
| 50 | 50 | 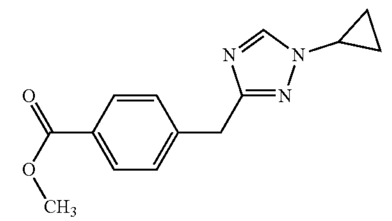 [SMILES: COC(=O)c1ccc(Cc2ncn(C3CC3)n2)cc1] | ESI+: 258.4 |
| 51 | 50 | 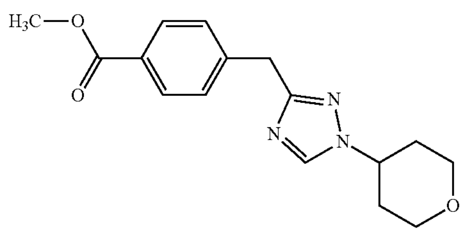 [SMILES: COC(=O)c1ccc(Cc2ncn(C3CCOCC3)n2)cc1] | ESI+: 302.3 |
TABLE 25
| PEx | PSyn | Str | DAT |
|---|---|---|---|
| 52 | 52 | 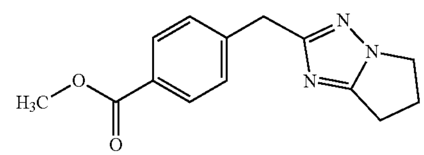 [SMILES: COC(=O)c1ccc(Cc2nc3n(n2)CCC3)cc1] | ESI+: 258.3 |
| 53 | 53 | 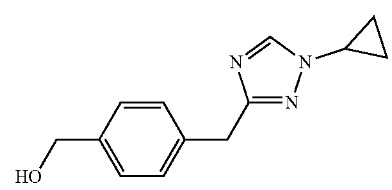 [SMILES: OCc1ccc(Cc2ncn(C3CC3)n2)cc1] | ESI+: 230.4 |
| 54 | 53 | 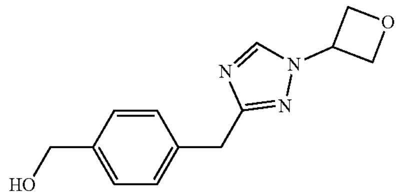 [SMILES: OCc1ccc(Cc2ncn(C3COC3)n2)cc1] | ESI+: 246.4 |
| 55 | 53 | 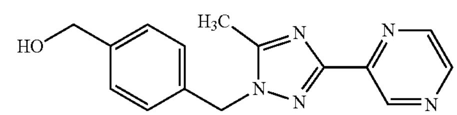 [SMILES: Cc1nc(-c2cnccn2)nn1Cc1ccc(CO)cc1] | ESI+: 282.3 |

TABLE 25-continued
| PEx | PSyn | Str | DAT |
|---|---|---|---|
| 56 | 53 | 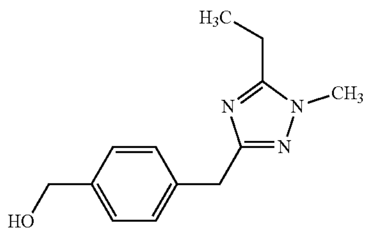 [SMILES: CCc1nc(Cc2ccc(CO)cc2)nn1C] | ESI+: 232.2 |
| 57 | 53 | 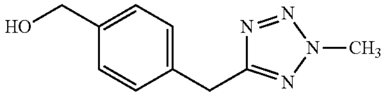 | ESI+: 205.3 |
TABLE 26
| PEx | PSyn | Str | DAT |
|---|---|---|---|
| 58 | 53 | 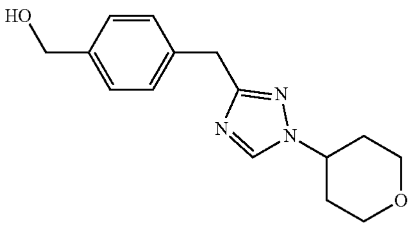 [SMILES: OCc1ccc(Cc2ncn(C3CCOCC3)n2)cc1] | ESI+: 274.4 |
| 59 | 53 | 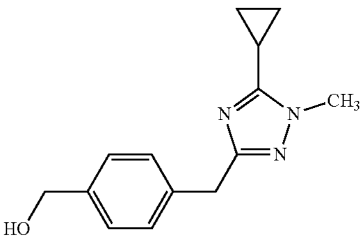 [SMILES: Cn1nc(Cc2ccc(CO)cc2)nc1C1CC1] | ESI+: 244.4 |
| 60 | 53 | 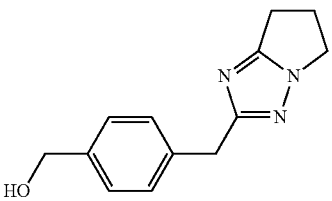 [SMILES: OCc1ccc(Cc2nc3n(n2)CCC3)cc1] | ESI+: 230.4 |
TABLE 26-continued
| PEx | PSyn | Str | DAT |
|---|---|---|---|
| 61 | 53 | 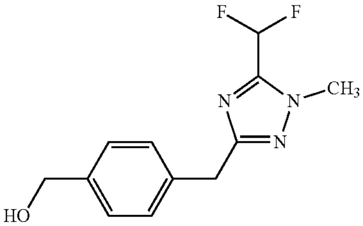 [SMILES: Cn1nc(Cc2ccc(CO)cc2)nc1C(F)F] | ESI+: 254.3 |
| 62 | 53 | 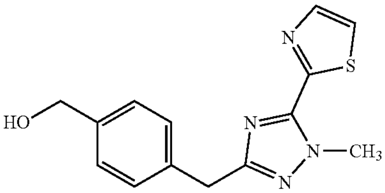 [SMILES: Cn1nc(Cc2ccc(CO)cc2)nc1-c1nccs1] | ESI+: 287.3 |
TABLE 27
| PEx | PSyn | Str | DAT |
|---|---|---|---|
| 63 | 63 | 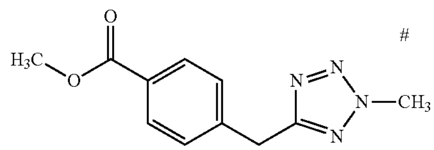 # | ESI+: 233.2 |

TABLE 27-continued
| PEx | PSyn | Str | DAT |
|---|---|---|---|
| 64 | 64 | 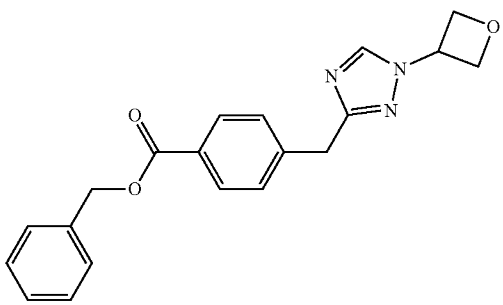 [SMILES: O=C(OCc1ccccc1)c1ccc(Cc2ncn(C3COC3)n2)cc1] | ESI+: 350.3 |
| 65 | 65 | 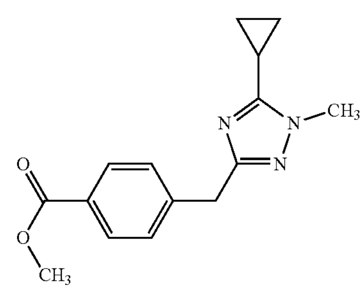 [SMILES: COC(=O)c1ccc(Cc2nc(C3CC3)n(C)n2)cc1] | ESI+: 272.3 |
| 66 | 65 | 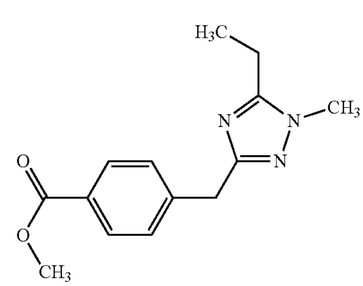 [SMILES: CCc1nc(Cc2ccc(C(=O)OC)cc2)nn1C] | ESI+: 260.2 |
| 67 | 65 | 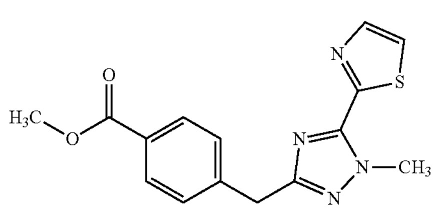 | ESI+: 315.3 |
TABLE 28
| PEx | PSyn | Str | DAT |
|---|---|---|---|
| 68 | 65 | 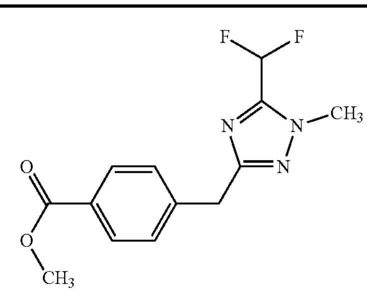 | ESI+: 282.3 |

TABLE 28-continued
| PEx | PSyn | Str | DAT |
| --- | --- | --- | --- |
| 69 | 69 | 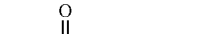 | ESI+: 310.3 |
| 70 | 70 | 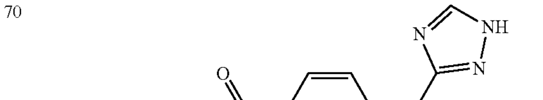 | ESI+: 294.2 |
TABLE 29
| PEx | PSyn | Str | DAT |
| --- | --- | --- | --- |
| 71 | 71 | 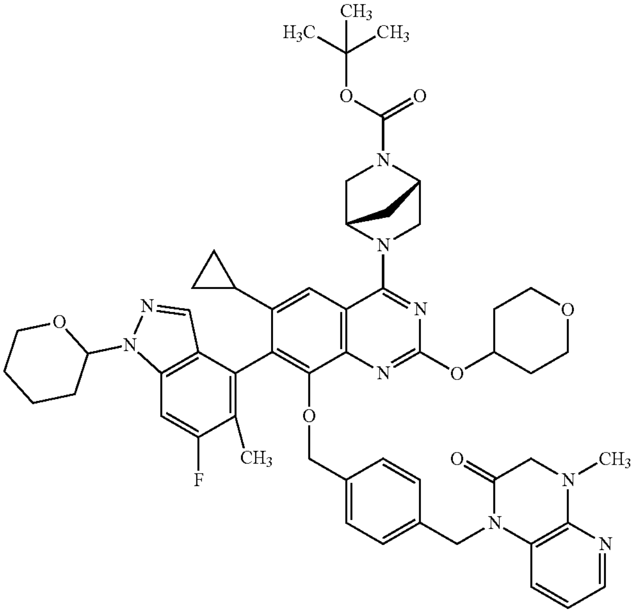 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(CN2C(=O)CN(C)c3ncccc32)cc1] | ESI+: 980.9 |

TABLE 29-continued
| PEx | PSyn | Str | DAT |
|---|---|---|---|
| 72 | 71 | 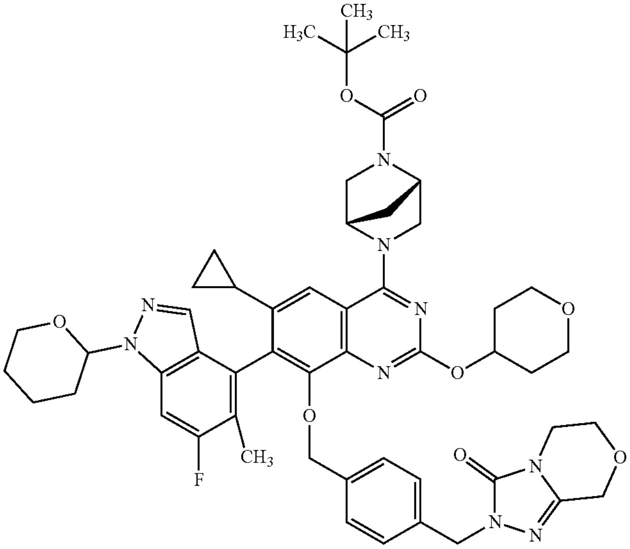 [SMILES: Cc1c(F)cc2c(cnn2C2CCCCO2)c1-c1c(C2CC2)cc2c(N3C[C@@H]4C[C@H]3CN4C(=O)OC(C)(C)C)nc(OC3CCOCC3)nc2c1OCc1ccc(Cn2nc3n(c2=O)CCOC3)cc1] | ESI+: 958.8 |
TABLE 30
| Ex | Str |
|---|---|
| 1 | 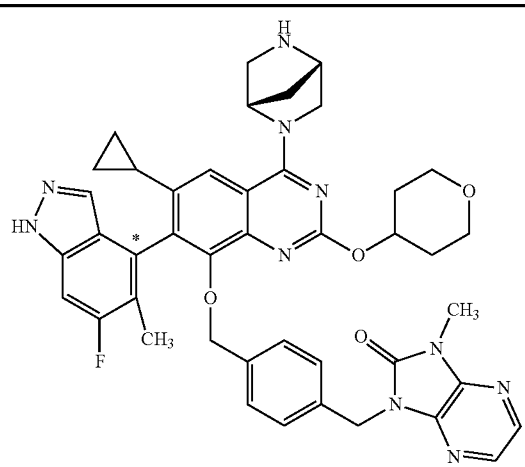 |
| 2 | 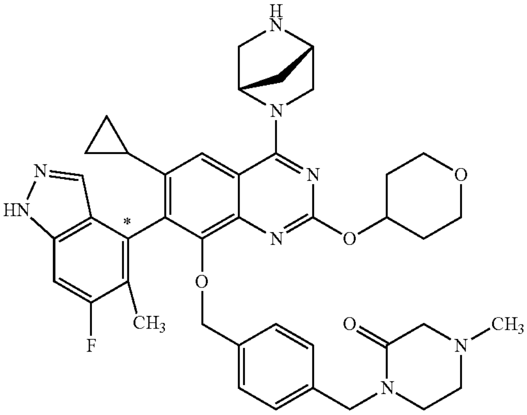 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(CN2CCN(C)CC2=O)cc1] |

TABLE 30-continued
| Ex | Str |
|---|---|
| 3 | 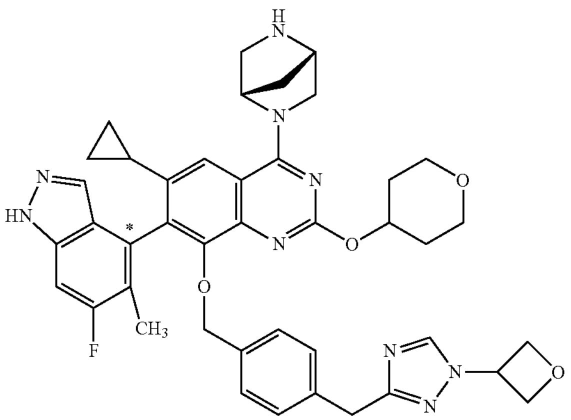 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2ncn(C3COC3)n2)cc1] |
TABLE 31
| Ex | Str |
|---|---|
| 4 | 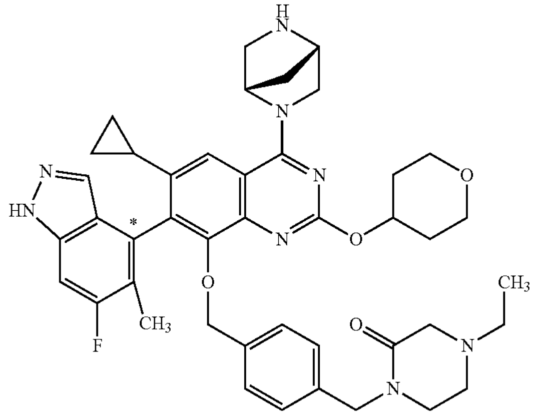 [SMILES: CCN1CCN(Cc2ccc(COc3c(-c4c(C)c(F)cc5[nH]ncc45)c(C4CC4)cc4c(N5C[C@@H]6C[C@H]5CN6)nc(OC5CCOCC5)nc34)cc2)C(=O)C1] |
| 5 | 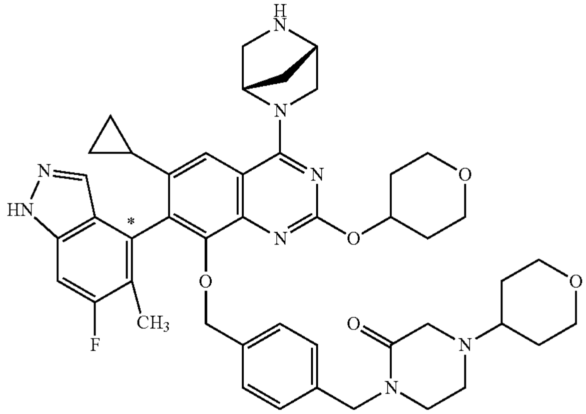 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(CN2CCN(C3CCOCC3)CC2=O)cc1] |

TABLE 31-continued
| Ex | Str |
|---|---|
| 6 | 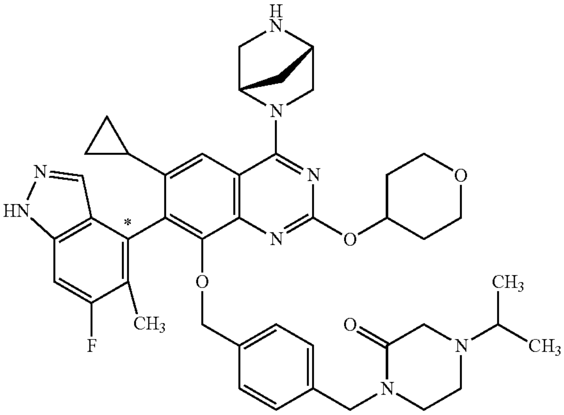 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(CN2CCN(C(C)C)CC2=O)cc1] |
TABLE 32
| Ex | Str |
|---|---|
| 7 | 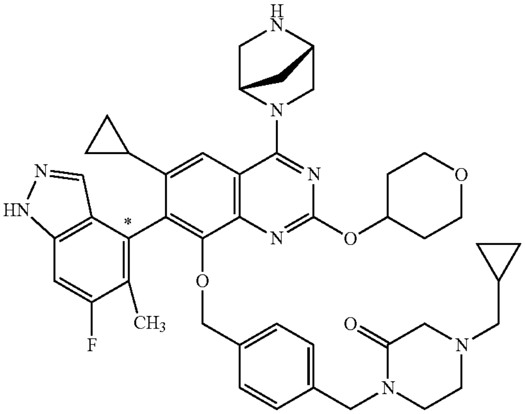 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(CN2CCN(CC3CC3)CC2=O)cc1] |
| 8 | 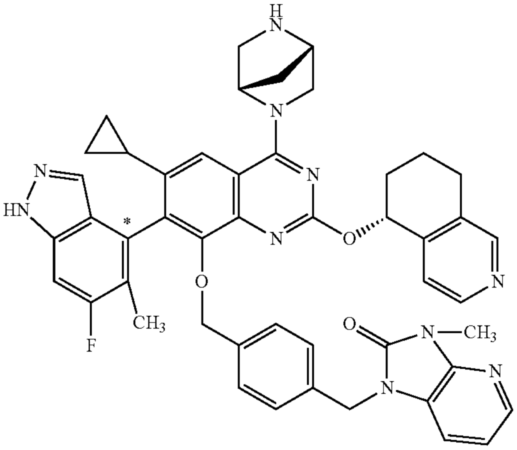 [SMILES: Cc1c(F)cc2[nH]ncc2c1-c1c(C2CC2)cc2c(N3C[C@@H]4C[C@H]3CN4)nc(O[C@@H]3CCCc4cnccc43)nc2c1OCc1ccc(Cn2c(=O)n(C)c3ncccc32)cc1] |

TABLE 32-continued
| Ex | Str |
|---|---|
| 9 | 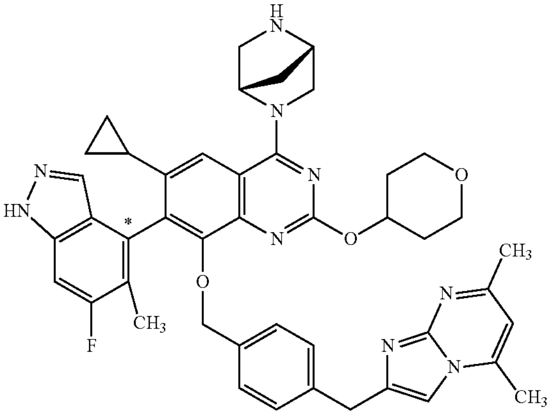 [SMILES: Cc1cc(C)n2cc(Cc3ccc(COc4c(-c5c(C)c(F)cc6[nH]ncc56)c(C5CC5)cc5c(N6C[C@@H]7C[C@H]6CN7)nc(OC6CCOCC6)nc45)cc3)nc2n1] |
TABLE 33
| Ex | Str |
|---|---|
| 10 | 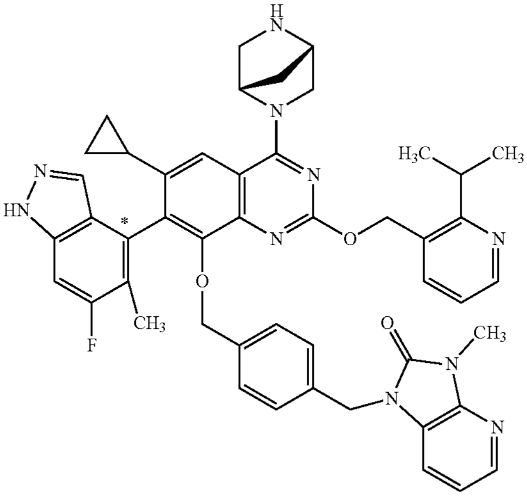 [SMILES: Cc1c(F)cc2[nH]ncc2c1-c1c(C2CC2)cc2c(N3C[C@@H]4C[C@H]3CN4)nc(OCc3cccnc3C(C)C)nc2c1OCc1ccc(Cn2c(=O)n(C)c3ncccc32)cc1] |
| 11 | 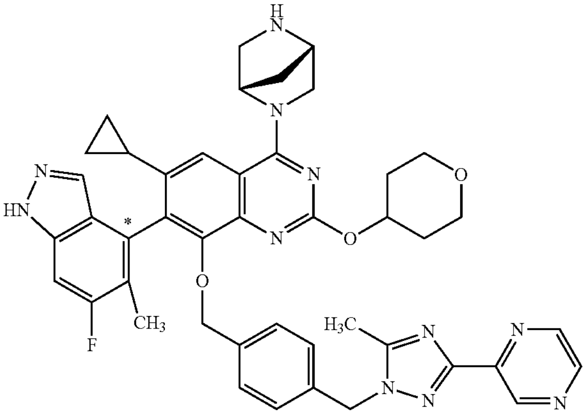 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cn2nc(-c3cnccn3)nc2C)cc1] |

TABLE 33-continued
| Ex | Str |
| --- | --- |
| 12 | 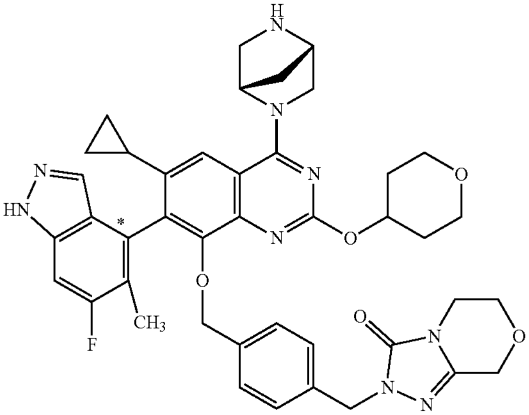 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cn2nc3n(c2=O)CCOC3)cc1] |
TABLE 34
| Ex | Str |
| --- | --- |
| 13 | 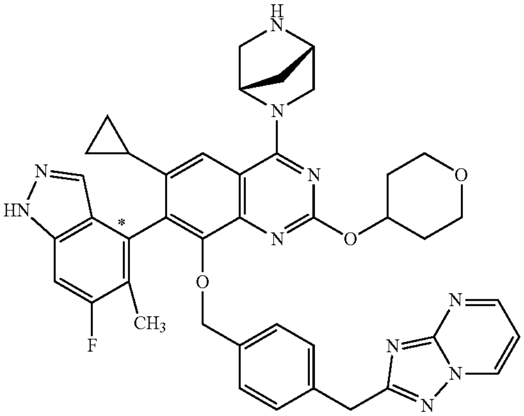 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2nc3ncccn3n2)cc1] |
| 14 | 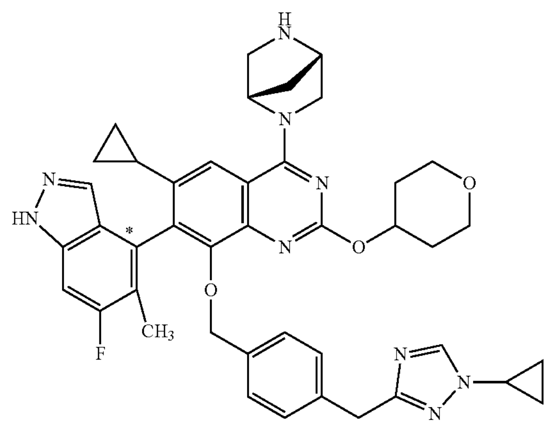 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2ncn(C3CC3)n2)cc1] |
TABLE 34-continued
| Ex | Str |
| --- | --- |
| 15 | 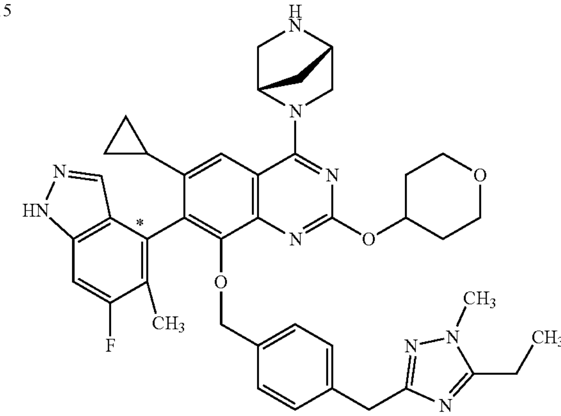 |
TABLE 35
| Ex | Str |
| --- | --- |
| 16 | 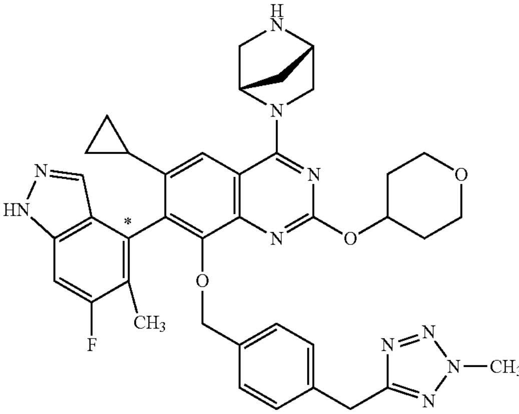 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2nnn(C)n2)cc1] |

TABLE 35-continued
| Ex | Str |
|---|---|
| 17 | 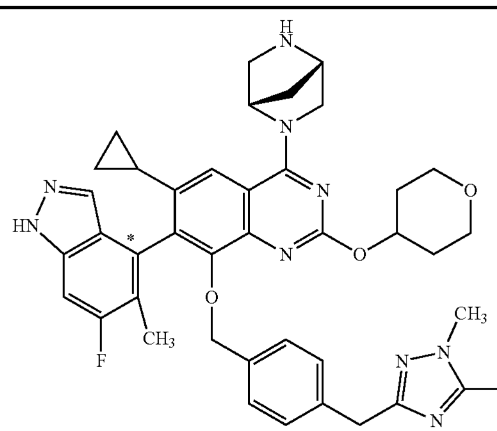 |
TABLE 35-continued
| Ex | Str |
|---|---|
| 18 | 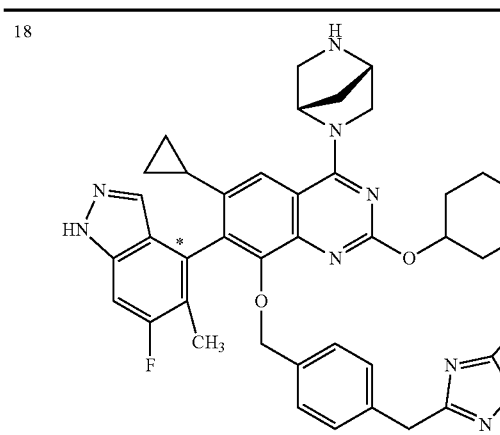 |
TABLE 36
| Ex | Str |
|---|---|
| 19 | 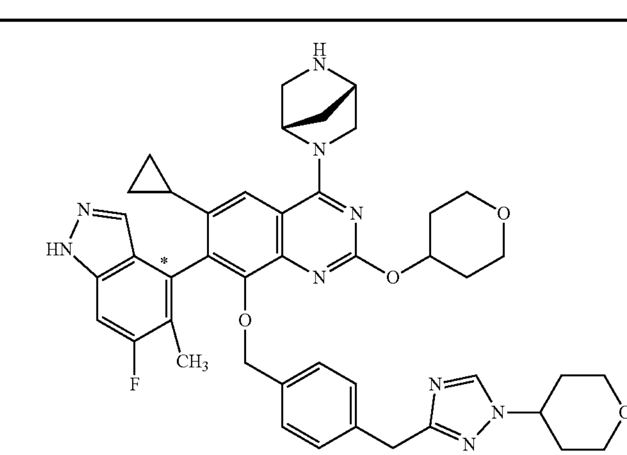 |
| 20 | 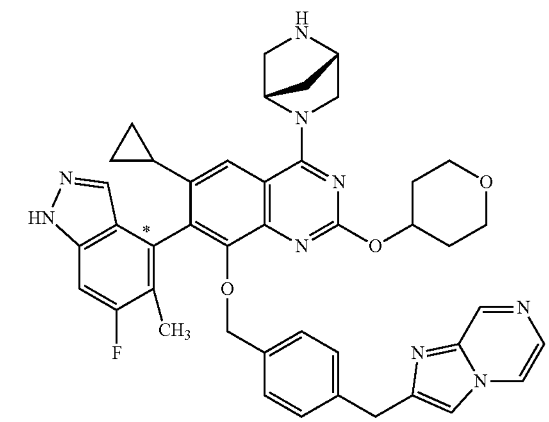 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2cn3ccncc3n2)cc1] |

TABLE 36-continued

| Ex | Str |
|---|---|
| 21 | 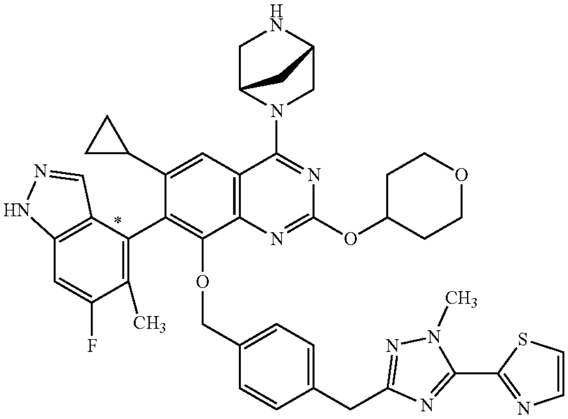 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2nc(-c3nccs3)n(C)n2)cc1] |

TABLE 37

| Ex | Str |
|---|---|
| 22 | 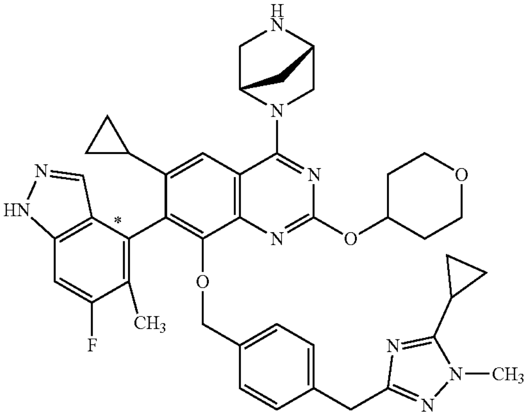 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(Cc2nc(C3CC3)n(C)n2)cc1] |
| 23 | 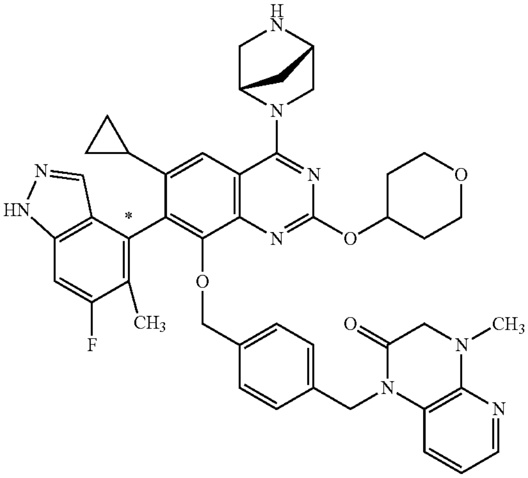 [SMILES: Cc1c(F)cc2[nH]ncc2c1-c1c(C2CC2)cc2c(N3C[C@@H]4C[C@H]3CN4)nc(OC3CCOCC3)nc2c1OCc1ccc(CN2C(=O)CN(C)c3ncccc32)cc1] |

TABLE 38

| Ex | Syn | DAT |
|---|---|---|
| 1 | 1 | ESI+: 783.6<br>NMR: 0.49-0.68 (4H, m), 1.27-1.35 (1H, m), 1.53-1.64 (2H, m), 1.68-1.75 (1H, m), 1.84-1.90 (1H, m), 1.90-2.01 (5H, m), 2.94-3.02 (1H, m), 3.05-3.21 (3H, m), 3.35 (3H, s), 3.67-3.77 (4H, m), 4.19-4.24 (1H, m), 4.65 (1H, d, J = 11.4 Hz), 4.96 (2H, s), 5.02-5.11 (2H, m), 5.19 (1H, d, J = 11.4 Hz), 6.73 (2H, d, J = 8.1 Hz), 7.16 (2H, d, J = 8.1 Hz), 7.34 (1H, d, J = 9.9 Hz), 7.41-7.46 (2H, m), 7.92 (1H, d, J = 3.3 Hz), 7.95 (1H, d, J = 3.3 Hz), 13.07 (1H, brs) |
| 2 | 1 | ESI+: 747.5 |
| 3 | 1 | ESI+: 758.6 |
| 4 | 1 | ESI+: 761.6 |
| 5 | 1 | ESI+: 817.7 |
| 6 | 1 | ESI+: 775.6 |
| 7 | 1 | ESI+: 787.6 |
| 8 | 1 | ESI+: 829.5 |
| 9 | 1 | ESI+: 780.5 |
| 10 | 1 | ESI+: 831.5 |
| 11 | 1 | ESI+: 794.6 |
| 12 | 1 | ESI+: 774.5 |
| 13 | 1 | ESI+: 753.6 |
| 14 | 1 | ESI+: 742.6 |
| 15 | 1 | ESI+: 744.6 |
| 16 | 1 | ESI+: 717.6 |
| 17 | 1 | ESI+: 766.5 |
| 18 | 1 | ESI+: 742.5 |
| 19 | 1 | ESI+: 786.5 |
| 20 | 1 | ESI+: 752.5 |
| 21 | 1 | ESI+: 799.5 |
| 22 | 1 | ESI+: 756.7 |
| 23 | 1 | ESI+: 796.6 |

Compounds having any of the following structures are given as examples of specific compounds of the formula (I) included in the present invention. These compounds were produced by the typical production methods described above, the production methods of the Production Examples and the Examples, a combination of the production methods or a method that is obvious to a person skilled in the art.

Furthermore, the compounds were found to have a G12D mutant KRAS inhibition activity by the test methods of the Test Examples described above. Accordingly, the compounds can be used as an active ingredient of a pharmaceutical composition, for example, a pharmaceutical composition for treating pancreatic cancer.

[Chemical Formula 24]
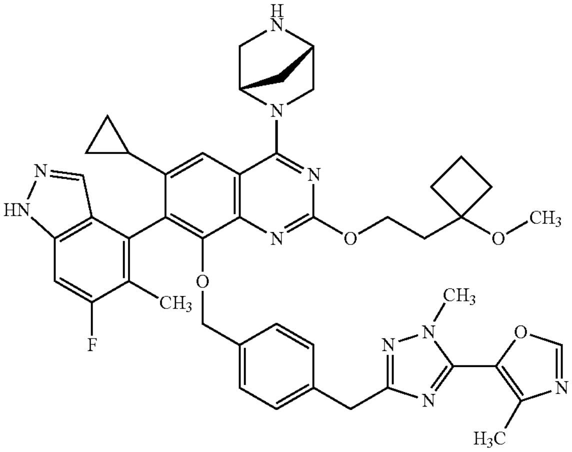
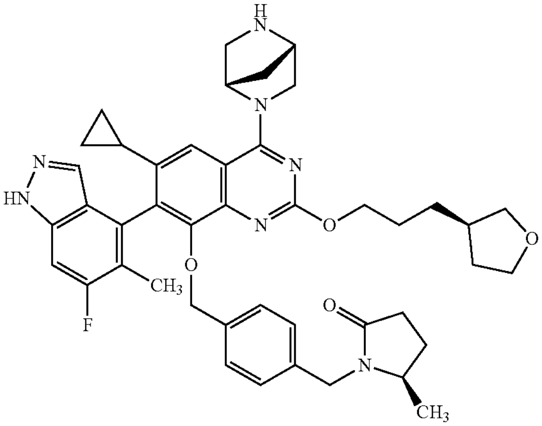
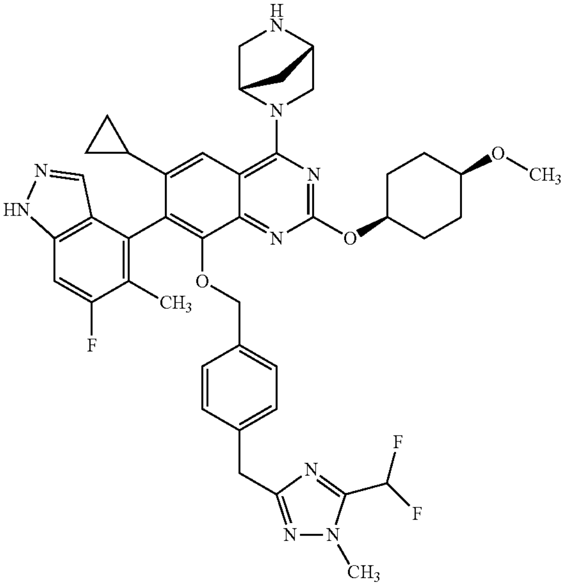
-continued
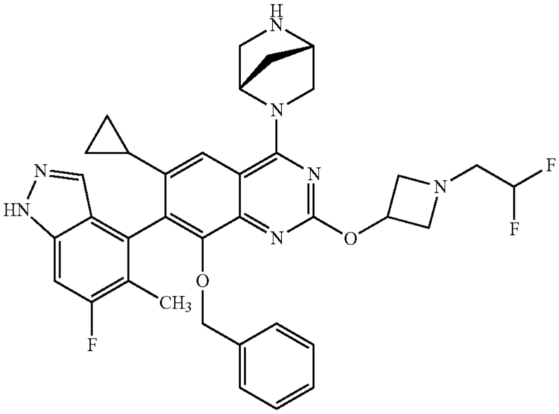
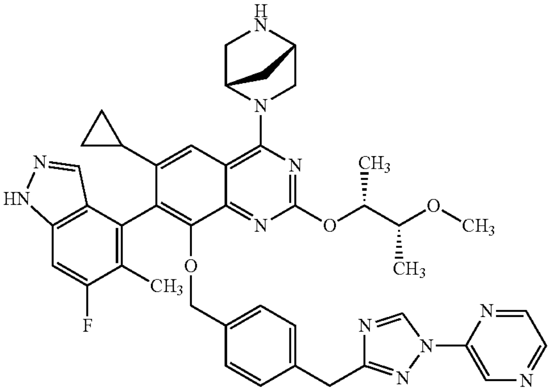
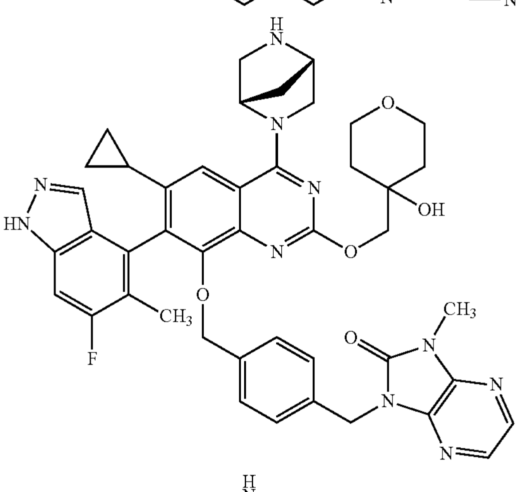
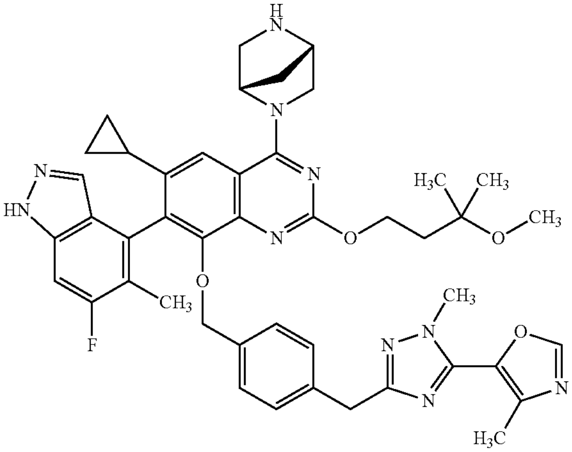

-continued
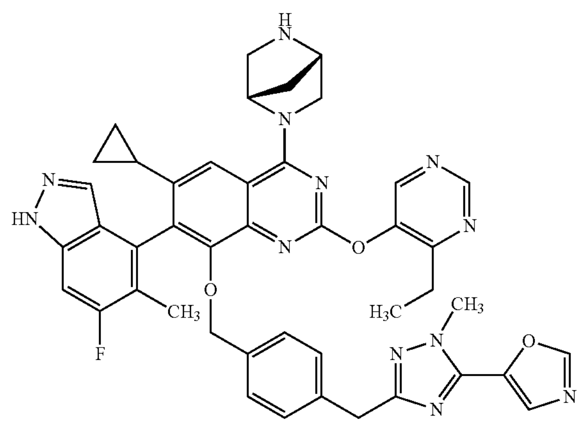
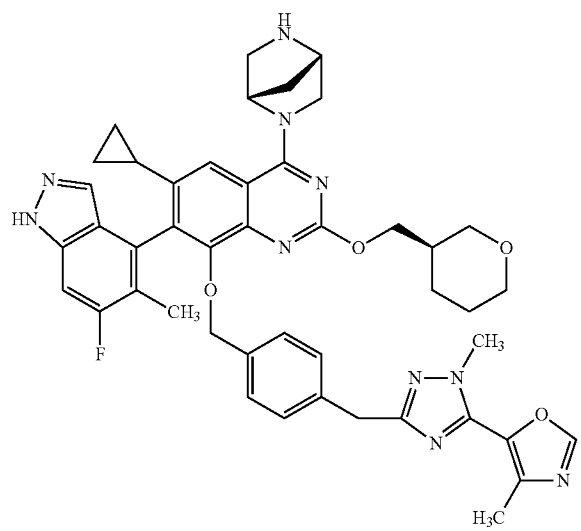
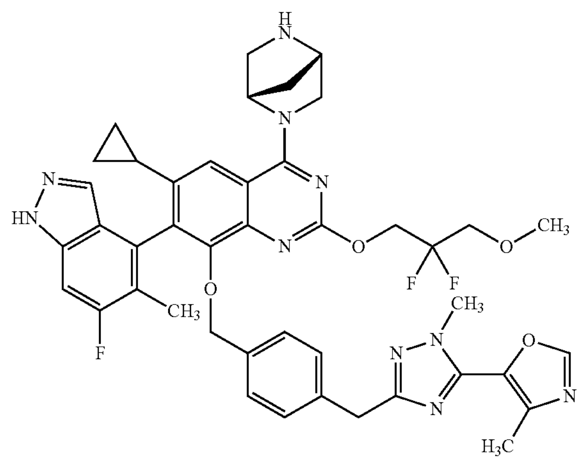
-continued
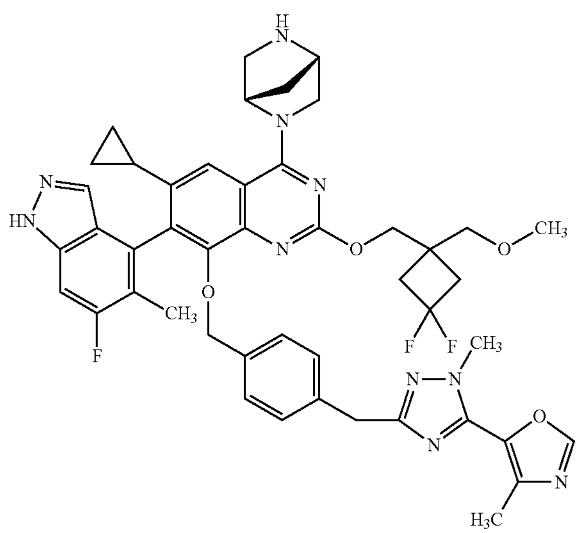
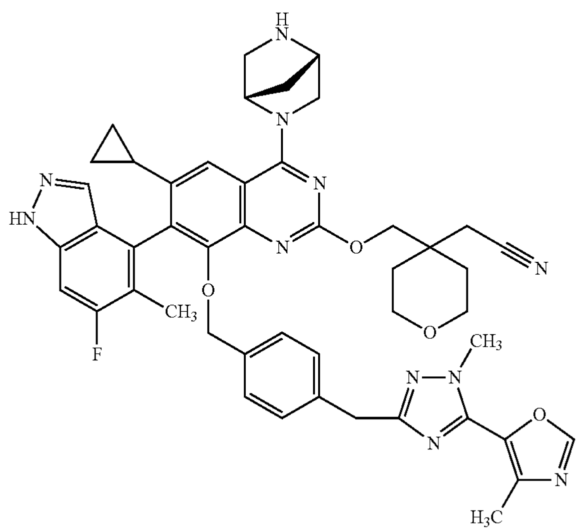
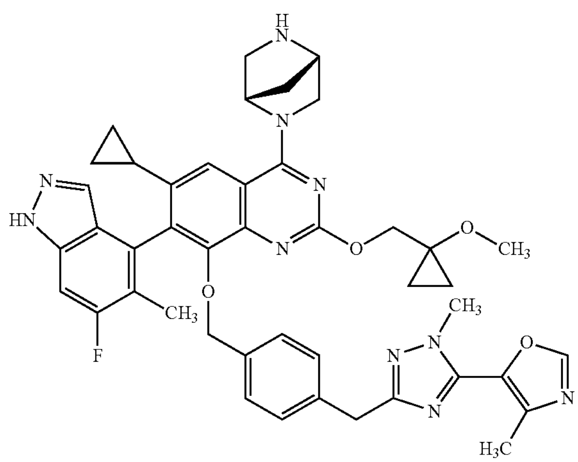

-continued
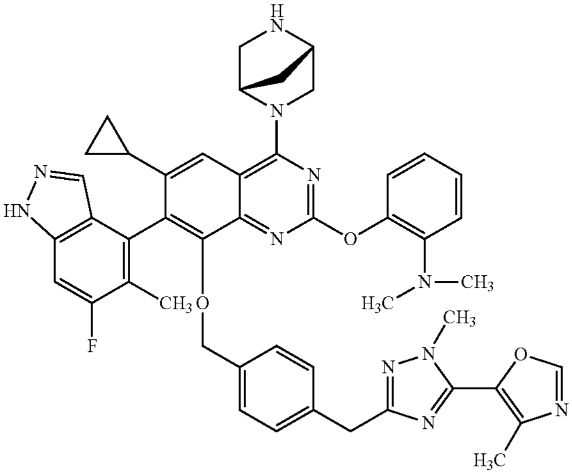
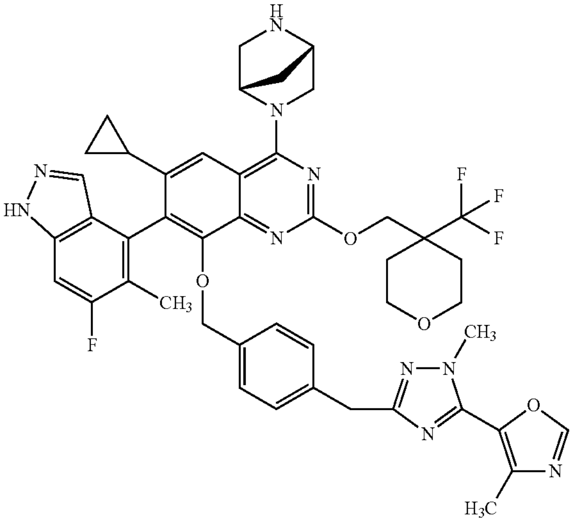
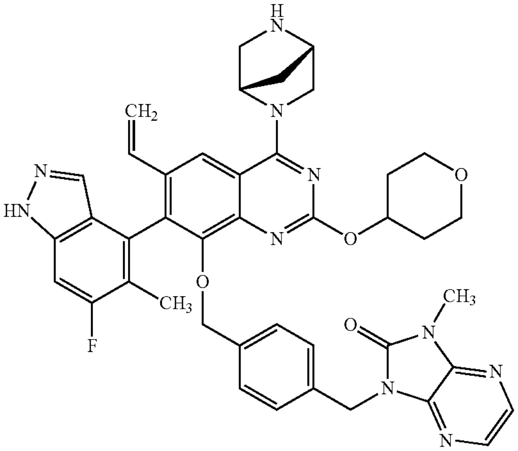
-continued
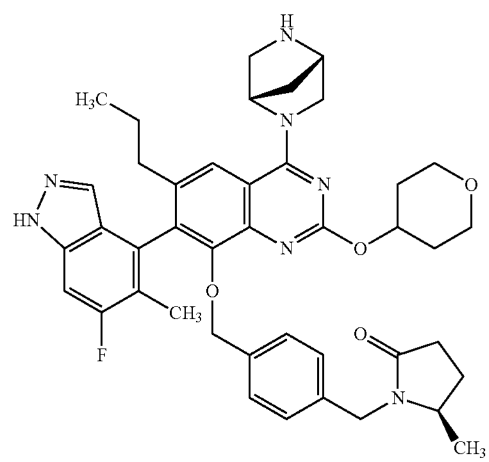
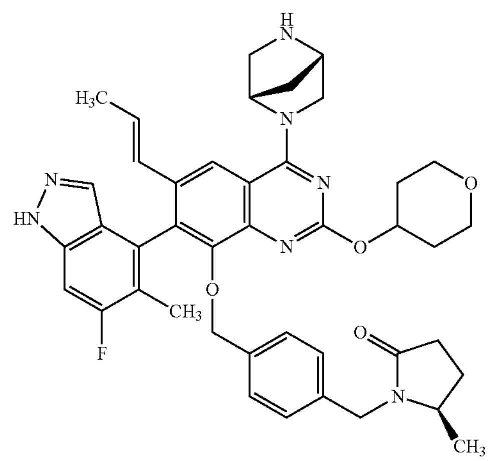
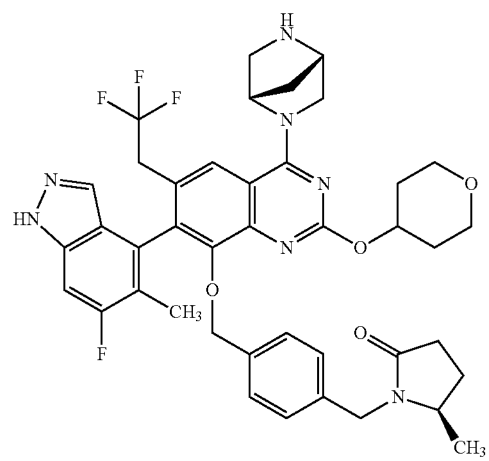

-continued
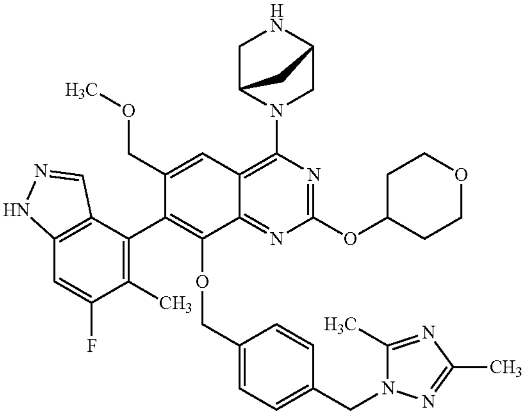
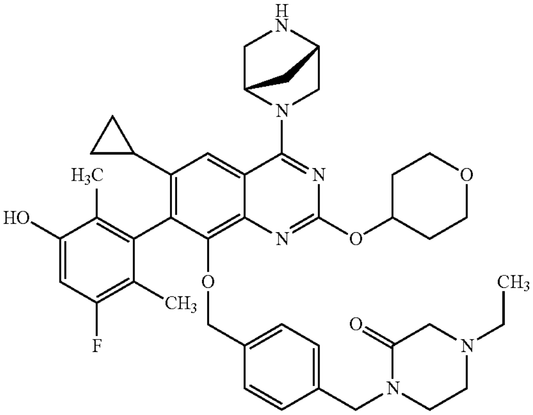
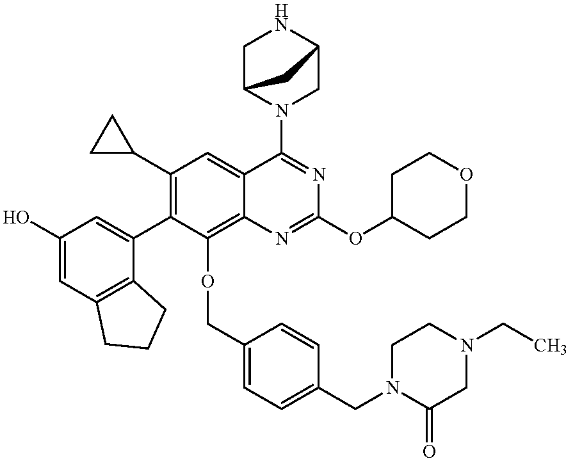
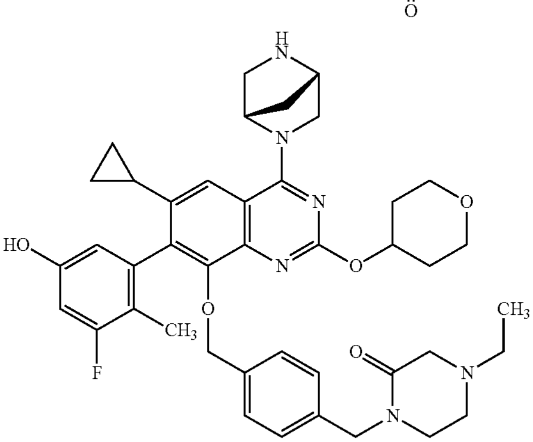
-continued
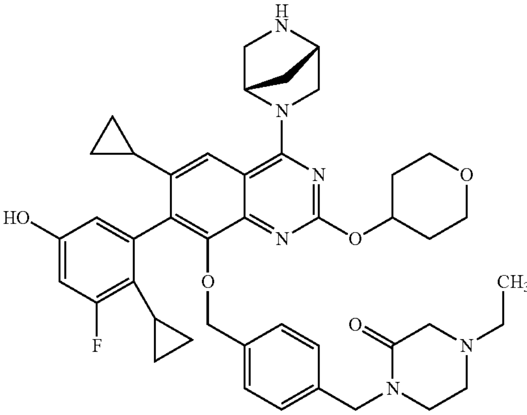
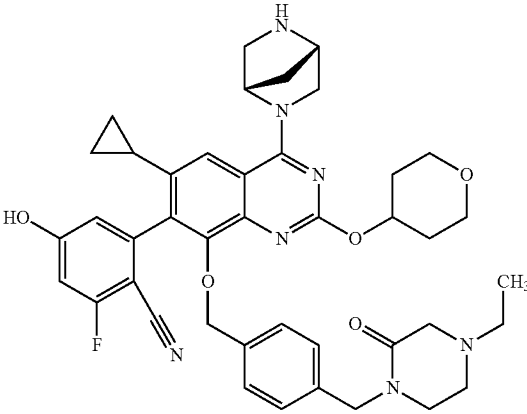
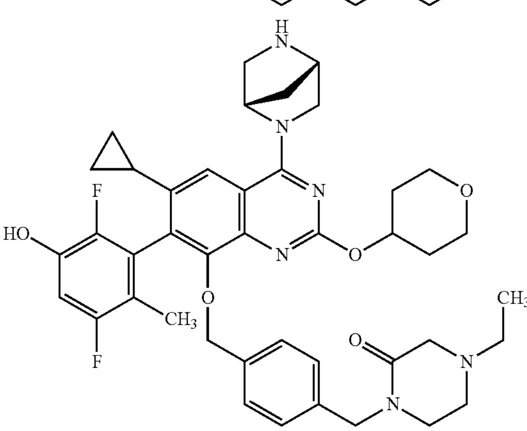
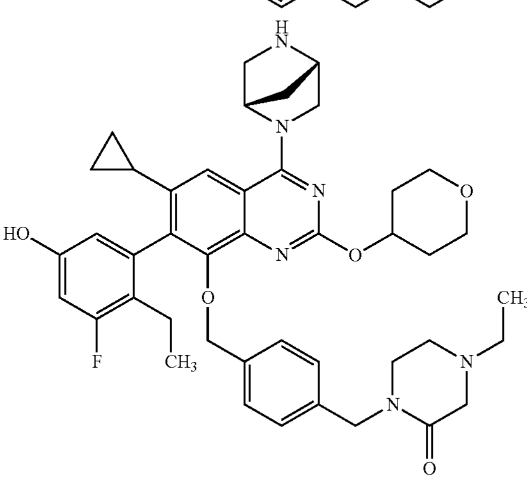

-continued
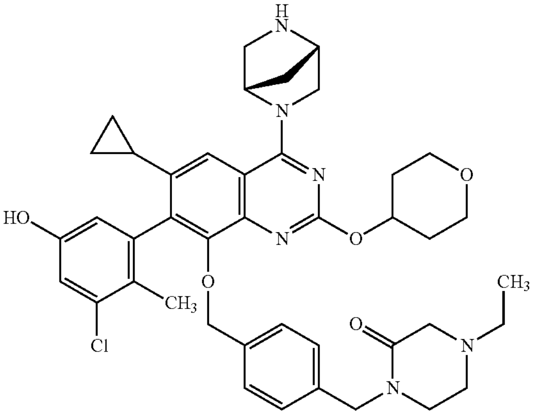
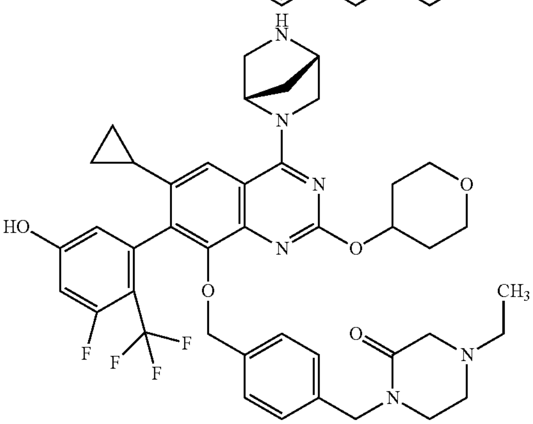
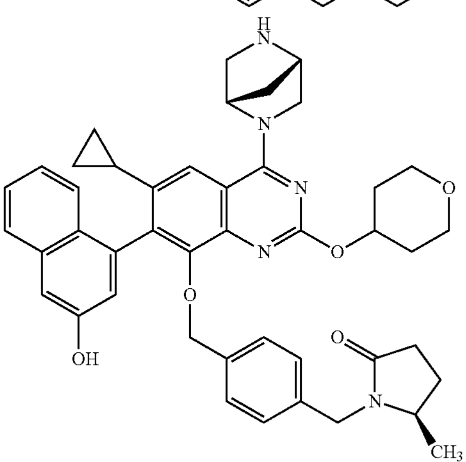
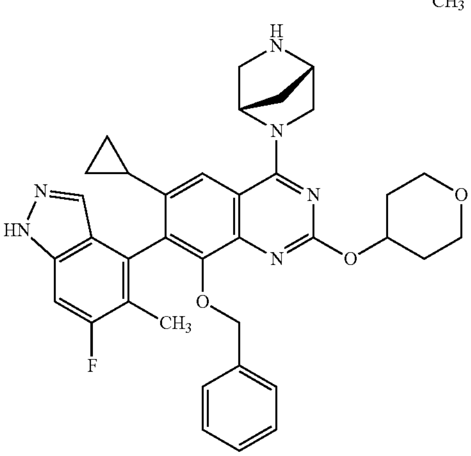
-continued
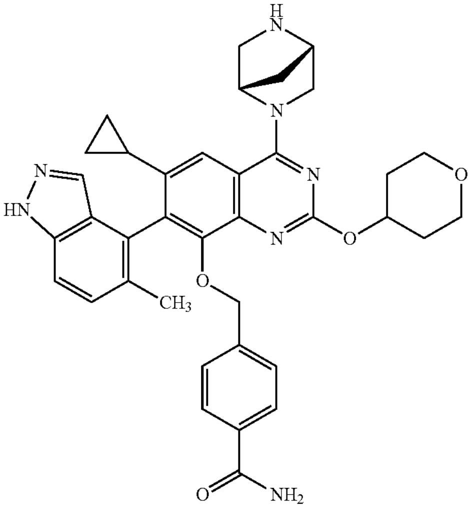
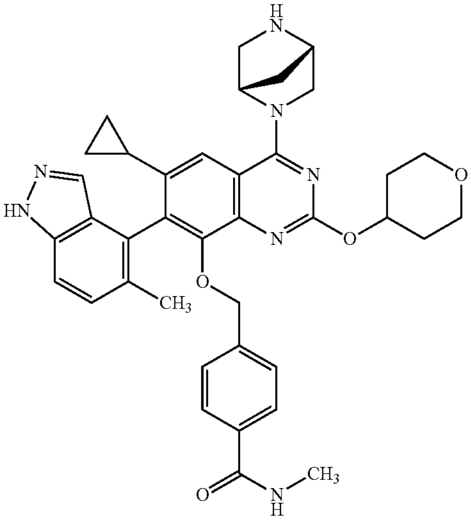
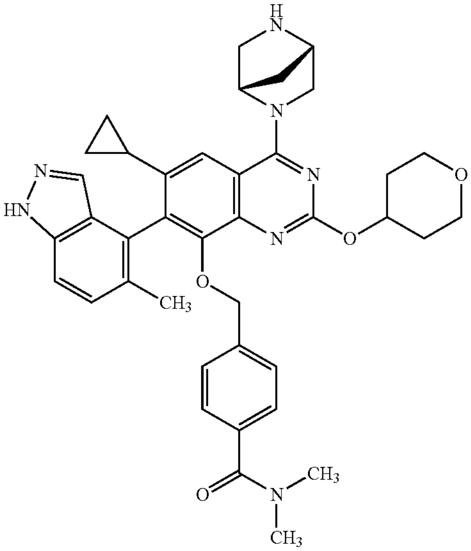 [SMILES: Cc1ccc2[nH]ncc2c1-c1c(C2CC2)cc2c(N3C[C@@H]4C[C@H]3CN4)nc(OC3CCOCC3)nc2c1OCc1ccc(C(=O)N(C)C)cc1]

-continued
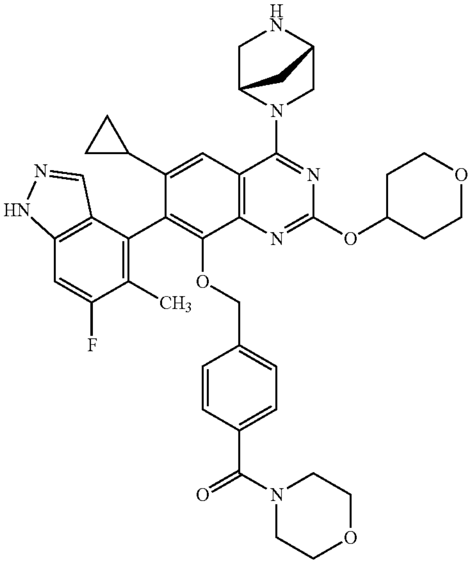
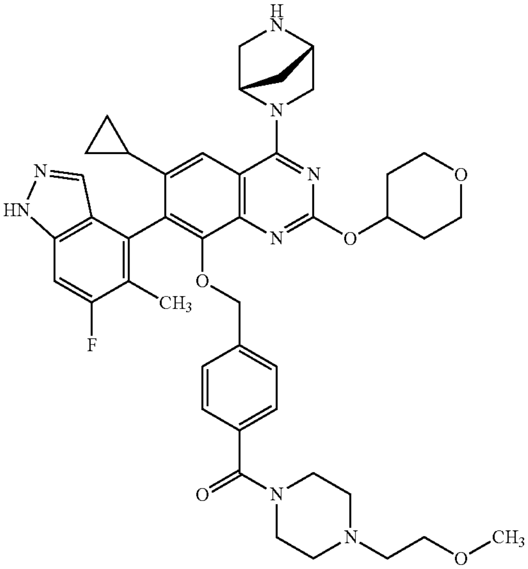
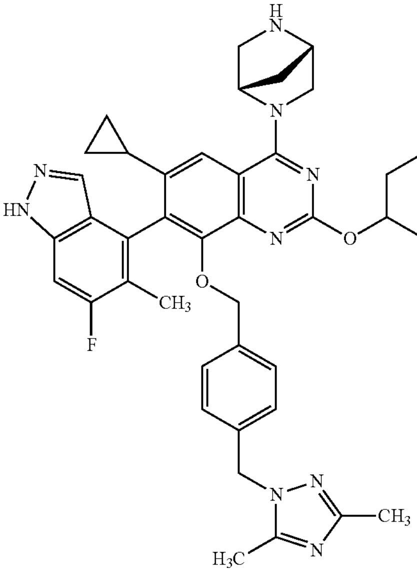
-continued
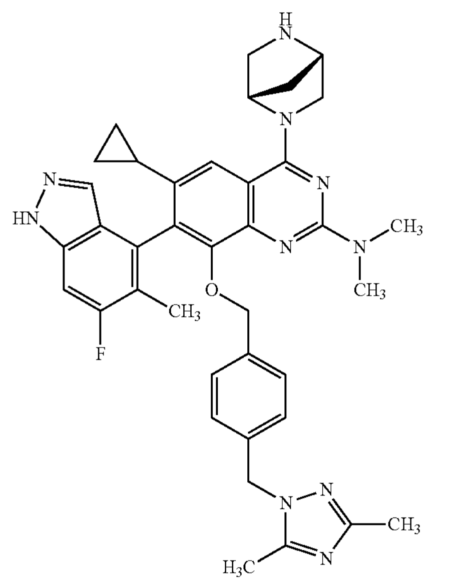
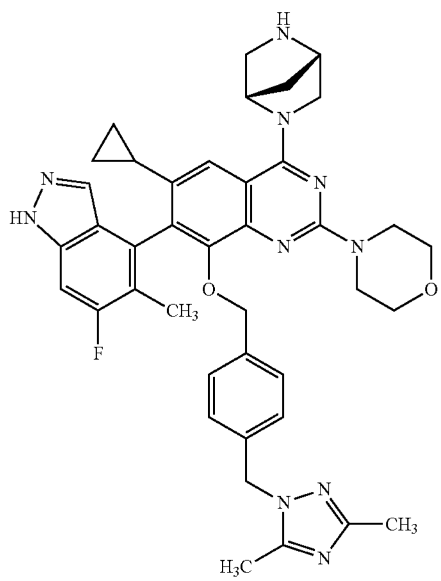
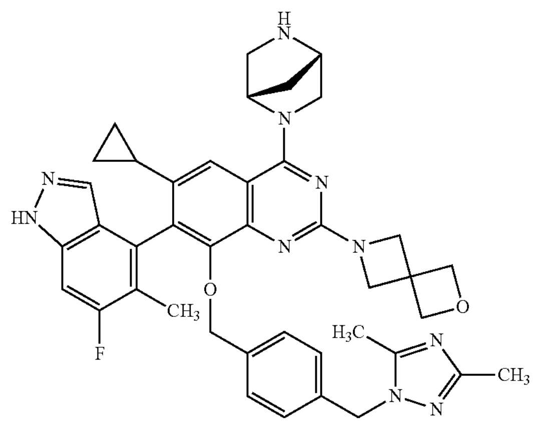

-continued

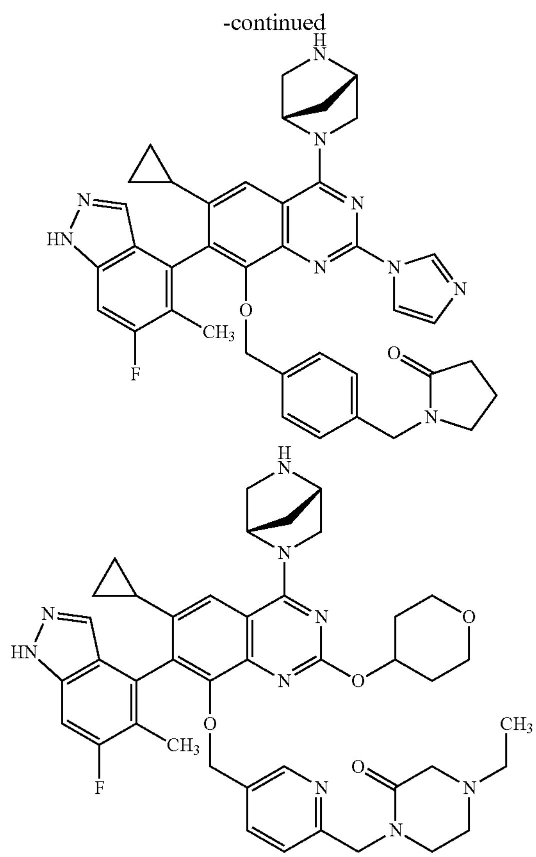

INDUSTRIAL APPLICABILITY

The compound of the present invention or a salt thereof is useful as a G12D mutant KRAS inhibitor and can be used as an active ingredient of a pharmaceutical composition, for example, a pharmaceutical composition for treating pancreatic cancer.

The invention claimed is:

1. A compound represented by formula (I):

(I)

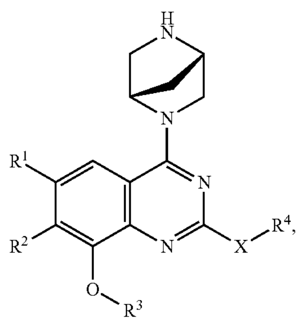

or a salt of the compound, wherein:

$R^1$ is $C_{1-3}$ alkyl, halogen, cyclopropyl, or $C_{2-3}$ alkenyl, wherein the $C_{1-3}$ alkyl group is optionally substituted with a group selected from F and $OCH_3$;

$R^2$ is naphthyl, formula (IIa), or formula (IIb), wherein the naphthyl group is optionally substituted with OH, wherein formula (IIa) and formula (IIb) are represented by the following structural formulae:

(IIa)

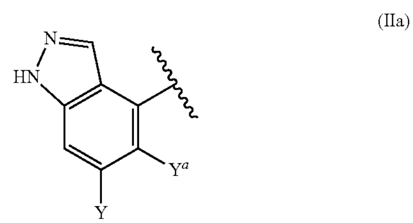

(IIb)

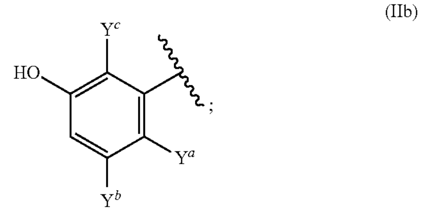

$R^3$ is a group of formula (III), represented by the following structural formula:

(III)

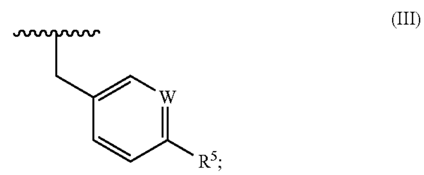

$R^4$ is optionally substituted $C_{1-6}$ alkyl, optionally substituted $C_{3-6}$ cycloalkyl, optionally substituted 4-membered to 7-membered saturated heterocyclic group, optionally substituted 6-membered heteroaryl or tetrahydroisoquinolinyl;

$R^5$ is H, $CONR^6R^7$ or a group selected from formulae (IV), (V), (VI), (VII), (VIII), (IX), (X), (XI), (XII), (XIII), (XIV), and (XV), represented by the following structural formulae:

(IV)

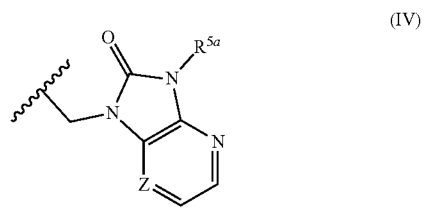

(V)

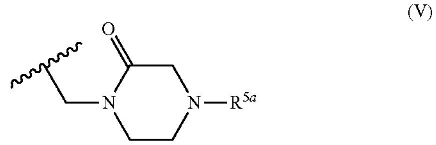

(VI)

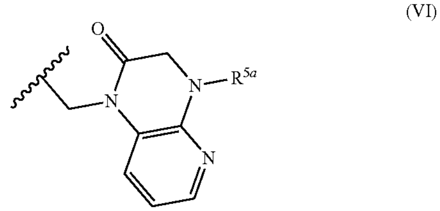

-continued (VII)

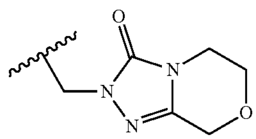

(VIII)

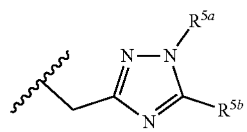

(IX)

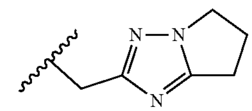

(X)

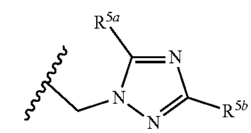

(XI)

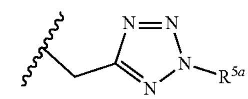

(XII)

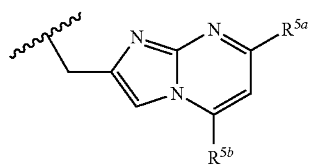

(XIII)

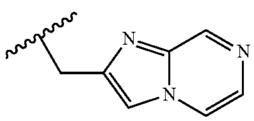

(XIV)

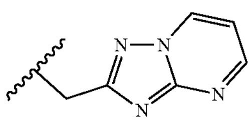

(XV)

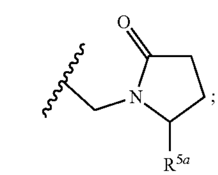

wherein $R^{5a}$ and $R^{5b}$ are each independently H, optionally substituted $C_{1-3}$ alkyl, cyclopropyl, cyclopropylmethyl, oxetanyl, tetrahydropyranyl, optionally substituted oxazolyl, thiazolyl, or pyrazinyl;

$R^6$ and $R^7$ are each independently H or optionally substituted $C_{1-6}$ alkyl, or $R^6$ and $R^7$, together with the nitrogen to which they are attached, may form a 4-membered to 7-membered saturated heterocyclic ring, wherein the 4-membered to 7-membered saturated heterocyclic ring is optionally substituted with optionally substituted $C_{1-6}$ alkyl, W is CH or N, X is O or $NR^x$, wherein $R^x$ is H or $C_{1-3}$ alkyl, or X—$R^4$ is a 4-membered to 7-membered saturated heterocyclic group or imidazolyl, Y and $Y^b$ are each independently H, F or Cl, $Y^a$ is $C_{1-3}$ alkyl optionally substituted with F, cyano, or cyclopropyl, or $Y^a$ and $Y^b$, together with the carbon to which they are attached, form cyclopentenyl;

$Y^c$ is H, F, or methyl, and

Z is N or CH.

2. The compound or the salt according to claim 1, wherein $R^1$ is cyclopropyl, $R^2$ is a group of formula (IIc), represented by the following structural formula:

(IIc)

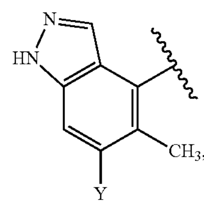

$R^3$ is a group of formula (IIIa), represented by the following structural formula:

(IIIa)

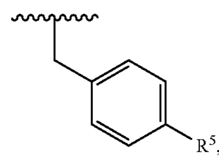

$R^4$ is tetrahydropyranyl, optionally substituted pyridylmethyl, or tetrahydroisoquinolinyl, $R^5$ is a group selected from formulae (IV), (V), (VI), (VII), (VIII), (IX), (X), (XI), (XII), (XIII), and (XIV), represented by the following structural formulae:

(IV)

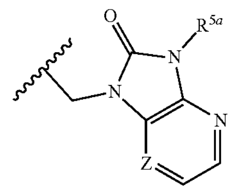

(V)

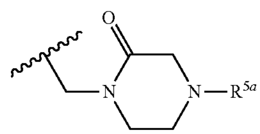

(VI)

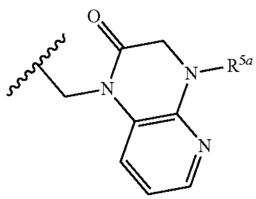

-continued (VII)

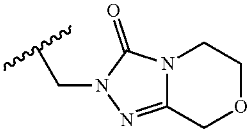

(VIII)

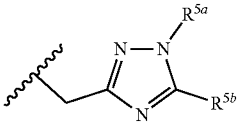

(IX)

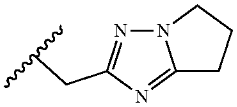

(X)

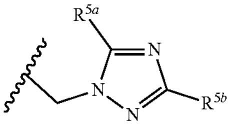

(XI)

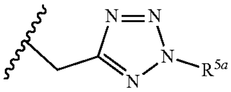

(XII)

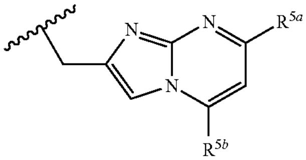

(XIII)

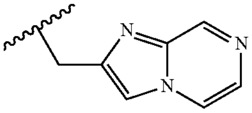

(XIV)

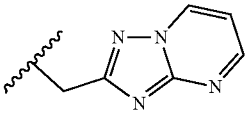

, wherein $R^{5a}$ and $R^{5b}$ are each independently H, optionally substituted $C_{1-3}$ alkyl, cyclopropyl, cyclopropylmethyl, oxetanyl, tetrahydropyranyl, thiazolyl, or pyrazinyl, X is O, Y is F, and Z is N or CH.

3. The compound or the salt according to claim 2, wherein the compound of formula (I) is selected from the group consisting of:

1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-3-methyl-1,3-dihydro-2H-imidazo[4,5-b]pyrazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-methylpiperazin-2-one, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-[(4-{[1-(oxetan-3-yl)-1H-1,2,4-triazol-3-yl]methyl}phenyl)methoxy]quinazoline, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-ethylpiperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(oxan-4-yl) piperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(propan-2-yl) piperazin-2-one, 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-(cyclopropylmethyl) piperazin-2-one, 1-[(4-{[(6-cyclopropyl-4-[(1S,4S)-2,5-diazabicyclo[2.2.1]heptan-2-yl]-7-(6-fluoro-5-methyl-1H-indazol-4-yl)-2-{[(5R)-5,6,7,8-tetrahydroisoquinolin-5-yl]oxy}quinazolin-8-yl)oxy]methyl}phenyl)methyl]-3-methyl-1,3-dihydro-2H-imidazo[4,5-b]pyridin-2-one, 6-cyclopropyl-4-[(1S,4S)-2,5-diazabicyclo[2.2.1]heptan-2-yl]-8-({4-[(5,7-dimethylimidazo[1,2-a]pyrimidin-2-yl)methyl]phenyl}methoxy)-7-(6-fluoro-5-methyl-1H-indazol-4-yl)-2-[(oxan-4-yl)oxy]quinazoline, 1-[(4-{[(6-cyclopropyl-4-[(1S,4S)-2,5-diazabicyclo[2.2.1]heptan-2-yl]-7-(6-fluoro-5-methyl-1H-indazol-4-yl)-2-{[2-(propan-2-yl) pyridin-3-yl]methoxy}quinazolin-8-yl)oxy]methyl}phenyl)methyl]-3-methyl-1,3-dihydro-2H-imidazo[4,5-b]pyridin-2-one, 6-cyclopropyl-4-[(1S,4S)-2,5-diazabicyclo[2.2.1]heptan-2-yl]-7-(6-fluoro-5-methyl-1H-indazol-4-yl)-8-[(4-{[5-methyl-3-(pyrazin-2-yl)-1H-1,2,4-triazol-1-yl]methyl}phenyl)methoxy]-2-[(oxan-4-yl)oxy]quinazoline, 2-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-2,5,6,8-tetrahydro-3H-[1,2,4]triazolo[3,4-c][1,4]oxazin-3-one, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-({4-[([1,2,4]triazolo[1,5-a]pyrimidin-2-yl)methyl]phenyl}methoxy)quinazoline, 6-cyclopropyl-8-({4-[(1-cyclopropyl-1H-1,2,4-triazol-3-yl)methyl]phenyl}methoxy)-4-[(1S,4S)-2,5-diazabicyclo[2.2.1]heptan-2-yl]-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-8-({4-[(5-ethyl-1-methyl-1H-1,2,4-triazol-3-yl)methyl]phenyl}methoxy)-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-({4-[(2-methyl-2H-tetrazol-5-yl)methyl]phenyl}methoxy)-2-[(oxan-4-yl)oxy]quinazoline, 6-cyclopropyl-4-[(1S,4S)-2,5-diazabicyclo[2.2.1]heptan-2-yl]-8-[(4-{[5-(difluoromethyl)-1-methyl-1H-1,2,4-triazol-3-yl]methyl}phenyl)methoxy]-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-8-({4-[(6,7-dihydro-5H-pyrrolo[1,2-b][1,2,4]triazol-2-yl)methyl]phenyl}methoxy)-7-(6-fluoro-5-methyl-1H-indazol-4-yl)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]-8-[(4-{[1-(oxan-4-yl)-1H-1,2,4-triazol-3-yl]methyl}phenyl)methoxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-({4-[(imidazo[1,2-a]pyrazin-2-yl)methyl]phenyl}methoxy)-2-[(oxan-4-yl)oxy]quinazoline, 6-cyclopropyl-4-[(1S,4S)-2,5-diazabicyclo[2.2.1]heptan-2-yl]-7-(6-fluoro-5-methyl-1H-indazol-4-yl)-8-[(4-{[1-methyl-5-(1,3-thiazol-2-yl)-1H-1,2,4-triazol-3-yl]methyl}phenyl)methoxy]-2-[(oxan-4-yl)oxy]quinazoline, 6-cyclopropyl-8-({4-[(5-cyclopropyl-1-methyl-1H-1,2,4-triazol-3-yl)methyl]phenyl}methoxy)-4-[(1S,4S)-2,5-diazabicyclo[2.2.1]heptan-2-yl]-7-(6-fluoro-5-methyl-1H-indazol-4-yl)-2-[(oxan-4-yl)oxy]quinazoline, and 1-({4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]phenyl}methyl)-4-methyl-3,4-dihydropyrido[2,3-b]pyrazin-2(1H)-one.

4. A pharmaceutical composition comprising at least one compound or salt thereof selected from claim 1 or 3, and a pharmaceutically acceptable excipient.

5. A method of treating pancreatic cancer comprising administering to a subject in need thereof a therapeutically effective amount of at least one compound or salt thereof selected from claim 1 or 3.

6. The compound or the salt according to claim 1, wherein $R^4$ is:

$C_{1-6}$ alkyl, wherein $C_{1-6}$ alkyl is further optionally substituted with a group selected from:

F;

$OCH_3$;

cyclopropyl optionally substituted with $OCH_3$;

cyclobutyl optionally substituted with F or methoxymethyl;

oxetanyl optionally substituted with $OCH_3$;

tetrahydrofuranyl;

tetrahydropyranyl optionally substituted with OH, $CF_3$, or cyanomethyl; and pyridyl optionally substituted with $C_{1-3}$ alkyl;

$C_{3-6}$ cycloalkyl optionally substituted with $OCH_3$;

azetidinyl optionally substituted with F;

tetrahydropyranyl;

pyrimidinyl optionally substituted with $C_{1-3}$ alkyl or $N(CH_3)_2$; or tetrahydroisoquinolinyl, X is O or $NR^x$, wherein $R^x$ is H or $C_{1-3}$ alkyl, or X—$R^4$ is a morpholinyl, oxazaspiro[3.3]heptanyl, or imidazolyl.

* * * * *